US006767904B2

(12) United States Patent
Savage et al.

(10) Patent No.: US 6,767,904 B2
(45) Date of Patent: Jul. 27, 2004

(54) STEROID DERIVED ANTIBIOTICS

(75) Inventors: Paul B. Savage, Springville, UT (US); Chunhong Li, Provo, UT (US)

(73) Assignee: Bringham Young University, Provo, UT (US)

( * ) Notice: Subject to any disclaimer, the term of this patent is extended or adjusted under 35 U.S.C. 154(b) by 0 days.

(21) Appl. No.: 09/930,316

(22) Filed: Aug. 15, 2001

(65) Prior Publication Data

US 2002/0091278 A1 Jul. 11, 2002

Related U.S. Application Data

(63) Continuation-in-part of application No. 09/234,008, filed as application No. PCT/US98/04489 on Mar. 6, 1998, now Pat. No. 6,350,738.
(60) Provisional application No. 60/225,467, filed on Aug. 15, 2000.

(51) Int. Cl.[7] .............................. A61K 31/56; C07J 9/00; C07J 41/00
(52) U.S. Cl. ......................... 514/182; 552/548; 552/550
(58) Field of Search ........................... 514/182; 552/548, 552/550

(56) References Cited

U.S. PATENT DOCUMENTS

| | | | |
|---|---|---|---|
| 3,519,714 A | 7/1970 | Hughes et al. | |
| 4,158,707 A | 6/1979 | Steffen et al. | |
| 4,192,871 A | 3/1980 | Phillipps et al. | |
| 4,299,726 A | 11/1981 | Crews et al. | |
| 4,565,810 A | 1/1986 | Castagnola et al. | |
| 4,892,868 A | 1/1990 | Castagnola et al. | |
| 4,981,983 A | 1/1991 | Castagnola et al. | |
| 5,268,272 A | 12/1993 | Müllner et al. | |
| 5,364,632 A | 11/1994 | Benita et al. | |
| 5,446,026 A | 8/1995 | Ruff et al. | |
| 5,622,944 A * | 4/1997 | Hale et al. | 514/181 |
| 5,637,691 A | 6/1997 | Frye et al. | |
| 5,804,563 A | 9/1998 | Still et al. | |
| 5,834,453 A | 11/1998 | Regen | |
| 6,350,738 B1 * | 2/2002 | Savage et al. | 514/182 |

FOREIGN PATENT DOCUMENTS

| | | |
|---|---|---|
| EP | 0 113 998 | 7/1984 |
| EP | 0 124 068 | 11/1984 |
| EP | 0 135 782 | 5/1985 |
| EP | 0 168 229 | 1/1986 |
| WO | WO 95/19567 | 7/1995 |
| WO | WO 99/31124 | 6/1999 |

OTHER PUBLICATIONS

Nestler, "Sequence–selective nonmacrocyclic two–armed receptors for peptides." Mol. Diversity, vol 2, 35–40, 1996.*
Li et al., "Preparation of Amine–Functionalized Cholic Acid Derivatives for Use as Lipid A Binding Agents", Book of Abstracts, 214th ACS National Meeting, Sep. 7–11, 1997, Poster Session.

Li et al., "Design and Synthesis of Potent Sensitizers of Gram–Negative Bacteria Based on a Cholic Acid Scaffolding", J. Am. Chem. Soc., vol. 120, No. 12, Apr. 1, 1998, 2961–62.
Barnes et al., "Preparation and Characterisation of Permethylated Derivatives of Bile Acids, and Their Application to Gas Chromatographic Analysis", J. of Chromatography, 183, (1980), 269–276.
Bellini et al., "Antimicrobial Activity of Cholane Compounds Cholic and Deoxycholic Acids Derivatives (Part I)", Eur. J. Med. Chem.—Chem. Ther. 1983–18, No. 2, pp. 185–190.
Bellini et al., "Antimicrobial Acitivity of Cholane Compounds Cheno and Ursodeoxycholic Acids Derivatives Part II)", Eur. J. Med. Chem.—Chem. Ther. 1983–18, No. 2, pp. 191–195.
Bowe et al., "Design of Compounds That Increase the Absorption of Polar Molecules", Proc. Natl. Acad. Sci., USA (1997), pp. 12218–12223.
Boyce et al., "Peptidosteroidal Receptors for Opioid Peptides, Sequence–Selective Binding Using a Synthetic Receptor Library", J. Am. Chem. Soc., 1994, 116, 7955–7956.
Broderick et al., "The 'Triamino–analogue' of Methyl Cholate; A Facial Amphiphile and Scaffold with Potential for Combinatorial and Molecular Recognition Chemistry", Tetrahedron Letters, 39, (1998) 6083–6086.
Ding et al., "Correlation of the Antibacterial Activities of Cationic Peptide Antibiotics and Cationic Steroid Antibiotics", J. Med. Chem., pp. 663–669, vol. 45, Jan. 31, 2002.
Paul B. Savage, "Design, Synthesis and Characterization of Cationic Peptide and Steroid Antibiotics", Eur. J. Org. Chem., pp. 759–768, 2002.
Paul B. Savage, "Multidrug–Resistant Bacteria: Overcoming Antibiotic Permeability Barriers of Gram–Negative Bacteria", Ann Med, vol. 33, pp. 167–171, 2001.
Schmidt et al., "Activities of Cholic Acid–Derived Antimicrobial Agents Against Multidrug–Resistant Bacteria", Journal of Antimicrobial Chemotherapy, vol. 47, pp. 671–674, 2001.
Guan et al., "Preparation and Characterization of Cholic Acid–Derived Antimicrobial Agents with Controlled Stabilities", Org. Lett., vol. 2, No. 18, pp. 2837–2840, 2000.
Savage et al., "Cholic Acid Derivatives: Novel Antimicrobials", Exp. Opin. Invest. Drugs, vol. 9, pp. 263–272, 2000.
Jones et al., The synthesis and characterization of analogs of the antimicrobial compound sqalamine: 6β–hydroxy–3–aminosterols synthesized from hyodeoxycholic acid, Steroids, pp. 565–571, vol. 61, Oct. 1996.

(List continued on next page.)

Primary Examiner—Barbara P. Badio
(74) Attorney, Agent, or Firm—Fish & Richardson P.C.

(57) ABSTRACT

A series of novel steroid derivatives are described. The steroid derivatives are antibacterial agents. The steroid derivatives also act to sensitize bacteria to other antibiotics including erythromycin and novobiocin.

16 Claims, 7 Drawing Sheets

OTHER PUBLICATIONS

Cheng et al., "Sequence–Selective Peptide Binding with a Peptido–A,B–trans–steroidal Receptor Selected from an Encoded Combinatorial Receptor Library", J. Am. Chem. Soc., 1996, 118, 1813–1814.

Deng et al., "A Synthetic Loophole that Recognizes Negatively Charged Phospholipid Membranes", J. Am. Chem. Soc. 1996, 118, 8975–8976.

Hsieh et al., "Synthesis and DNA Binding Properties of C3–, C12–, and C24– Substituted Amino–Steroids Derived from Bile Acids", Bioorganic & Medicinal Chemistry, vol. 3, No. 6, pp. 823–838, 1995.

Hsieh et al., "Structural Effects in Novel Steroidal Polyamide–DNA Binding", J. Am. Chem. Soc., vol. 116, No. 26, 1994, pp. 12077–12079.

Moore et al., "Squalamine: An Aminosterol Antibiotic From the Shark", Proc. Natl. Acad. Sci. USA, vol. 90, pp. 1354–1358, Feb. 1993.

H. Peter Nestler, "Sequence–Selective Nonmacrocyclic Two–Armed Receptors for Peptides", Molecular Diversity, 2 (1996) 35–40.

Walker et al., "Cationic Facial Amphiphiles: A Promising Class of Transfection Agents", Proc. Natl. Acad. Sci., vol. 93, pp. 1585–1590, Feb. 1995.

Wess et al., "The Design and Synthesis of a Scaffold for Combinatorial Chemistry Based on Bile Acid", Angew. Chem. Int. Ed. Eng. 1996, 33, No. 19, pp. 2222–2225.

* cited by examiner 352 n = 1; 353 n = 2; 354 n = 3

341 n = 1, R = - (CH₂)₇CH₃   324 n = 1, R = - CH₂CH₂N⁺(CH₃)₃
342 n = 2, R = - (CH₂)₇CH₃   325 n = 2, R = - CH₂CH₂N⁺(CH₃)₃
343 n = 3, R = - (CH₂)₇CH₃   326 n = 3, R = - CH₂CH₂N⁺(CH₃)₃
327 n = 1, R = - H

356

357

358

STEROID DERIVED ANTIBIOTICS

CROSS-REFERENCE TO RELATED APPLICATIONS

This is a continuation-in-part of U.S. patent application Ser. No. 09/234,008, filed Jan. 19, 1999, now U.S. Pat. No. 6,350,738, which is a continuation-in-part of PCT/US 98/04489, filed Mar. 6, 1998, each of which is hereby incorporated by reference in its entirety. This application claims priority from provisional application U.S. No. 60/225,467, filed Aug. 15, 2000, which is hereby incorporated by reference in its entirety.

STATEMENT OF GOVERNMENT INTEREST

This invention was made with support from the National Institutes of Health (GM 54619). The government has certain rights in this invention.

BACKGROUND OF THE INVENTION

The invention relates to novel steroid derivatives and processes and intermediates for the preparation of these compounds.

Some compounds that associate strongly with the outer membrane of Gram-negative bacteria are known to disrupt the outer membrane and increase permeability. The increased permeability can increase the susceptibility of Gram-negative bacteria to other antibiotics. The best studied of this type of compound are the polymyxin antibiotics. For an example of a study involving the binding of polymyxin B to the primary constituent of the outer membrane of Gram-negative bacteria (lipid A) see: D. C. Morrison and D. M. Jacobs, *Binding of Polymyxin B to The Lipid a Portion of Bacterial Lipopolysaccharides*, Immunochemistry 1976, vol. 13, 813–819. For an example of a study involving the binding of a polymyxin derivative to Gram-negative bacteria see: M. Vaara and P. Viljanen, *Binding of Polymyxin B Nonapeptide to Gram-negative Bacteria*, Antimicrobial Agents and Chemotherapy, 1985, vol. 27, 548–554.

Membranes of Gram-negative bacteria are semipermeable molecular "sieves" which restrict access of antibiotics and host defense molecules to their targets within the bacterial cell. Thus, cations and polycations which interact with and break down the outer membrane permeability barrier are capable of increasing the susceptibility of Gram-negative pathogenic bacteria to antibiotics and host defense molecules. Hancock and Wong demonstrated that a broad range of peptides could overcome the permeability barrier and coined the name "permeabilizers" to describe them (Hancock and Wong, *Antimicrob. Agents Chemother.*, 26:48, 1984).

SUMMARY OF THE INVENTION

The present invention features compounds of the formula I

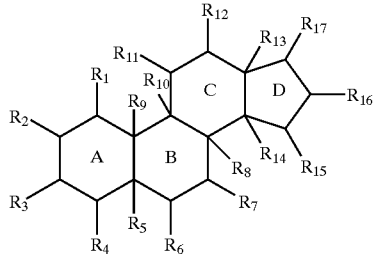

wherein:
fused rings A, B, C, and D are independently saturated or fully or partially unsaturated; and
each of $R_1$ through $R_4$, $R_6$, $R_7$, $R_{11}$, $R_{12}$, $R_{15}$, $R_{16}$, and $R_{17}$ is independently selected from the group consisting of hydrogen, hydroxyl, a substituted or unsubstituted (C1–C10)alkyl, (C1–C10) hydroxyalkyl, (C1–C10) alkyloxy-(C1–C10) alkyl, (C1–C10) alkylcarboxy-(C1–C10) alkyl, (C1–C10) alkylamino-(C1–C10) alkyl, (C1–C10) alkylamino-(C1–C10) alkylamino, (C1–C10) alkylamino-(C1–C10) alkylamino-(C1–C10) alkylamino, a substituted or unsubstituted (C1–C10) aminoalkyl, a substituted or unsubstituted aryl, a substituted or unsubstituted arylamino-(C1–C10) alkyl, (C1–C10) haloalkyl, C2–C6 alkenyl, C2–C6 alkynyl, oxo, a linking group attached to a second steroid, a substituted or unsubstituted (C1–C10) aminoalkyloxy, a substituted or unsubstituted (C1–C10) aminoalkyloxy-(C1–C10) alkyl, a substituted or unsubstituted (C1–C10) aminoalkylcarboxy, a substituted or unsubstituted (C1–C10) aminoalkylaminocarbonyl, a substituted or unsubstituted (C1–C10) aminoalkylcarboxamido, H2N—HC(Q5)—C(O)—O—, H2N—HC(Q5)—C(O)—N(H)—, (C1–C10) azidoalkyloxy, (C1–C10) cyanoalkyloxy, P.G.-HN—HC(Q5)—C(O)—O—, (C1–C10) guanidinoalkyl oxy, (C1–C10) quaternaryammonium-alkylcarboxy, and (C1–C10) guanidinoalkyl carboxy, where Q5 is a side chain of any amino acid (including the side chain of glycine, i.e., H), P.G. is an amino protecting group, and
$R_5$, $R_8$, $R_9$, $R_{10}$, $R_{13}$, and $R_{14}$ is each independently: deleted when one of fused rings A, B, C, or D is unsaturated so as to complete the valency of the carbon atom at that site, or
selected from the group consisting of hydrogen, hydroxyl, a substituted or unsubstituted (C1–C10) alkyl, (C1–C10) hydroxyalkyl, (C1–C10) alkyloxy-(C1–C10) alkyl, a substituted or unsubstituted (C1–C10) aminoalkyl, a substituted or unsubstituted aryl, C1–C10 haloalkyl, C2–C6 alkenyl, C2–C6 alkynyl, a linking group attached to a second steroid, a substituted or unsubstituted (C1–C10) aminoalkyloxy, a substituted or unsubstituted (C1–C10) aminoalkylcarboxy, a substituted or unsubstituted (C1–C10) aminoalkylaminocarbonyl, H2N—HC(Q5)—C(O)—O—, H2N—HC(Q5)—C(O)—N(H)—, (C1–C10) azidoalkyloxy, (C1–C10) cyanoalkyloxy, P.G.-HN—HC(Q5)—C(O)—O—, (C1–C10) guanidinoalkyloxy, and (C1–C10)

guanidinoalkylcarboxy, where Q5 is a side chain of any amino acid, P.G. is an amino protecting group, and provided that at least two of $R_1$ through $R_{14}$ are independently selected from the group consisting of a substituted or unsubstituted (C1–C10) aminoalkyloxy, (C1–C10) alkylcarboxy-(C1–C10) alkyl, (C1–C10) alkylamino-(C1–C10) alkylamino, (C1–C10) alkylamino-(C1–C10) alkylamino-(C1–C10) alkylamino, a substituted or unsubstituted (C1–C10) aminoalkylcarboxy, a substituted or unsubstituted arylamino-(C1–C10) alkyl, a substituted or unsubstituted (C1–C10) aminoalkyloxy-(C1–C10) alkyl, a substituted or unsubstituted (C1–C10) aminoalkylaminocarbonyl, (C1–C10) quaternaryammonium alkylcarboxy, H2N—HC(Q5)—C(O)—O—, H2N—HC(Q5)—C(O)—N(H)—, (C1–C10) azidoalkyloxy, (C1–C10) cyanoalkyloxy, P.G.-HN—HC(Q5)—C(O)—O—, (C1–C10) guanidinoalkyloxy, and (C1–C10) guanidinoalkylcarboxy; or a pharmaceutically acceptable salt thereof.

The term fused ring used herein can be heterocyclic or carbocyclic, preferably.

The term "saturated" used herein refers to the fused ring of formula I having each atom in the fused ring either hydrogenated or substituted such that the valency of each atom is filled.

The term "unsaturated" used herein refers to the fused ring of formula I where the valency of each atom of the fused ring may not be filled with hydrogen or other substituents. For example, adjacent carbon atoms in the fused ring can be doubly bound to each other. Unsaturation can also include deleting at least one of the following pairs and completing the valency of the ring carbon atoms at these deleted positions with a double bond; such as $R_5$ and $R_9$; $R_8$ and $R_{10}$; and $R_{13}$ and $R_{14}$.

The term "unsubstituted" used herein refers to a moiety having each atom hydrogenated such that the valency of each atom is filled.

The term "halo" used herein refers to a halogen atom such as fluorine, chlorine, bromine, or iodine.

Examples of amino acid side chains include but are not limited to H (glycine), methyl (alanine), —CH₂—(C=O)—NH₂ (asparagine), —CH₂—SH (cysteine), and —CH(OH)CH₃ (threonine).

An alkyl group is a branched or unbranched hydrocarbon that may be substituted or unsubstituted. Examples of branched alkyl groups include isopropyl, sec-butyl, isobutyl, tert-butyl, sec-pentyl, isopentyl, tert-pentyl, isohexyl. Substituted alkyl groups may have one, two, three or more substituents, which may be the same or different, each replacing a hydrogen atom. Substituents are halogen (e.g., F, Cl, Br, and I), hydroxyl, protected hydroxyl, amino, protected amino, carboxy, protected carboxy, cyano, methylsulfonylamino, alkoxy, acyloxy, nitro, and lower haloalkyl.

The term "substitued" used herein refers to moieties having one, two, three or more substituents, which may be the same or different, each replacing a hydrogen atom. Examples of substituents include but are not limited to halogen (e.g., F, Cl, Br, and I), hydroxyl, protected hydroxyl, amino, protected amino, carboxy, protected carboxy, cyano, methylsulfonylamino, alkoxy, alkyl, aryl, aralkyl, acyloxy, nitro, and lower haloalkyl.

An aryl group is a $C_{6-20}$ aromatic ring, wherein the ring is made of carbon atoms (e.g., $C_{6-14}$, $C_{6-10}$ aryl groups). Examples of haloalkyl include fluoromethyl, dichloromethyl, trifluoromethyl, 1,1-difluoroethyl, and 2,2-dibromoethyl.

An aralkyl group is a group containing 6–20 carbon atoms that has at least one aryl ring and at least one alkyl or alkylene chain connected to that ring. An example of an aralkyl group is a benzyl group.

A linking group is any divalent moiety used to link a compound of formula to another steroid, e.g., a second compound of formula I. An example of a linking group is (C1–C10) alkyloxy-(C1–C10) alkyl.

Numerous amino-protecting groups are well-known to those in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the invention. Further examples and conditions are found in T. W. Greene, *Protective Groups in Organic Chemistry*, (1st ed., 1981, 2nd ed., 1991).

The present invention also includes methods of synthesizing compounds of formula I where at least two of $R_1$ through $R_{14}$ are independently selected from the group consisting of a substituted or unsubstituted (C1–C10) aminoalkyloxy. The method includes the step of contacting a compound of formula IV,

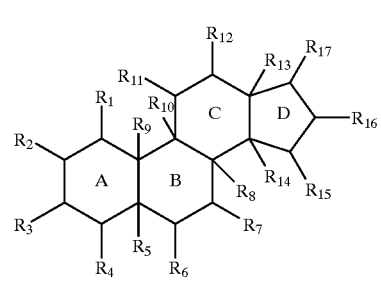

IV where at least two of $R_1$ through $R_{14}$ are hydroxyl, and the remaining moieties on the fused rings A, B, C, and D are defined for formula I, with an electrophile to produce an alkyl ether compound of formula IV, wherein at least two of $R_1$ through $R_{14}$ are (C1–C10) alkyloxy. The alkyl ether compounds are converted into an amino precursor compound wherein at least two of $R_1$ through $R_{14}$ are independently selected from the group consisting of (C1–C10) azidoalkyloxy and (C1–C10) cyanoalkyloxy and the amino precursor compound is reduced to form a compound of formula I.

The electrophiles used in the method include but are not limited to 2-(2-bromoethyl)-1,3-dioxolane, 2-iodoacetamide, 2-chloroacetamide, N-(2-bromoethyl) phthalimide, N-(3-bromopropyl)phthalimide, and allybromide. The preferred electrophile is allylbromide.

The invention also includes a method of producing a compound of formula I where at least two of $R_1$ through $R_{14}$ are (C1–C10) guanidoalkyloxy. The method includes contacting a compound of formula IV, where at least two of $R_1$ through $R_{14}$ are hydroxyl, with an electrophile to produce an alkyl ether compound of formula IV, where at least two of $R_1$ through $R_{14}$ are (C1–C10)alkyloxy. The allyl ether compound is converted into an amino precursor compound where at least two of $R_1$ through $R_{14}$ are independently selected from the group consisting of (C1–C10) azidoalkyloxy and (C1–C10) cyanoalkyloxy. The amino precursor compound is reduced to produce an aminoalkyl ether compound wherein at least two of $R_1$ through $R_{14}$ are (C1–C10) aminoalkyloxy. The aminoalkyl ether compound is contacted with a guanidino producing electrophile to form a compound of formula I.

The term "guanidino producing electrophile" used herein refers to an electrophile used to produce a guanidino compound of formula I. An example of an guanidino producing electrophile is $HSO_3$—C(NH)—$NH_2$.

The invention also includes a method of producing a compound of formula I where at least two of $R_1$ through $R_{14}$ are H2N—HC(Q5)—C(O)—O— and Q5 is the side chain of any amino acid. The method includes the step of contacting a compound of formula IV, where at least two of $R_1$ through $R_{14}$ are hydroxyl, with a protected amino acid to produce a protected amino acid compound of formula IV where at least two of at least two of $R_1$ through $R_{14}$ are P.G.-HN—HC(Q5)—C(O)—O— and Q5 is the side chain of any amino acid and P.G. is an amino protecting group. The protecting group of the protected amino acid compound is removed to form a compound of formula I.

The present invention also includes pharmaceutical compositions of matter that are useful as antibacterial agents, sensitizers of bacteria to other antibiotics and disrupters of bacterial membranes. The pharmaceutical compositions can be used to treat humans and animals having a bacterial infection. The pharmaceutical compositions can include an effective amount of the steroid derivative alone or in combination with other antibacterial agents.

The invention further includes a method of preparing the compound (A):

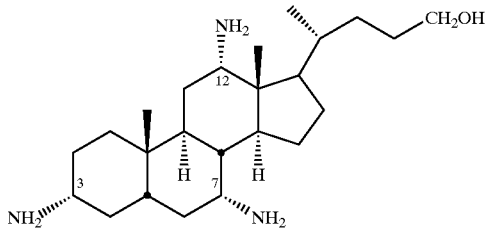

by
(a) contacting 5β-cholanic acid 3,7,12-trione methyl ester with hydroxyl amine hydrochloride and sodium acetate to form the trioxime (B):

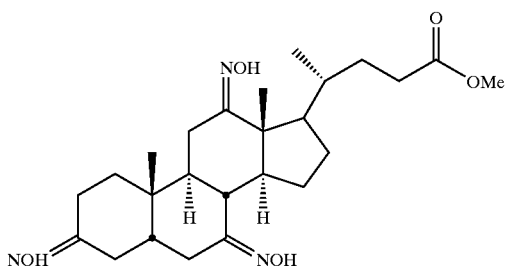

and
(b) contacting trioxime (B) with $NaBH_4$ and $TiCl_4$ to yield compound (A).

The invention also includes a compound comprising a ring system of at least 4 fused rings, where each of the rings has from 5–7 atoms. The ring system has two faces, and contains 3 chains attached to the same face. Each of the chains contains a nitrogen-containing group that is separated from the ring system by at least one atom; the nitrogen-containing group is an amino group, e.g., a primary amino group, or a guanidino group. Preferably, the compound also contains a hydrophobic group, such as a substituted (C3–10) aminoalkyl group, a (C1–10) alkyloxy (C3–10) alkyl group, or a (C1–10) alkylamino (C3–10)alkyl group, attached to the steroid backbone.

For example, the compound may have the formula V, where each of the three chains containing nitrogen-containing groups is independently selected from $R_1$ through $R_4$, $R_6$, $R_7$, $R_{11}$, $R_{12}$, $R_{15}$, $R_{16}$, $R_{17}$, and $R_{18}$, defined below.

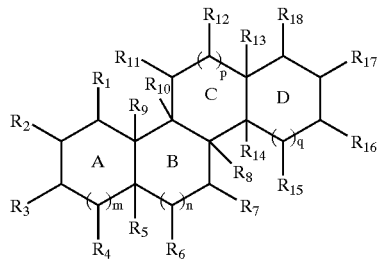

V where:
each of fused rings A, B, C, and D is independently saturated, or is fully or partially unsaturated, provided that at least two of A, B, C, and D are saturated, wherein rings A, B, C, and D form a ring system;

each of m, n, p, and q is independently 0 or 1;

each of $R_1$ through $R_4$, $R_6$, $R_7$, $R_{11}$, $R_{12}$, $R_{15}$, $R_{16}$, $R_{17}$, and $R_{18}$ is independently selected from the group consisting of hydrogen, hydroxyl, a substituted or unsubstituted (C1–C10) alkyl, (C1–C10) hydroxyalkyl, (C1–C10) alkyloxy-(C1–C10) alkyl, (C1–C10) alkylcarboxy-(C1–C10) alkyl, (C1–C10) alkylamino-(C1–C10) alkyl, (C1–C10) alkylamino-(C1–C10) alkylamino, (C1–C10) alkylamino-(C1–C10) alkylamino-(C1–C10) alkylamino, a substituted or unsubstituted (C1–C10) aminoalkyl, a substituted or unsubstituted aryl, a substituted or unsubstituted arylamino-(C1–C10) alkyl, (C1–C10) haloalkyl, C2–C6 alkenyl, C2–C6 alkynyl, oxo, a linking group attached to a second steroid, a substituted or unsubstituted (C1–C10) aminoalkyloxy, a substituted or unsubstituted (C1–C10) aminoalkyloxy-(C1–C10) alkyl, a substituted or unsubstituted (C1–C10) aminoalkylcarboxy, a substituted or unsubstituted (C1–C10) aminoalkylaminocarbonyl, a substituted or unsubstituted (C1–C10) aminoalkylcarboxamido, H2N—HC(Q5)—C(O)—O—, H2N—HC(Q5)—C(O)—N(H)—, (C1–C10) azidoalkyloxy, (C1–C10) cyanoalkyloxy, P.G.-HN—HC(Q5)—C(O)—O—, (C1–C10) guanidinoalkyl oxy, (C1–C10) quaternaryammoniumalkylcarboxy, and (C1–10) guanidinoalkyl carboxy, where Q5 is a side chain of any amino acid (including the side chain of glycine, i.e., H), P.G. is an amino protecting group; and each of $R_5$, $R_8$, $R_9$, $R_{10}$, $R_{13}$, and $R_{14}$ is independently: deleted when one of fused rings A, B, C, or D is unsaturated so as to complete the valency of the carbon atom at that site, or selected from the group consisting of hydrogen, hydroxyl, a substituted or unsubstituted (C1–C10) alkyl, (C1–C10) hydroxyalkyl, (C1–C10)

alkyloxy-(C1–C10) alkyl, a substituted or unsubstituted (C1–C10) aminoalkyl, a substituted or unsubstituted aryl, C1–C10 haloalkyl, C2–C6 alkenyl, C2–C6 alkynyl, a linking group attached to a second steroid, a substituted or unsubstituted (C1–C10) aminoalkyloxy, a substituted or unsubstituted (C1–C10) aminoalkylcarboxy, a substituted or unsubstituted (C1–C10) aminoalkylaminocarbonyl, H2N—HC(Q5)—C(O)—O—, H2N—HC(Q5)—C(O)—N(H)—, (C1–C10) azidoalkyloxy, (C1–C10) cyanoalkyloxy, P.G.-HN—HC(Q5)—C(O)—O—, (C1–C10) guanidinoalkyloxy, and (C1–C10) guanidinoalkylcarboxy, where Q5 is a side chain of any amino acid, P.G. is an amino protecting group, provided that at least three of $R_1$ through $R_4$, $R_6$, $R_7$, $R_{11}$, $R_{12}$, $R_{15}$, $R_{16}$, $R_{17}$, and $R_{18}$ are disposed on the same face of the ring system and are independently selected from the group consisting of a substituted or unsubstituted (C1–C10) aminoalkyloxy, (C1–C10) alkylcarboxy-(C1–C10) alkyl, (C1–C10) alkylamino-(C1–C10) alkylamino, (C1–C10) alkylamino-(C1–C10) alkylamino-(C1–C10) alkylamino, a substituted or unsubstituted (C1–C10) aminoalkylcarboxy, a substituted or unsubstituted arylamino-(C1–C10) alkyl, a substituted or unsubstituted (C1–C10) aminoalkyloxy-(C1–C10) alkyl, a substituted or unsubstituted (C1–C10) aminoalkylaminocarbonyl, (C1–C10) quaternaryammoniumalkylcarboxy, H2N—HC(Q5)—C(O)—O—, H2N—HC(Q5)—C(O)—N(H)—, (C1–C10) azidoalkyloxy, (C1–C10) cyanoalkyloxy, P.G.-HN—HC(Q5)—C(O)—O—, (C1–C10) guanidinoalkyloxy, and (C1–C10) guanidinoalkylcarboxy; or a pharmaceutically acceptable salt thereof. Preferably, at least two, or at least, three, of m, n, p, and q are 1.

Without wishing to be bound to any particular theory, the steroid derivatives described herein act as bacteriostatic and bactericidal agents by binding to the outer cellular membrane of bacteria. The interaction between the steroid derivatives and the bacteria membrane disrupts the integrity of the cellular membrane and results in the death of the bacteria cell. In addition, compounds of the present invention also act to sensitize bacteria to other antibiotics. At concentrations of the steroid derivatives below the corresponding minimum bacteriostatic concentration, the derivatives cause bacteria to become more susceptible to other antibiotics by increasing the permeability of the outer membrane of the bacteria. Measurements used to quantitate the effects of the steroid derivatives on bacteria include: measurement of minimum inhibitory concentrations (MICs), measurement of minimum bactericidal concentrations (MBCs) and the ability of the steroid derivatives to lower the MICs of other antibiotics, e.g., erythromycin and novobiocin.

A person of skill will recognize that the compounds described herein preserve certain stereochemical and electronic characteristics found in steroids. The term "same configuration" as used herein refers to substituents on the fused steroid having the same stereochemical orientation. For example substituents R3, R7 and R12 are all β-substituted or α-substituted. The configuration of the moieties R3, R7, and R12 substituted on C3, C7, and C12 may be important for interaction with the cellular membrane.

In another aspect, the invention features several methods of using the above-described compounds. For example, an effective amount of an anti-microbial composition comprising such a compound is administered to a host (including a human host) to treat a microbial infection. The compound by itself may provide the anti-microbial effect, in which case the amount of the compound administered is sufficient to be anti-microbial. Alternatively, an additional anti-microbial substance to be delivered to the microbial cells (e.g., an antibiotic) is included in the anti-microbial composition. By facilitating delivery to the target cells, the compounds can enhance the effectiveness of the additional antimicrobial substance. In some cases the enhancement may be substantial. Particularly important target microbes are bacteria (e.g., Gram-negative bacteria generally or bacteria which have a substantial (>40%) amount of a lipid A or lipid A-like substance in the outer membrane). Other microbes including fungi, viruses, and yeast may also be the target organisms.

The compounds can also be administered in other contexts to enhance cell permeability to introduce any of a large number of different kinds of substances into a cell, particularly the bacterial cells discussed above. In addition to introducing anti-microbial substances, the invention may be used to introduce other substances such as macromolecules (e.g., vector-less DNA).

The invention can also be used to make anti-microbial compositions (e.g., disinfectants, antiseptics, antibiotics etc.) which comprise one of the above compounds. These compositions are not limited to pharmaceuticals, and they may be used topically or in non-therapeutic contexts to control microbial (particularly bacterial) growth. For example, they may be used in applications that kill or control microbes on contact.

In yet another aspect, the invention generally features methods of identifying compounds that are effective against a microbe by administering a candidate compound and a compound according to the invention the microbe and determining whether the candidate compound has a static or toxic effect (e.g, an antiseptic, germicidal, disinfectant, or antibiotic effect) on the microbe. Again, bacteria such as those discussed above are preferred. This aspect of the invention permits useful testing of an extremely broad range of candidate anti-microbials which are known to have anti-microbial effect in some contexts, but which have not yet been shown to have any effect against certain classes of microbes such as the bacteria discussed above. As described in greater detail below, this aspect of the invention permits testing of a broad range of antibiotics currently thought to be ineffective against Gram-negative or lipid A-like containing bacteria.

In yet another aspect the invention features compositions which include one of the above compounds in combination with a substance to be introduced into a cell such as an antimicrobial substance as described in greater detail above. The compound and the additional substance may be mixed with a pharmaceutically acceptable carrier.

Other features or advantages of the present invention will be apparent from the following detailed description of several embodiments, and also from the appending claims.

The invention encompasses steroid derivatives that can be made by the synthetic routes described herein, and methods of treating a subject having a condition mediated by a bacterial infection by administering an effective amount of a pharmaceutical composition containing a compound disclosed herein to the subject.

DETAILED DESCRIPTION

Figure 1:
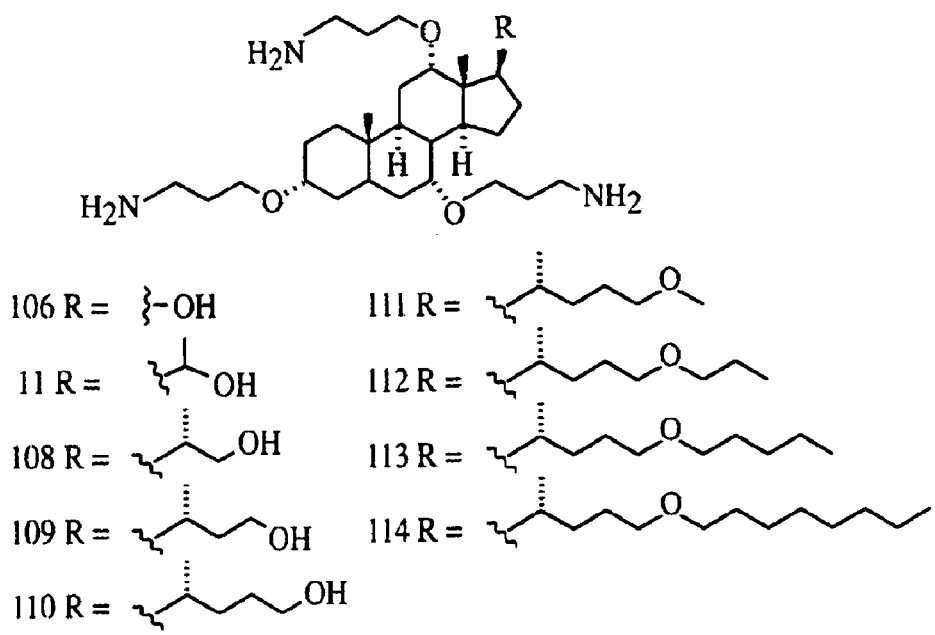
FIG. 1 is a drawing showing compounds of the invention.

In general, the present invention provides the compounds of formula I described above. The preparation methods and the MIC and MBC of compounds of formula I are described. The cellular membrane permeability is also measured and described. Compounds that are useful in accordance with the invention, as described below, include novel steroid derivatives that exhibit bacteriostatic, bactericidal, and bacterial sensitizer properties. Those skilled in the art will appreciate that the invention extends to other compounds within the formulae given in the claims below, having the described characteristics. These characteristics can be determined for each test compound using the assays detailed below and elsewhere in the literature.

Known compounds that are used in accordance with the invention and precursors to novel compounds according to the invention can be purchased, e.g., from Sigma Chemical Co., St. Louis; Aldrich, Milwaukee; Steroids and Research Plus. Other compounds according to the invention can be synthesized according to known methods and the methods described below using publicly available precursors.

The compounds of the present invention include but are not limited to compounds having amine or guanidine groups covalently tethered to a steroid backbone, e.g., cholic acid. Other ring systems can also be used, e.g., 5-member fused rings. Compounds with backbones having a combination of 5- and 6-membered rings are also included in the invention. The amine or guanidine groups are separated from the backbone by at least one atom, and preferably are separated by at least two, three, or four atoms. The backbone can be used to orient the amine or guanidine groups on one face, or plane, of the steroid. For example, a scheme showing a compound having primary amino groups on one face, or plane, of a backbone is shown below:

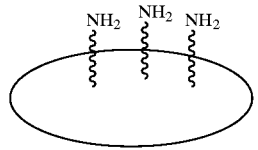

The biological activity of the compounds can be determined by standard methods known to those of skill in the art, such as the "minimal inhibitory concentration (MIC)" assay described in the present examples, whereby the lowest concentration at which no change in optical density (OD) is observed for a given period of time is recorded as MIC. When the compound alone is tested against a control that lacks the compound, the antimicrobial effect of the compound alone is determined.

Alternatively, "fractional inhibitory concentration (FIC)" is also useful for determination of synergy between the compounds of the invention, or the compounds in combination with known antibiotics. FICs can be performed by checkerboard titrations of compounds in one dimension of a microtiter plate, and of antibiotics in the other dimension, for example. The FIC is calculated by looking at the impact of one antibiotic on the MIC of the other and vice versa. An FIC of one indicates that the influence of the compounds is additive and an FIC of less than one indicates synergy. Preferably, an FIC of less than 0.5 is obtained for synergism. As used herein, FIC can be determined as follows:

$$FIC = \frac{MIC \text{ (compound in combination)}}{MIC \text{ (compound alone)}} + \frac{MIC \text{ (antibiotic in combination)}}{MIC \text{ (antibiotic alone)}}$$

This procedure permits determination of synergistic effects of the compound with other compounds. For example, substances that generally may not be sufficiently effective against certain bacteria at safe dosages can be made more effective with the compound of the invention, thus enabling use of the substances against new categories of infections. Specifically, many existing antibiotics are effective against some Gram-positive bacteria, but are not currently indicated to treat Gram-negative bacterial infection. In some cases, the antibiotic may be ineffective by itself against Gram-negative bacteria because it fails to enter the cell. Compounds of the invention may increase permeability so as to render the antibiotics effective against Gram-negative bacteria.

In addition, fractional inhibitory concentration is also useful for determination of synergy between compounds of the invention in combination with other compounds having unknown anti-bacterial activity or in combination with other compounds, e.g., compounds which have been tested and show anti-bacterial activity. For example, compounds of the invention may increase permeability so as to render compounds lacking anti-bacterial activity effective against bacteria. The FIC can also be used to test for other types of previously unappreciated activity of substances that will be introduced into the cell by means of permeability enhancing compounds according to the invention.

While we do not wish to be bound to any single specific theory, and such a theory is not necessary to practice the invention, one mechanism of action is the lipid A interaction of multiple (usually three) moieties, which under physiological conditions are positively charged, e.g., guanidino or amino moieties. The moieties extend away from the general plane of the remainder of the molecule, thus mimicking certain aspects of the structure of polymyxins. In this regard, compounds of the invention will generally be useful in the way that polymyxins are useful. For example, polymyxin B (PMB) and polymyxin B nonapeptide (PMBN) are useful for permeabilizing bacterial membranes. Moreover, in regard to systemic administration, those skilled in the art will recognize appropriate toxicity screens that permit selection of compounds that are not toxic at dosages that enhance microbial permeability.

As noted, the invention also involves topical as well as non-therapeutic (antiseptic, germicidal, or disinfecting) applications in which the compounds are contacted with surfaces to be treated. The term "contacting" preferably refers to exposing the bacteria to the compound so that the compound can effectively inhibit, kill, or lyse bacteria, bind endotoxin (LPS), or permeabilize Gram-negative bacterial outer membranes. Contacting may be in vitro, for example by adding the compound to a bacterial culture to test for susceptibility of the bacteria to the compound. Contacting may be in vivo, for example administering the compound to a subject with a bacterial disorder, such as septic shock. "Inhibiting" or "inhibiting effective amount" refers to the amount of compound which is required to cause a bacteriostatic or bactericidal effect. Examples of bacteria which may be inhibited include E. coli, P. aeruginosa, E. cloacae, S. typhimurium, M. tuberculosis and S. aureus. In addition, the compounds of the invention can be used to inhibit antibiotic-resistant strains of microorganisms.

The method of inhibiting the growth of bacteria may further include the addition of antibiotics for combination or synergistic therapy. The appropriate antibiotic administered will typically depend on the susceptibility of the bacteria such as whether the bacteria is Gram-negative or Gram-positive, and will be easily discernable by one of skill in the art. Examples of particular classes of antibiotics to be tested for synergistic therapy with the compounds of the invention (as described above) include aminoglycosides (e.g., tobramycin), penicillins (e.g., piperacillin), cephalosporins (e.g., ceftazidime), fluoroquinolones (e.g., ciprofloxacin), carbepenems (e.g., imipenem), tetracyclines and macrolides (e.g., erythromycin and clarithromycin). The method of inhibiting the growth of bacteria may further include the addition of antibiotics for combination or synergistic therapy. The appropriate antibiotic administered will typically depend on the susceptibility of the bacteria such as whether the bacteria is Gram-negative or Gram-positive, and will be easily discernable by one of skill in the art. Further to the antibiotics listed above, typical antibiotics include aminoglycosides (amikacin, gentamicin, kanamycin, netilmicin, tobramycin, streptomycin, azithromycin, clarithromycin, erythromycin, erythromycin estolate/ethylsuccinate, gluceptate/lactobionate/stearate, beta-lactams such as penicillins (e.g., penicillin G, penicillin V, methicillin, nafcillin, oxacillin, cloxacillin, dicloxacillin, ampicillin, amoxicillin, ticarcillin, carbenicillin, mezlocillin, azlocillin and piperacillin), or cephalosporins (e.g., cephalothin, cefazolin, cefaclor, cefamandole, cefoxitin, cefuroxime, cefonicid, cefmetazole, cefotetan, cefprozil, loracarbef, cefetamet, cefoperazone, cefotaxime, ceftizoxime, ceftriaxone, ceftazidime, cefepime, cefixime, cefpodoxime, and cefsulodin). Other classes of antibiotics include carbapenems (e.g., imipenem), monobactams (e.g., aztreonam), quinolones (e.g., fleroxacin, nalidixic acid, norfloxacin, ciprofloxacin, ofloxacin, enoxacin, lomefloxacin and cinoxacin), tetracyclines (e.g., doxycycline, minocycline, tetracycline), and glycopeptides (e.g., vancomycin, teicoplanin), for example. Other antibiotics include chloramphenicol, clindamycin, trimethoprim, sulfamethoxazole, nitrofurantoin, rifampin and mupirocin, and polymyxins, such as PMB.

Administration

The compounds may be administered to any host, including a human or non-human animal, in an amount effective to inhibit not only growth of a bacterium, but also a virus or fungus. These compounds are useful as antimicrobial agents, antiviral agents, and antifungal agents. The compounds may be administered to any host, including a human or non-human animal, in an amount effective to inhibit not only growth of a bacterium, but also a virus or fungus. These compounds are useful as antimicrobial agents, antiviral agents, and antifungal agents.

The compounds of the invention can be administered parenterally by injection or by gradual infusion over time. The compounds can be administered topically, intravenously, intraperitoneally, intramuscularly, subcutaneously, intracavity, or transdermally. Preferred methods for delivery of the compound include orally, by encapsulation in microspheres or proteinoids, by aerosol delivery to the lungs, or transdermally by iontophoresis or transdermal electroporation. Other methods of administration will be known to those skilled in the art.

Preparations for parenteral administration of a compound of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention provides a method of treating or ameliorating an endotoxemia or septic shock (sepsis) associated disorder, or one or more of the symptoms of sepsis comprising administering to a subject displaying symptoms of sepsis or at risk for developing sepsis, a therapeutically effective amount of a compound of the invention. The term "ameliorate" refers to a decrease or lessening of the symptoms of the disorder being treated. Such symptoms which may be ameliorated include those associated with a transient increase in the blood level of TNF, such as fever, hypotension, neutropenia, leukopenia, thrombocytopenia, disseminated intravascular coagulation, adult respiratory distress syndrome, shock and multiple organ failure. Patients who require such treatment include those at risk for or those suffering from toxemia, such as endotoxemia resulting from a Gram-negative bacterial infection, venom poisoning, or hepatic failure, for example. In addition, patients having a Gram-positive bacterial, viral or fungal infection may display symptoms of sepsis and may benefit from such a therapeutic method as described herein. Those patients who are more particularly able to benefit from the method of the invention are those suffering from infection by E. coli, Haemophilus influenza B, Neisseria meningitidis, staphylococci, or pneumococci. Patients at risk for sepsis include those suffering from gunshot wounds, renal or hepatic failure, trauma, burns, immunocompromised (HIV), hematopoietic neoplasias, multiple myeloma, Castleman's disease or cardiac myxoma.

In addition, the compounds may be incorporated into biodegradable polymers allowing for sustained release, the polymers being implanted in the vicinity of where delivery is desired, for example, at the site of a bacterial infection. The biodegradable polymers and their use are described in detail in Brem et al., J. Neurosurg, 74:441–446 (1991).

As mentioned above, the present invention provides a pharmaceutical formulation having an effective amount of a compound of formula I for treating a patient having a bacterial infection. As used herein, an effective amount of the compound is defined as the amount of the compound which, upon administration to a patient, inhibits growth of bacteria, kills bacteria cells, sensitizes bacteria to other antibiotics, or eliminates the bacterial infection entirely in the treated patient. The dosage of the composition will depend on the condition being treated, the particular derivative used, and other clinical factors such as weight and condition of the patient and the route of administration of the compound. However, for oral administration to humans, a dosage of 0.01 to 100 mg/kg/day, preferably 0.01–1 mg/kg/day, is generally sufficient. Effective doses will also vary, as recognized by those skilled in the art, dependent on route of administration, excipient usage, and the possibility of co-usage with other therapeutic treatments including other antibiotic agents.

For example, the term "therapeutically effective amount" as used herein for treatment of endotoxemia refers to the amount of compound used is of sufficient quantity to decrease the subject's response to LPS and decrease the symptoms of sepsis. The term "therapeutically effective" therefore includes that the amount of compound sufficient to prevent, and preferably reduce by at least 50%, and more preferably sufficient to reduce by 90%, a clinically significant increase in the plasma level of TNF. The dosage ranges for the administration of compound are those large enough to produce the desired effect. Generally, the dosage will vary with the age, condition, sex, and extent of the infection with bacteria or other agent as described above, in the patient and can be determined by one skilled in the art. The dosage can be adjusted by the individual physician in the event of any contraindications. In any event, the effectiveness of treatment can be determined by monitoring the level of LPS and TNF in a patient. A decrease in serum LPS and TNF levels should correlate with recovery of the patient.

In addition, patients at risk for or exhibiting the symptoms of sepsis can be treated by the method as described above, further comprising administering, substantially simultaneously with the therapeutic administration of compound, an inhibitor of TNF, an antibiotic, or both. For example, intervention in the role of TNF in sepsis, either directly or indirectly, such as by use of an anti-TNF antibody and/or a TNF antagonist, can prevent or ameliorate the symptoms of sepsis. Particularly preferred is the use of an anti-TNF antibody as an active ingredient, such as a monoclonal antibody with TNF specificity as described by Tracey, et al. (*Nature*, 330:662, 1987).

A patient who exhibits the symptoms of sepsis may be treated with antibiotic in addition to the treatment with compound. Typical antibiotics include an aminoglycoside, such as gentamicin or a beta-lactam such as penicillin, or cephalosporin or any of the antibiotics as previously listed above. Therefore, a preferred therapeutic method of the invention includes administering a therapeutically effective amount of cationic compound substantially simultaneously with administration of a bactericidal amount of an antibiotic. Preferably, administration of compound occurs within about 48 hours and preferably within about 2–8 hours, and most preferably, substantially concurrently with administration of the antibiotic.

The term "bactericidal amount" as used herein refers to an amount sufficient to achieve a bacteria-killing blood concentration in the patient receiving the treatment. The bactericidal amount of antibiotic generally recognized as safe for administration to a human is well known in the art, and as is known in the art, varies with the specific antibiotic and the type of bacterial infection being treated.

Because of the antibiotic, antimicrobial, and antiviral properties of the compounds, they may also be used as preservatives or sterilants of materials susceptible to microbial or viral contamination. The compounds of the invention can be utilized as broad-spectrum antimicrobial agents directed toward various specific applications. Such applications include use of the compounds as preservatives in processed foods when verified as effective against organisms including Salmonella, Yersinia, Shigella, either alone or in combination with antibacterial food additives such as lysozymes; as a topical agent (Pseudomonas, Streptococcus) and to kill odor producing microbes (Micrococci). The relative effectiveness of the compounds of the invention for the applications described can be readily determined by one of skill in the art by determining the sensitivity of any organism to one of the compounds.

While primarily targeted at classical Gram-negative-staining bacteria whose outer capsule contains a substantial amount of lipid A, it may also be effective against other organisms with a hydrophobic outer capsule. For example, Mycobacterium spp. have a waxy protective outer coating, and compounds of the invention in combination with antibiotics may provide enhanced effectiveness against Mycobacterial infection, including tuberculosis. In that case, the compounds could be administered nasally (aspiration), by any of several known techniques.

Apart from anti-microbial action, the permeability provided by the compounds may enhance introduction of a great variety of substances into microbes. For example, the compounds may be used to enhance introduction of macromolecules such as DNA or RNA into microbes, particularly Gram-negative bacteria. In that case, there may be no need for the traditional vectors (e.g., phages) used to package nucleic acids when transfecting the microbes. Conditions and techniques for introducing such macromolecules into microbes using the compounds of the invention will in most cases be routine.

The formulations include those suitable for oral, rectal, nasal, topical (including buccal and sublingual), vaginal or parenteral (including subcutaneous, intramuscular, intravenous, intradermal, intraocular, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tablets may be made by molding, in a suitable machine, a mixture of the powdered compound moistened with an inert liquid diluent. The tablets may optionally be coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such as carriers as are known in the art to be appropriate.

Formulations suitable for parenteral administration include aqueous and non-aqueous sterile injection solutions which may contain anti-oxidants, buffers, other bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tables of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of this invention may include other agents conventional in the art having regard to the type of formulation in question, for example, those suitable for oral administration may include flavoring agents.

The carrier in the pharmaceutical composition must be "acceptable" in the sense of being compatible with the active ingredient of the formulation (and preferably, capable of stabilizing it) and not deleterious to the subject to be treated.

Without further elaboration, it is believed that the above description has adequately enabled the present invention. The following specific embodiments are, therefore, to be construed as merely illustrative, and not limitative of the remainder of the disclosure in any way whatsoever. All of the publications cited herein, including patents, are hereby incorporated by reference.

Examples 1–14 represent typical syntheses of compounds 1 through 343, some of which are shown in Schemes 1 through 16. Example 14 shows stability of compounds 352–354 under acidic, neutral and basic conditions. Example 15 represents other compounds of formula I which can be synthesized using known starting materials and reaction schemes that are similar to those described herein. For example, the hydroxyl groups on cholic acid can be converted into amine groups by the method found in Hsieh et al., Synthesis and DNA Binding Properties of C3-, C12-, and C24-Substituted Amino-Steroids Derived from Bile Acids, *Biorganic and Medicinal Chemistry*, 1995, vol. 6, 823–838. Example 16 represents MIC and MCB testing, and Example 17 represents the ability of the compounds of formula I to lower the MIC's of other antibiotics.

Scheme 1. Preparation of compounds 1, 2, 4 and 5.

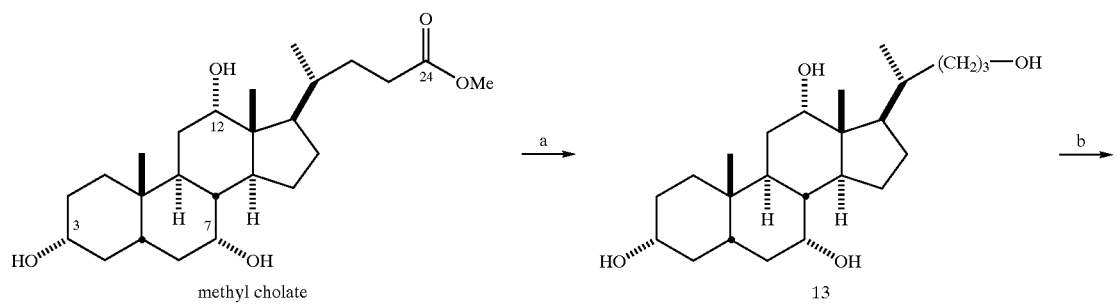

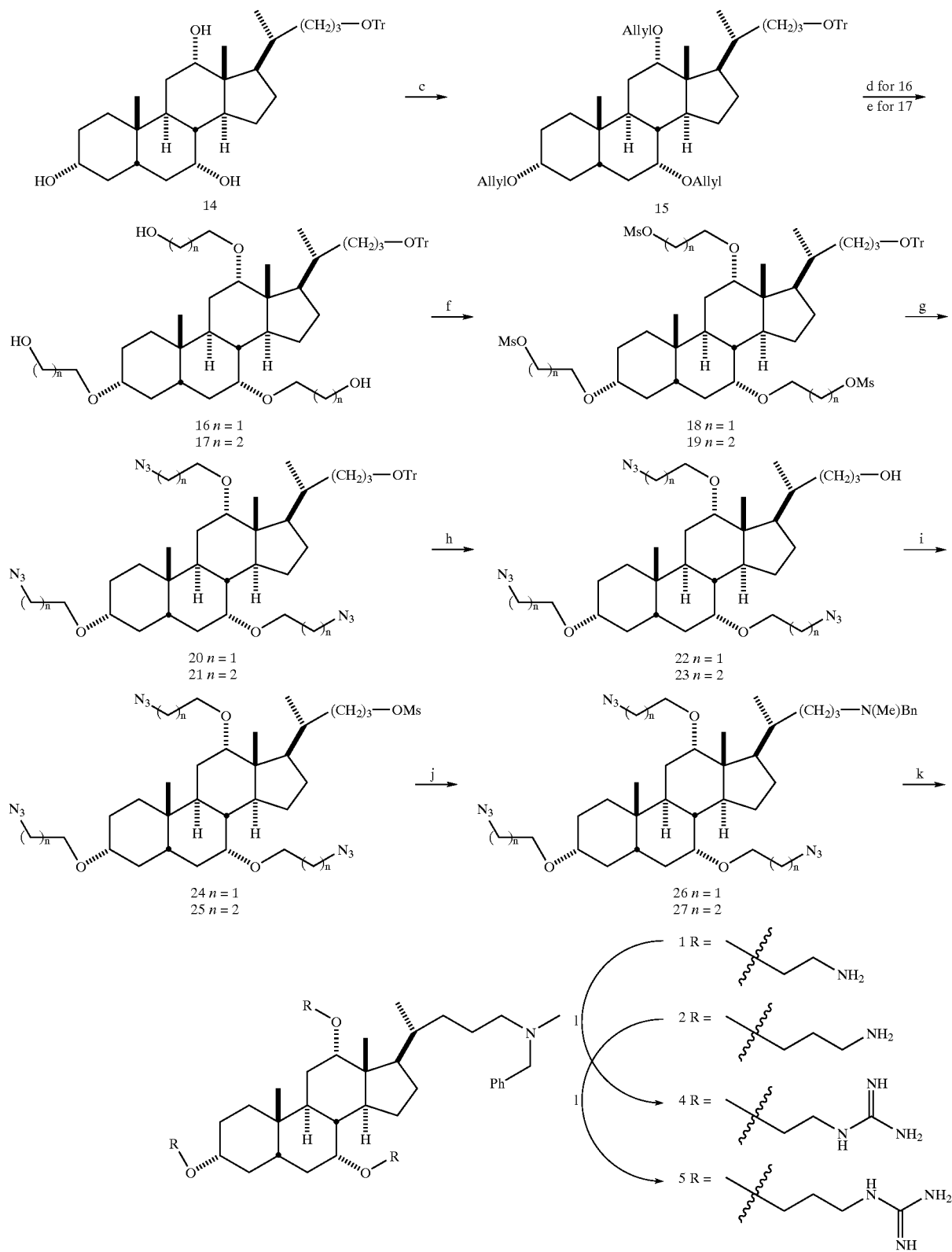
Reagents (reaction yields in parentheses): a) LiAlH$_4$, THF (98%). b) tritylchloride, Et$_3$N, DMF (70%). c) allylbromide, NaH, THF (96%). d) O$_3$, CH$_2$Cl$_2$, MeOH; Me$_2$S; NaBH$_4$ (95%). e) 9-BBN, THF; H$_2$O$_2$, NaOH (80%). f) MsCl, CH$_2$Cl$_2$, Et$_3$N (78%, 82%). g) NaN$_3$, DMSO (66% for 20, 19 carried directly on to 23). h) TsOH, MeOH (94%, 94% overall from 19), i) MsCl, CH$_2$Cl$_2$, Et$_3$N (99%, 97%). j) N-benzylmethylamine (95%, 96%). k) LiAlH$_4$, THF (95%, 99%). l) NH$_2$C(NH)SO$_3$H, MeOH (91%, 89%).

Scheme 2. Preparation of compound 3.

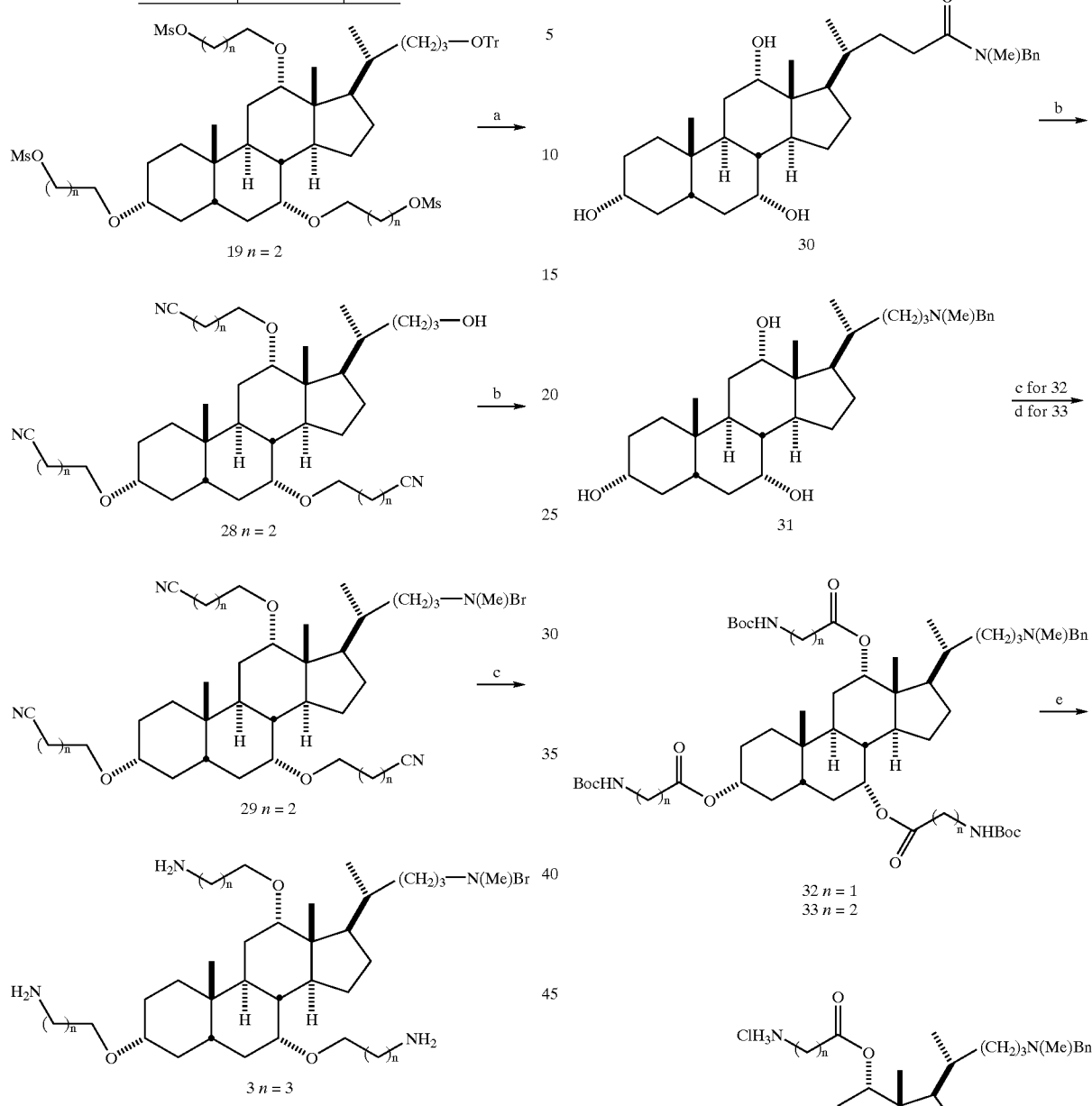

Reagents (reaction yields in parentheses): a) KCN, DMSO; MeOH, TsOH (92%). (b) MsCl, Et$_3$N, CH$_2$Cl$_2$; BnMeNH (88%). c) LiAlH$_4$, AlCl$_3$, THF (50%).

Scheme 3. Preparation of 6 and 7.

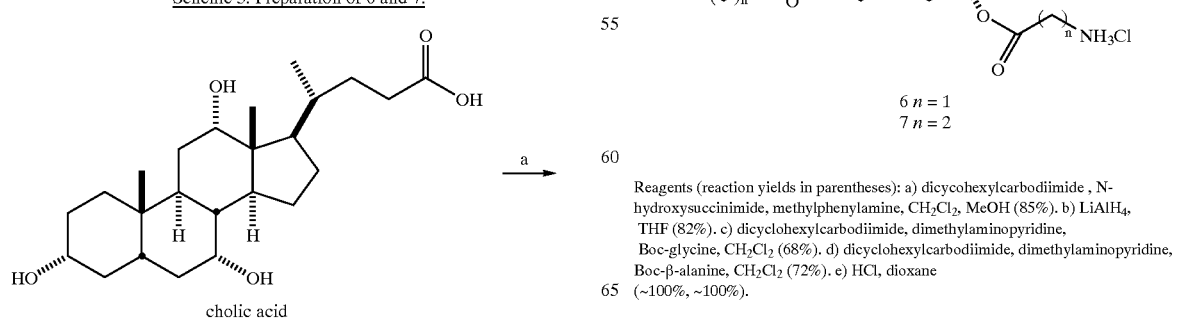

Reagents (reaction yields in parentheses): a) dicycohexylcarbodiimide, N-hydroxysuccinimide, methylphenylamine, CH$_2$Cl$_2$, MeOH (85%). b) LiAlH$_4$, THF (82%). c) dicyclohexylcarbodiimide, dimethylaminopyridine, Boc-glycine, CH$_2$Cl$_2$ (68%). d) dicyclohexylcarbodiimide, dimethylaminopyridine, Boc-β-alanine, CH$_2$Cl$_2$ (72%). e) HCl, dioxane (~100%, ~100%).

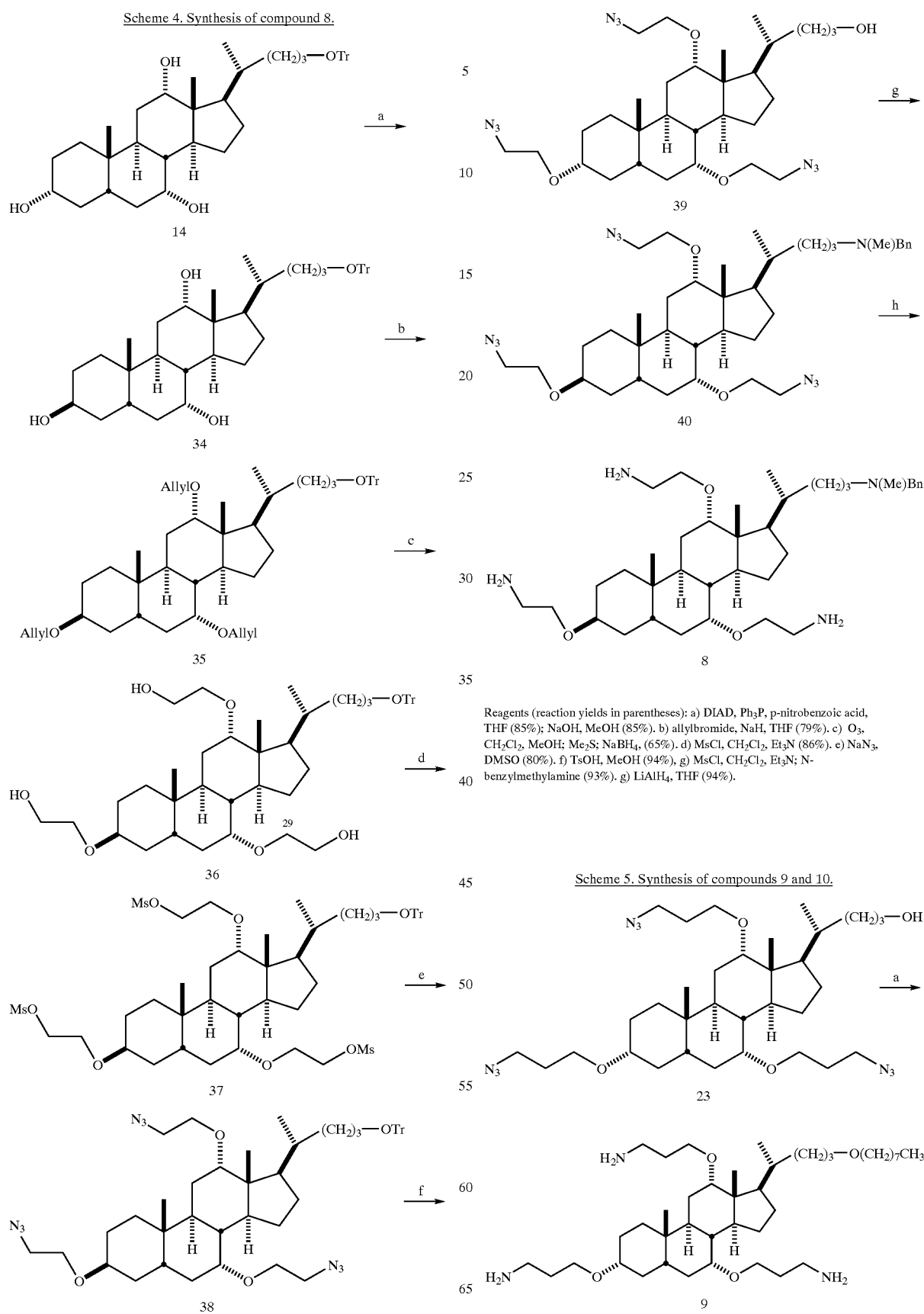

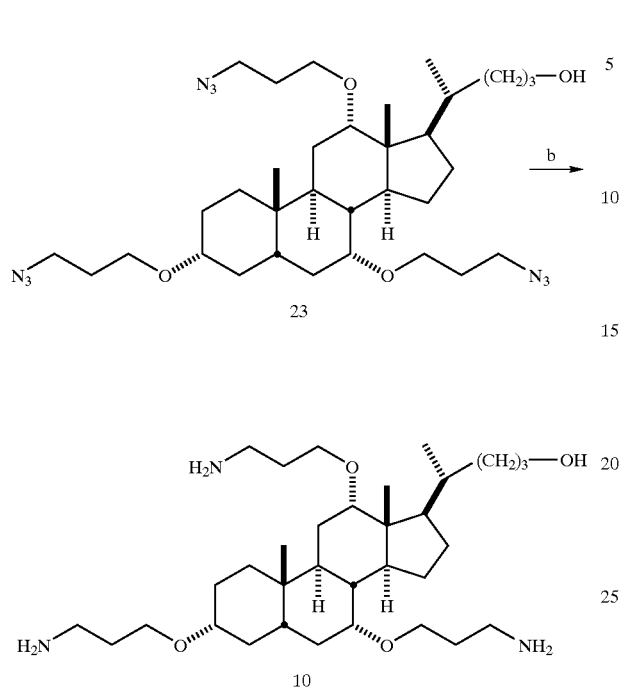

Reagents (reaction yields in parentheses): a) NaH, octyl bromide, DMF (80%); LiAlH4, THF (60%). b) LiAlH4, THF (60%)

Scheme 6. Synthesis of compound 11.

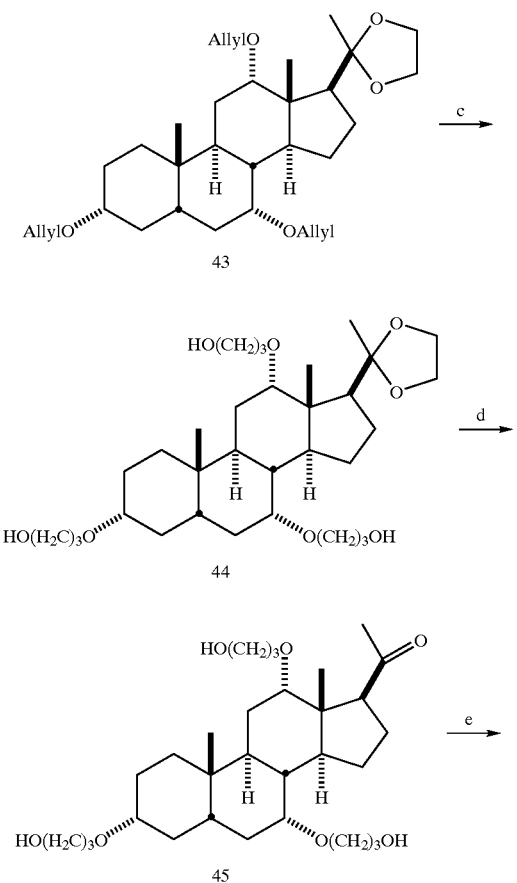

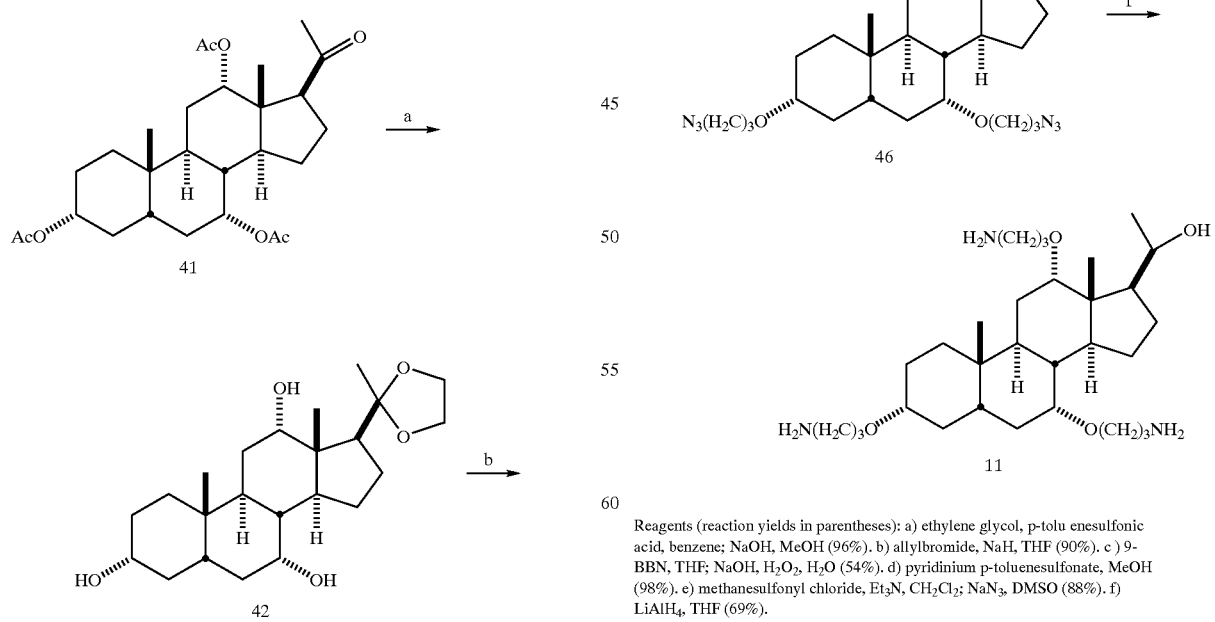

Reagents (reaction yields in parentheses): a) ethylene glycol, p-toluenesulfonic acid, benzene; NaOH, MeOH (96%). b) allylbromide, NaH, THF (90%). c) 9-BBN, THF; NaOH, H2O2, H2O (54%). d) pyridinium p-toluenesulfonate, MeOH (98%). e) methanesulfonyl chloride, Et3N, CH2Cl2; NaN3, DMSO (88%). f) LiAlH4, THF (69%).

Scheme 7. Synthesis of compound 12.
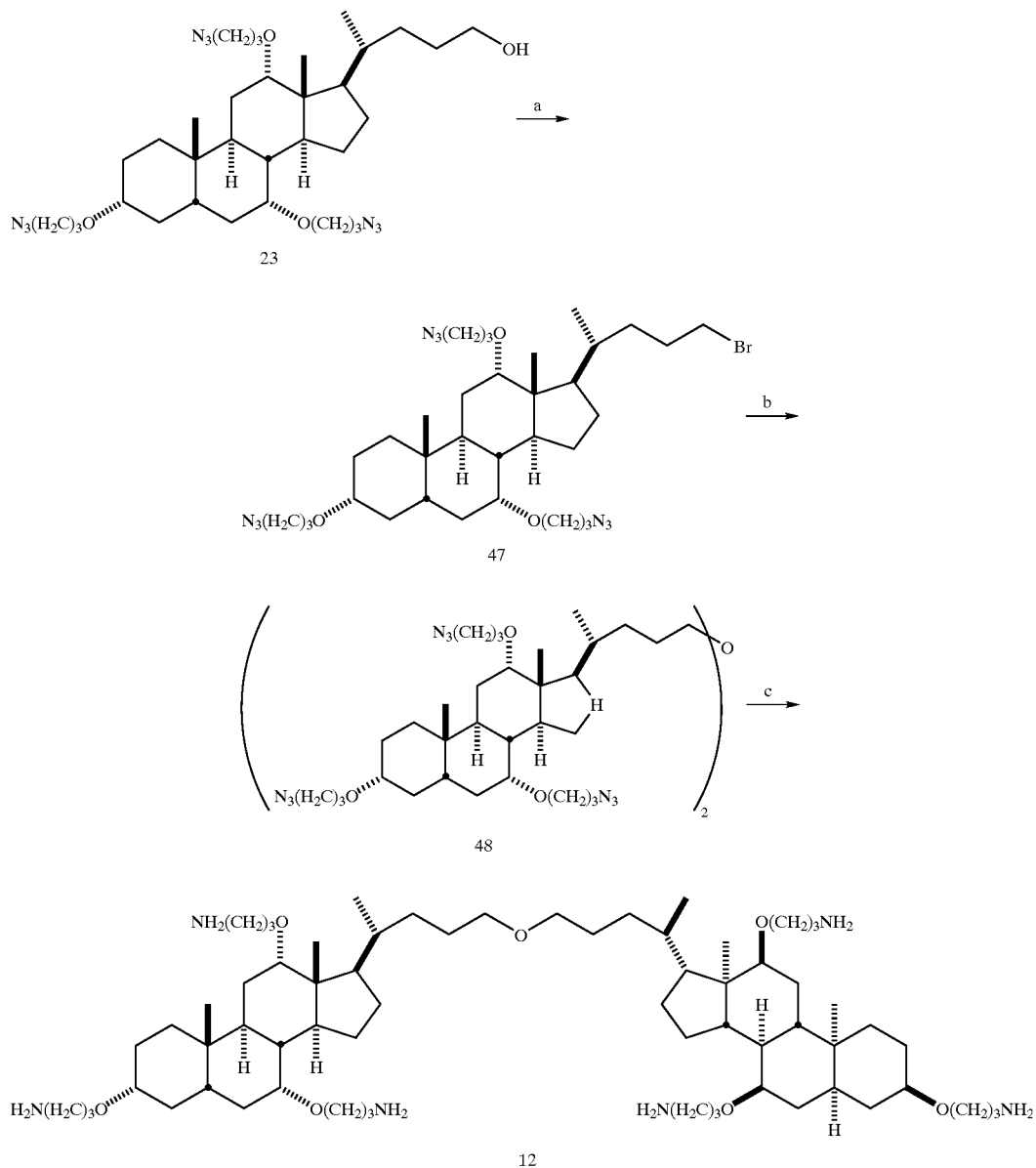
Reagents (reaction yields in parentheses): a) methanesulfonyl chlorid e, Et₃N, CH₂Cl₂; NaBr, DMF (97%). b) 23, NaH, DMF (52%). c) LiAlH₄, THF (76%).
Scheme 8. Preparation of compounds 111–114.
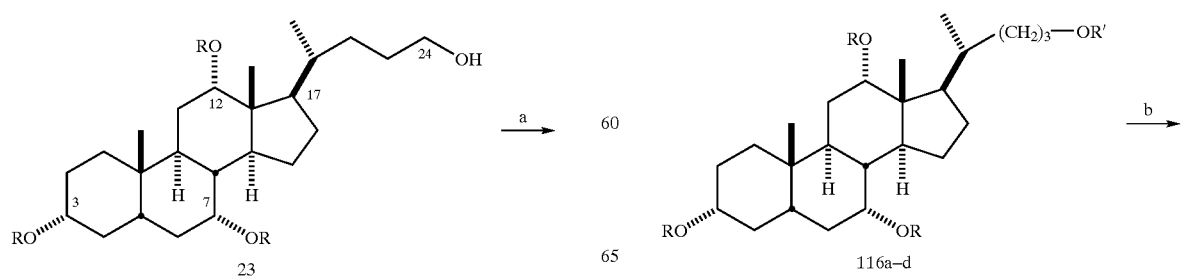

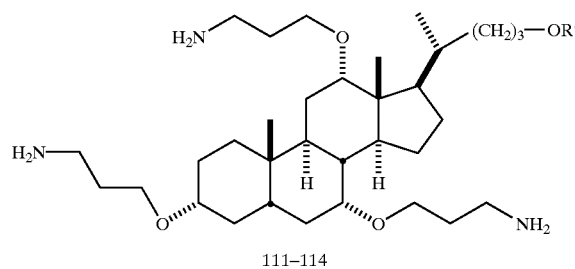

111–114 for 23, 116a–d, R = —(CH₂)₃N₃ for 116a, 111, R' = —CH₃         for 116c, 113, R' = —(CH₂)₄CH₃
for 116b, 112, R' = —(CH₂)₃CH₃   for 116d, 114, R' = —(CH₂)₇CH₃

Reagents (reaction yields in parentheses): a) NaH, DMF, CH₃I, CH₃(CH₂)₂Br, CH₃(CH₂)₄Br, or CH₃(CH₂)₇Br (85–90%). b) LiAlH₄, THF (55–70%).

Scheme 9. Preparation of compound 106.

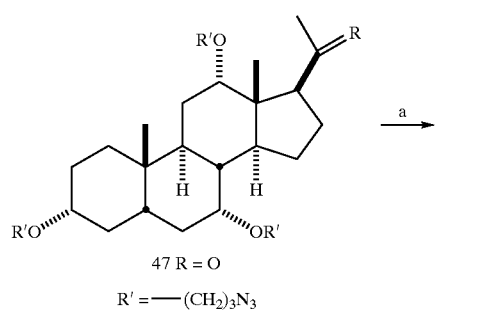

47 R = O
R' = —(CH₂)₃N₃

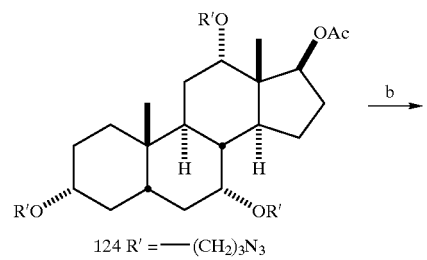

124 R' = —(CH₂)₃N₃

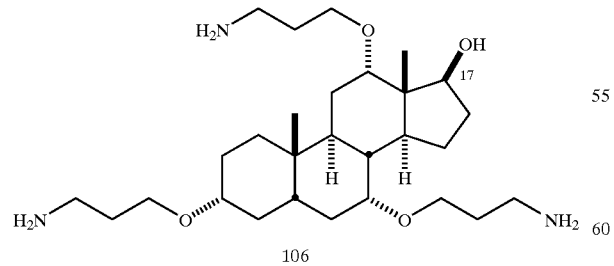

106

Reagents (reaction yields in parentheses): a) urea-hydrogen peroxide complex, trifluoroacetic anhydride, CH₂Cl₂ (55%). b) NaOH, MeOH; LiAlH₄, THF (43%).

Scheme 10. Preparation of compounds 108 and 109.

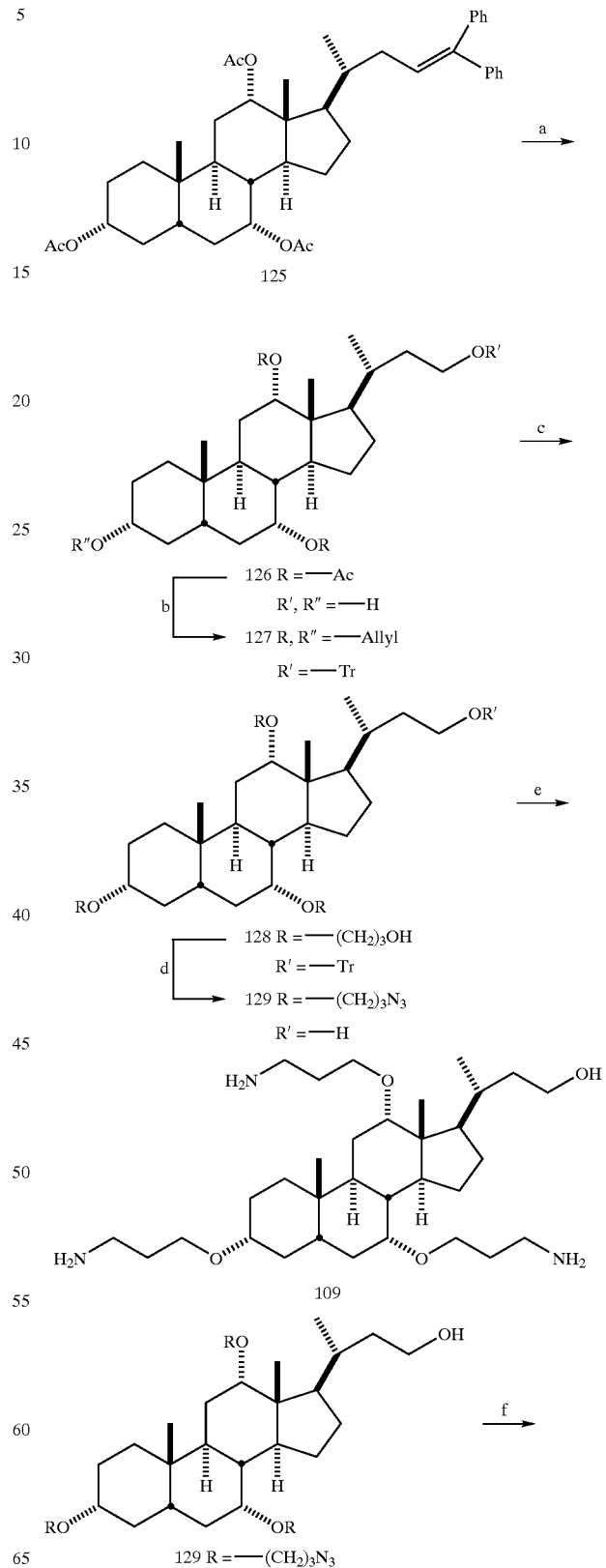

125

126 R = —Ac
    R', R'' = —H
127 R, R'' = —Allyl
    R' = —Tr

128 R = —(CH₂)₃OH
    R' = —Tr
129 R = —(CH₂)₃N₃
    R' = —H

109

129 R = —(CH₂)₃N₃

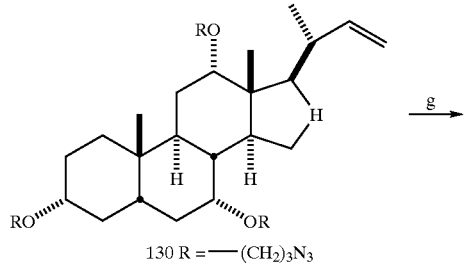

130 R = —(CH₂)₃N₃

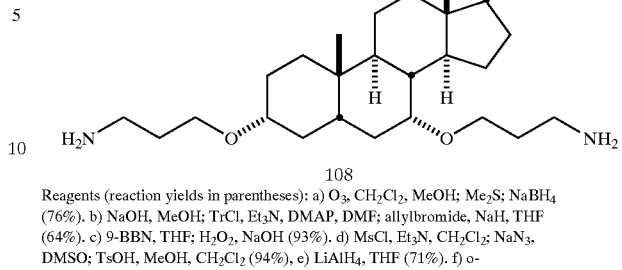

108

Reagents (reaction yields in parentheses): a) O₃, CH₂Cl₂, MeOH; Me₂S; NaBH₄ (76%). b) NaOH, MeOH; TrCl, Et₃N, DMAP, DMF; allylbromide, NaH, THF (64%). c) 9-BBN, THF; H₂O₂, NaOH (93%). d) MsCl, Et₃N, CH₂Cl₂; NaN₃, DMSO; TsOH, MeOH, CH₂Cl₂ (94%), e) LiAlH₄, THF (71%). f) o-NO₂C₆H₄SeCN, Bu₃P, THF; H₂O₂. (36%). g) O₃, CH₂Cl₂, MeOH; Me₂S; LiAlH₄, THF (68%).

Scheme 11
Preparation of compounds 202 and 203.

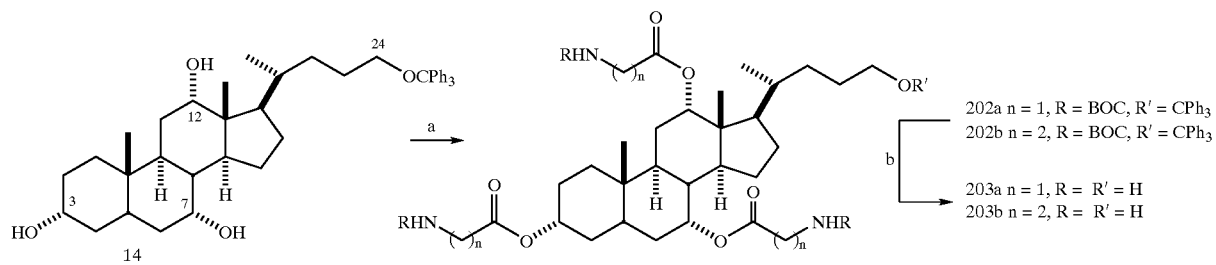

202a n = 1, R = BOC, R' = CPh₃
202b n = 2, R = BOC, R' = CPh₃

203a n = 1, R = R' = H
203b n = 2, R = R' = H

Reagents (reaction yields in parenthesis): a) BOC-glycine or BOC-alanine, DCC, DMAP, CH₂Cl₂ (60%, 94%). b) 4 M HCl in dioxane (74%, 71%).

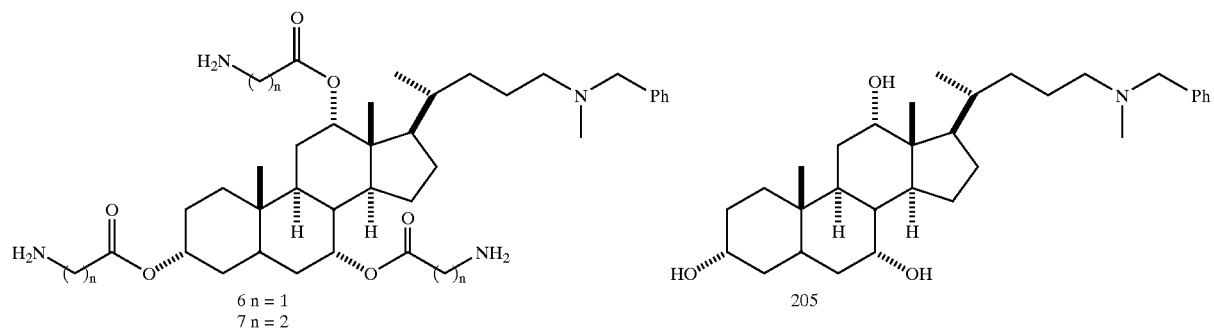

6 n = 1
7 n = 2

205

Scheme 12
Preparation of compounds 209a–209c

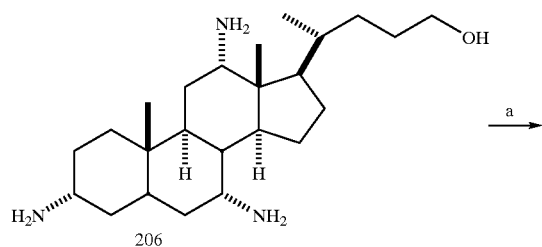

206

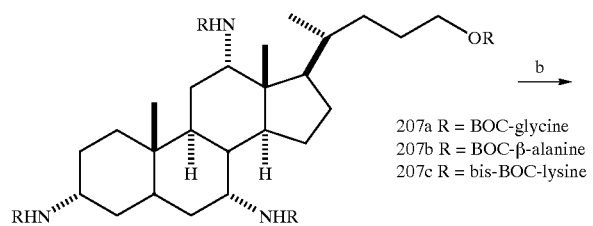
207a R = BOC-glycine
207b R = BOC-β-alanine
207c R = bis-BOC-lysine
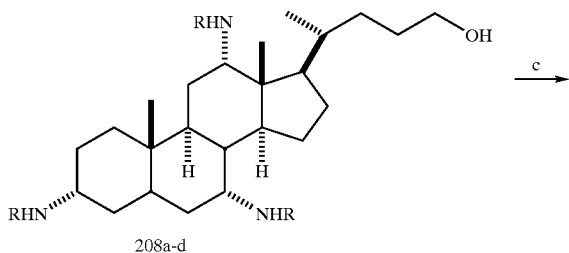
208a–d
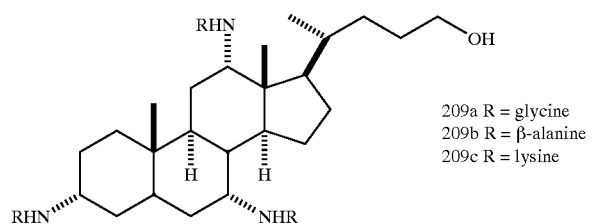
209a R = glycine
209b R = β-alanine
209c R = lysine
Reagents (reaction yields in parenthesis): a) BOC-glycine, BOC-alanine or bis-BOC-lysine, DCC, DMAP, $CH_2Cl_2$, b) LiOH, THF, MeOH (71–85% for two steps). c) 4 M HCl in dioxane (~100%).
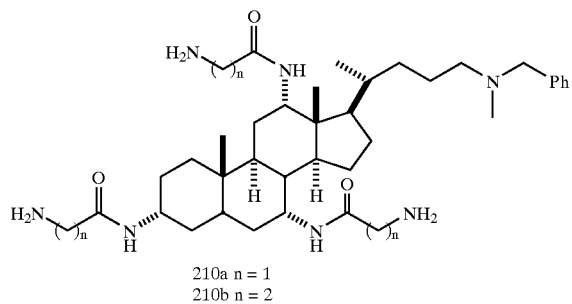
210a n = 1
210b n = 2
Scheme 13
Preparation of compounds 206
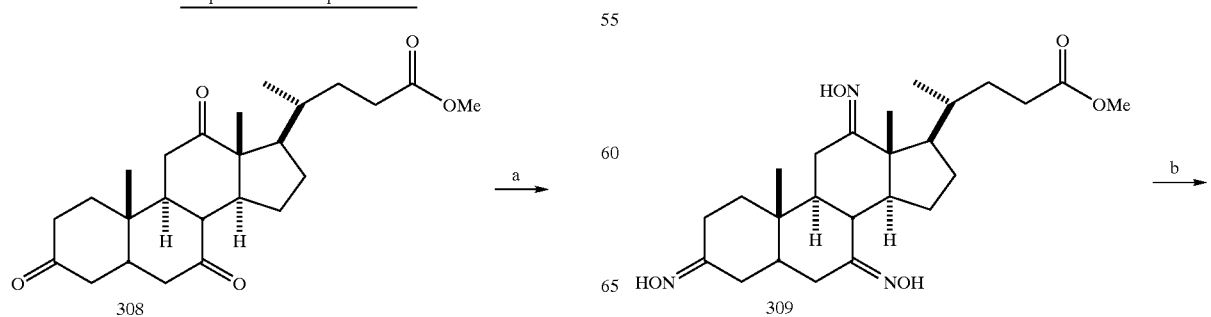
308
309
-continued

33

-continued

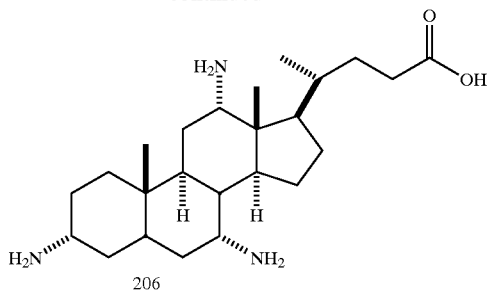

206

Reagents: a) NH₂OH·HCl, AcONa, EtOH(97%). b)NaBH₄, TiCl₄, glyme (33%).

34

-continued

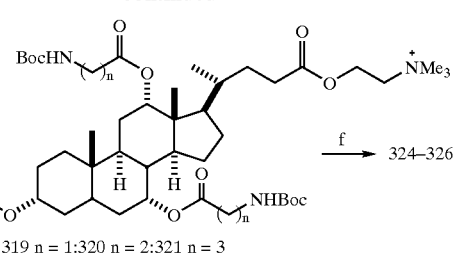

319 n = 1; 320 n = 2; 321 n = 3

³a) benzyl alcohol, TsOH (81%). b) Bocglycine, Boc-β-alanine or Boc-γ-aminobutyric acid, DCC, DMAP, CH₂Cl₂ (68–78%). c) H₂, Pd/C (97–99%). d) (CH₃)₂N(CH₂)₂OH, DCC, DMAP, CH₂Cl₂ or THF (62–82%). e) MeI, CH₂Cl₂. f) HCl, dioxane (83–90% for two steps).

Scheme 14

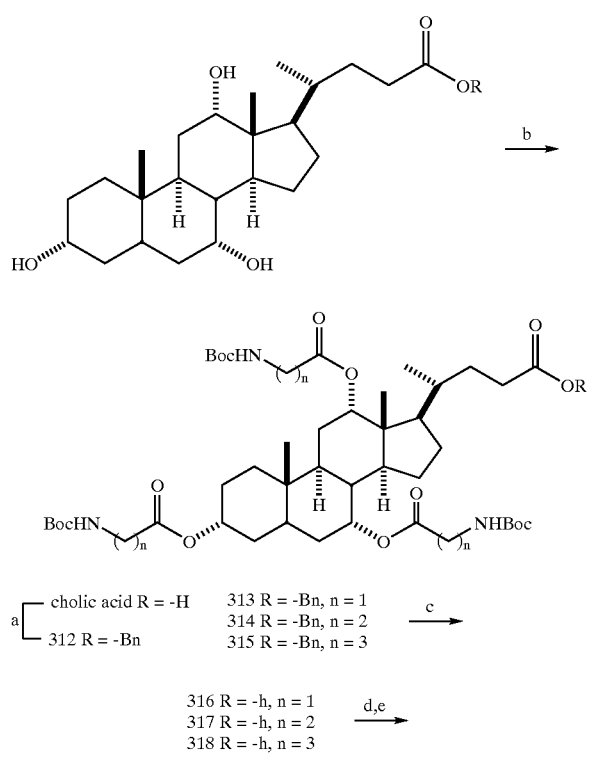

cholic acid R = -H
312 R = -Bn

313 R = -Bn, n = 1
314 R = -Bn, n = 2
315 R = -Bn, n = 3

316 R = -h, n = 1
317 R = -h, n = 2
318 R = -h, n = 3

Scheme 15

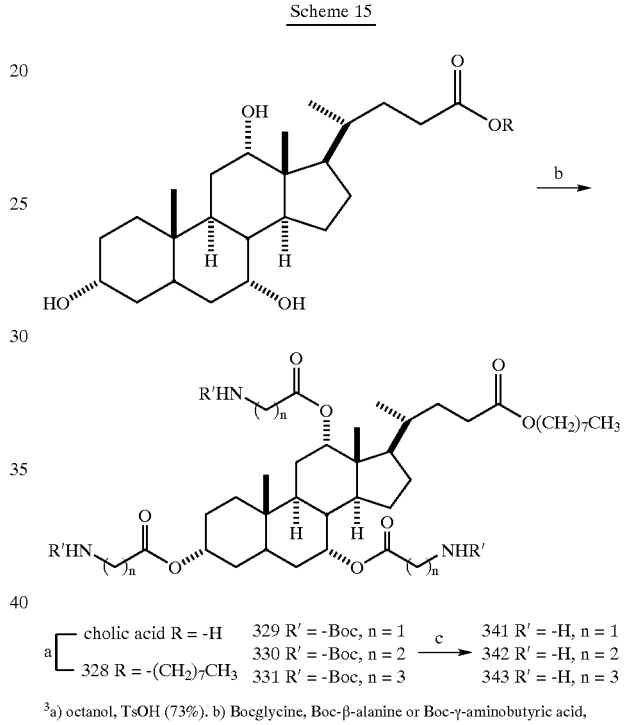

cholic acid R = -H
328 R = -(CH₂)₇CH₃

329 R' = -Boc, n = 1
330 R' = -Boc, n = 2
331 R' = -Boc, n = 3

341 R' = -H, n = 1
342 R' = -H, n = 2
343 R' = -H, n = 3

³a) octanol, TsOH (73%). b) Bocglycine, Boc-β-alanine or Boc-γ-aminobutyric acid, DCC, DMAP, CH₂Cl₂ (91–95%). c) HCl, dioxane (84–99%).

Scheme 16

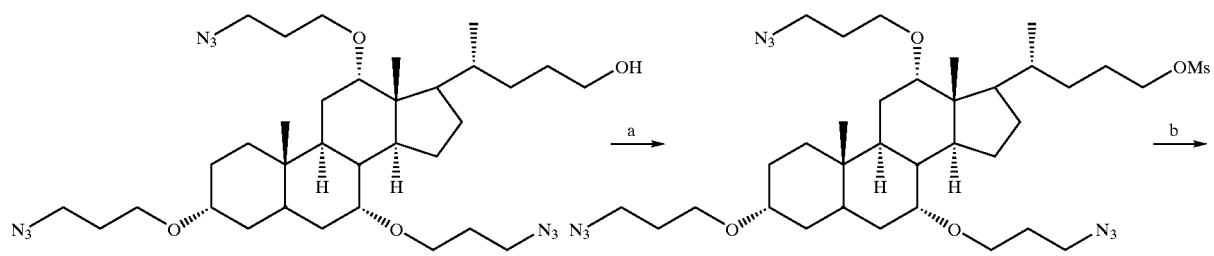

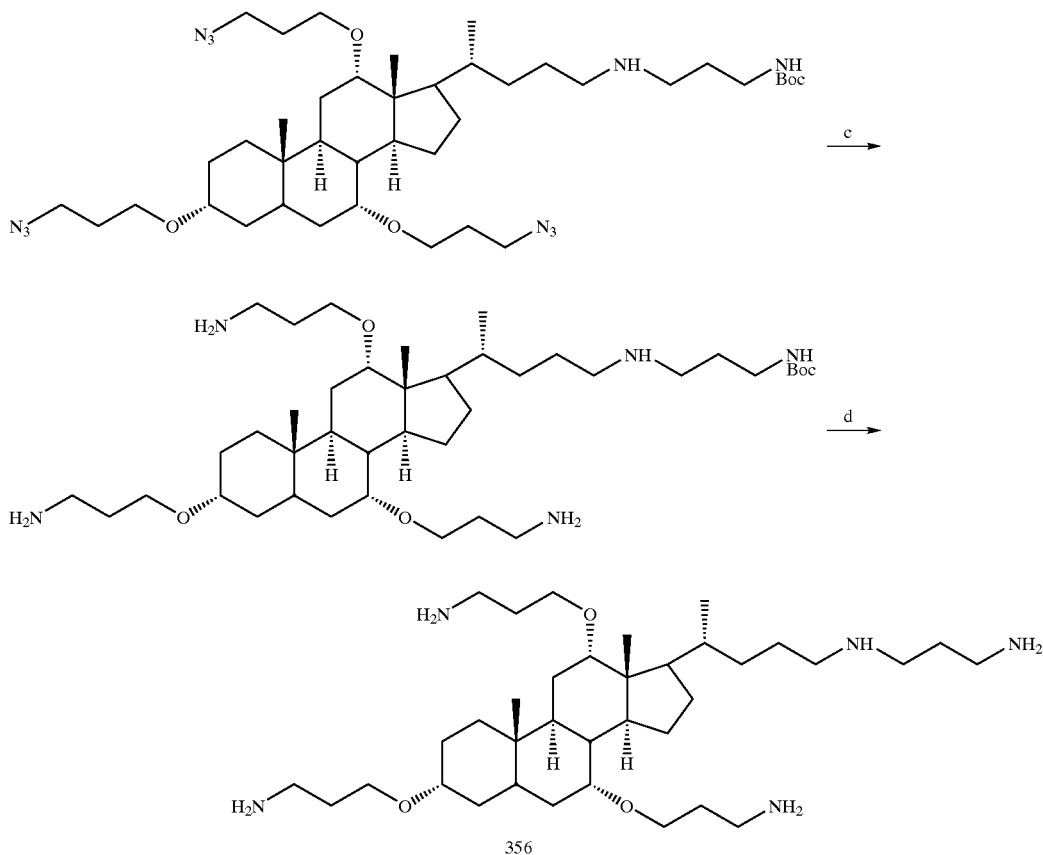
Reagents: a) MsCl, NEt₃, CH₂Cl₂, (86%). b) NH₂(CH₂)₃NHBoc, THF, (97%). c) PPh₃, THF/H₂O, (86%). d) HCl, 2M in ethyl ether, (89%)
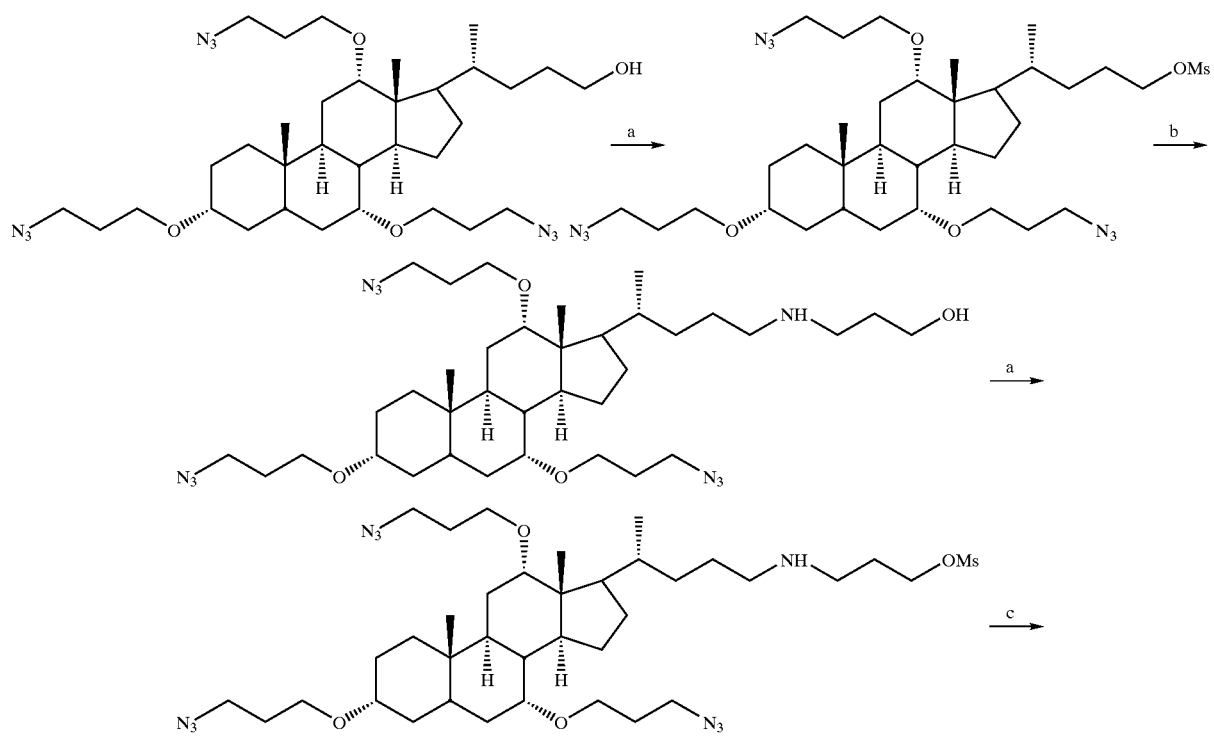

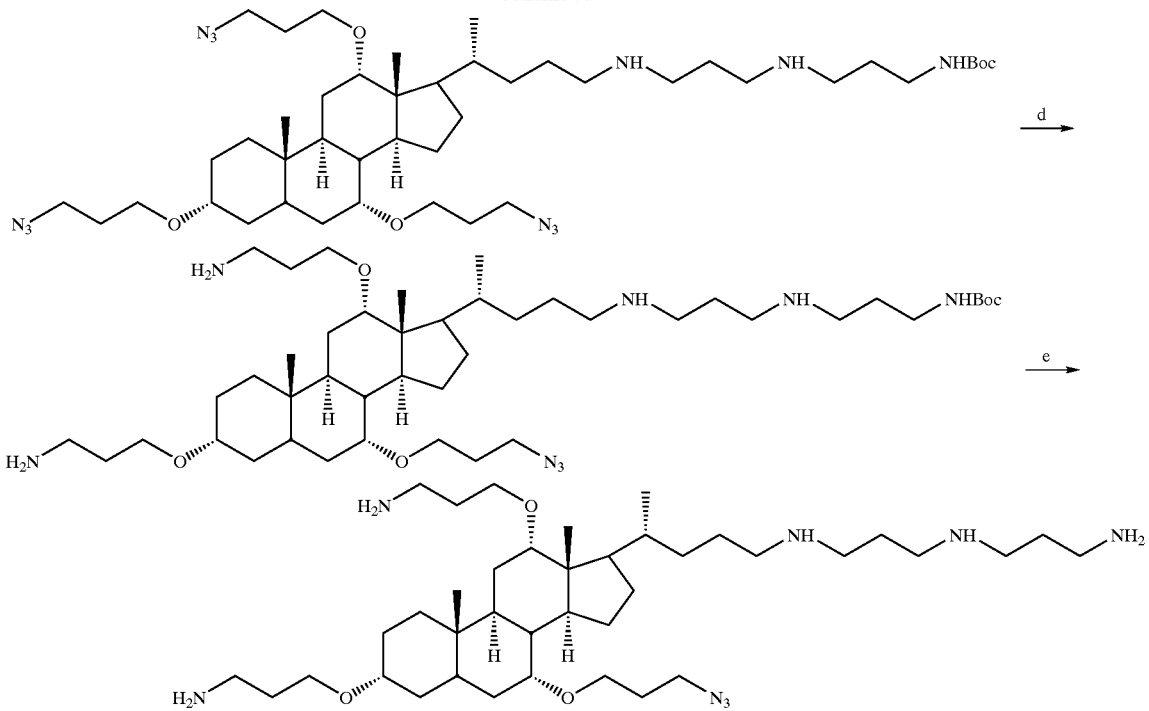

357

Reagents: a) MsCl, NEt₃, CH₂Cl₂, (86%). b) NH₂(CH₂)₃OH, THF, then step a. 63% for steps. c) NH₂(CH₂)₃NHBoc, THF, (83%). d) PPh₃, THF/H₂O, (90%). e) HCl, 2M in ethyl ether, (94%)

EXAMPLES

The examples illustrate particular synthesis of some particular compounds useful in the methods described herein. For example, representative syntheses of some of the compounds 1–343 are presented below.

¹H and ¹³C NMR spectra were recorded on a Varian Gemini 2000 (200 MHz), Varian Unity 300 (300 MHz), or Varian VXR 500 (500 MHz) spectrometer and are referenced to TMS, residual CHCl₃ (¹H) or CDCl₃ (¹³C), or residual CHD₂OD (¹H), or CD₃OD (¹³C). IR spectra were recorded on a Perkin Elmer 1600 FTIR instrument. Mass spectrometric data were obtained on a JOEL SX 102A spectrometer. THF was dried over Na/benzophenone and CH₂Cl₂ was dried over CaH₂ prior to use. Other reagents and solvents were obtained commercially and were used as received.

Example 1
Syntheses of Compounds 1, 2, 4, 5, 13–20 and 22–27

Compound 13: To a 1 L round-bottom flask were added methyl cholate (30.67 g, 72.7 mmol) in dry THF (600 mL) and LiAlH₄ (4.13 g, 109 mmol). After reflux for 48 hours, saturated aqueous Na₂SO₄(100 mL) was introduced slowly, and the resulted precipitate was filtered out and washed with hot THF and MeOH. Recrystallization from MeOH gave colorless crystals of 13 (28.0 g, 98% yield). m.p. 236.5–238° C.; IR (KBr) 3375, 2934, 1373, 1081 cm⁻¹; ¹H NMR (CDCl₃/MeOH-d4, 200 MHz) δ3.98 (bs, 1 H), 3.83 (bs, 1 H), 3.60–3.46 (m, 2 H), 3.38 (bs, 5 H), 2.30–2.10 (m, 2 H), 2.05–1.05 (series of multiplets, 22 H), 1.03 (bs, 3 H), 0.92 (s, 3 H), 0.71 (s, 3 H); ¹³C NMR (CDCl₃/MeOH-d4, 50 MHz) δ73.89, 72.44, 68.99, 63.51, 48.05, 47.12, 42.49, 40.37, 39.99, 36.62, 36.12, 35.58, 35.40, 32.77, 30.69, 30.04, 29.02, 28.43, 27.27, 23.96, 23.08, 18.00, 13.02; HRFAB-MS (thioglycerol+Na⁺ matrix) m/e: ([M+Na]⁺) 417.2992 (55.3%); calcd. 417.2981.

Compound 14: To a round-bottom flask were added 13 (28.2 g, 71.7 mmol) in DMF (300 ml), Et₃N (20 mL, 143.4 mmol), trityl chloride (25.98 g, 93.2 mmol) and DMAP (0.13 g, 1.07 mmol). The mixture was stirred at 50° C. under N₂ for 30 hours followed by the introduction of water (1000 mL) and extraction with EtOAc (5×200 mL). The combined extracts were washed with water and brine and then dried over MgSO₄. After removal of solvent in vacuo, the residue was purified using SiO₂ chromatography (CH₂Cl₂, Et₂O and MeOH as eluents) to give 14 as a pale yellow solid (31.9 g, 70% yield). m.p. 187° C. (decomposition); IR (KBr) 3405, 2935, 1448, 1075 cm⁻¹; ¹H NMR (CDCl₃, 200 MHz) δ7.46–7.42 (m, 6 H), 7.32–7.17 (m, 9 H), 3.97 (bs, 1 H), 3.83 (bs, 1 H), 3.50–3.38 (m, 1 H), 3.01 (bs, 1 H), 2.94 (dd, J=14.2, 12.2 Hz, 2 H), 2.64 (bs, 1 H), 2.51 (bs, 1 H), 2.36–2.10 (m, 2 H), 2.00–1.05 (series of multiplets, 22 H), 0.96 (d, J=5.8 Hz, 3 H), 0.87 (s, 3 H), 0.64 (s, 3 H); ¹³C NMR (CDCl₃, 50 MHz) δ144.77, 128.93, 127.91, 127.01, 86.43, 73.35, 72.06, 68.66, 64.28, 47.47, 46.53, 41.74, 41.62, 39.64, 35.57, 35.46, 34.91, 34.82, 32.40, 30.55, 28.21, 27.69, 26.80, 26.45, 23.36, 22.59, 17.83, 12.61; HRFAB-MS (thioglycerol+Na⁺ matrix) m/e: ([M+Na]⁺) 659.4069 (100%); calcd. 659.4076.

Compound 15: To a round-bottom flask were added 14 (20.0 g, 31.4 mmol) in dry THF (600 mL) and NaH (60% in mineral oil, 6.3 g, 157.2 mmol). The mixture was refluxed for 30 min under N₂ followed by addition of allyl bromide (27 mL, 314 mmol). After 60 hours of reflux, additional NaH (3 eq.) and allyl bromide (4 eq.) were added. Following another 50 hours of reflux, water (20 mL) was introduced slowly followed by addition of 1% HCl until the aqueous layer became neutral. The mixture was then extracted with ether (3×100 mL) and the combined extracts were washed with water (100 mL) and brine (2×100 mL). The ether solution was dried over anhydrous $Na_2SO_4$, and after removal of solvent, the residue was purified using $SiO_2$ chromatography (hexanes and EtOAc/hexanes 1:8 as eluents) to give 15 (22.76 g, 96% yield) as a pale yellow glass. IR (neat) 2930, 1448, 1087 $cm^{-1}$; $^1H$ NMR ($CDCl_3$, 200 MHz) δ7.48–7.30 (m, 6 H), 7.32–7.14 (m, 9 H), 6.04–5.80 (m, 3 H), 5.36–5.04 (series of multiplets, 6 H), 4.14–3.94 (m, 4 H), 3.74 (td, J=13.8, 5.8 Hz, 2 H), 3.53 (bs, 1 H), 3.20–2.94 (m, 3 H), 3.31 (bs, 1 H), 2.38–1.90 (m, 4 H), 1.90–0.96 (series of multiplets, 20 H), 0.90 (d, J=5.4 Hz, 3 H), 0.89 (s, 3 H), 0.64 (s, 3 H); $^{13}C$ NMR ($CDCl_3$, 50 MHz) δ144.83, 136.27, 136.08, 128.94, 127.90, 126.98, 116.46, 115.70, 86.42, 80.94, 79.29, 74.98, 69.52, 69.39, 68.86, 64.39, 46.51, 46.42, 42.67, 42.14, 39.92, 35.63, 35.51, 35.13, 32.45, 28.98, 28.09, 27.66, 27.57, 26.72, 23.32, 23.11, 17.92, 12.69; HRFAB-MS (thioglycerol+$Na^+$ matrix) m/e: ($[M+Na]^+$) 779.5013 (86.1%); calcd. 779.5015.

Compound 16: To a three-necked round bottom flask was added 15 (3.34 g, 4.4 mmol) in $CH_2Cl_2$ (200 mL) and methanol (100 mL). Through the cold solution (−78° C.) ozone was bubbled through until a blue color persisted. Excess ozone was removed with oxygen flow. The mixture was left in a dry ice-acetone bath for an hour. Methyl sulfide (2.4 mL) was added and 15 minutes later, the mixture was treated with $NaBH_4$ (1.21 g, 32 mmol) in 5% aqueous NaOH solution (10 mL)/methanol (10 mL) and allowed to warm to room temperature. The mixture was washed with brine (3×50 mL), and the combined brine wash was extracted with $CH_2Cl_2$ (2×50 mL). The organic solution was dried over $MgSO_4$. After $SiO_2$ chromatography (MeOH (5%) in $CH_2Cl_2$), 3.30 g (95% yield) of 16 was isolated as an oil. IR (neat) 3358, 2934, 1448, 1070 $cm^{-1}$; $^1H$ NMR ($CDCl_3$, 200 MHz) δ7.50–7.42 (m, 6 H), 7.32–7.17 (m, 9 H), 3.80–2.96 (series of multiplets, 20 H), 2.25–0.96 (series of multiplets, 24 H), 0.89 (bs, 6 H), 0.65 (s, 3 H); $^{13}C$ NMR ($CDCl_3$, 50 MHz) δ144.73, 128.88, 127.87, 126.96, 86.38, 81.05, 79.75, 76.59, 70.33, 69.66, 69.30, 64.20, 62.25, 62.16, 62.03, 46.77, 46.36, 42.63, 41.77, 39.60, 35.43, 35.23, 35.05, 34.89, 32.42, 28.91, 27.93, 27.56, 27.15, 26.68, 23.35, 22.98, 22.85, 18.15, 12.60; HRFAB-MS (thioglycerol+$Na^+$ matrix) m/e: ($[M+Na]^+$) 791.4860 (100%), calcd. 791.4863.

Compound 17: To a round-bottom flask was added 16 (1.17 g, 1.55 mmol) in dry THF (30 mL) under $N_2$ in ice-bath followed by 9-BBN/THF solution (0.5 M, 10.2 mL, 5.51 mmol). The mixture was stirred at room temperature for 12 hours. Aqueous NaOH (20%) (2 mL) and hydrogen peroxide (30%) (2 mL) were added in sequence. The mixture was refluxed for 1 hour followed by the addition of brine (60 mL) and extraction with EtOAc (4×30 mL). The combined extracts were dried over anhydrous $Na_2SO_4$. The product (1.01 g, 80% yield) was obtained as a colorless oil after $SiO_2$ chromatography (5% MeOH in $CH_2Cl_2$). IR (neat) 3396, 2936, 1448, 1365, 1089 $cm^{-1}$; $^1H$ NMR($CDCl_3$, 200 MHz) δ7.50–7.42 (m, 6 H), 7.34–7.16 (m, 9 H), 3.90–3.56 (m, 13 H), 3.50 (bs, 1 H), 3.40–2.96 (series of multiplets, 6 H), 2.30–0.94 (series of multiplets, 30 H), 0.90 (s, 3 H), 0.88 (d, J=5.4 Hz, 3 H), 0.64 (s, 3 H); $^{13}C$ NMR($CDCl_3$, 50 MHz) δ144.73, 128.88, 127.85, 126.94, 86.36, 80.52, 78.90, 76.36, 66.82, 66.18, 65.77, 64.22, 61.53, 61.41, 61.34, 46.89, 46.04, 42.60, 41.59, 39.60, 35.37, 35.27, 34.88, 32.75, 32.44, 32.31, 28.82, 27.65, 27.48, 27.13, 26.77, 23.35, 22.74, 22.38, 18.08, 12.48; HRFAB-MS (thioglycerol+$Na^+$ matrix) m/e: ($[M+Na]^+$) 833.5331 (100%), calcd. 833.5332.

Compound 18: To a round-bottom flask were added 16 (3.30 g, 4.29 mmol) in $CH_2Cl_2$ (150 mL) and $NEt_3$(2.09 mL, 15.01 mmol). The mixture was put in ice-bath under $N_2$ followed by addition of mesyl chloride (1.10 mL, 14.16 mmol). After 30 minutes, water (30 mL) and brine (200 mL) were added. The CH2Cl2 layer was washed with brine (2×50 mL) and dried over anhydrous $Na_2SO_4$. The combined aqueous mixture was extracted with EtOAc (3×100 mL). The combined extracts were washed with brine and dried over anhydrous $Na_2SO_4$. The desired product (3.35 g, 78% yield) was isolated as a pale yellow oil after $SiO_2$ chromatography (EtOAc/hexanes 1:1). IR (neat) 2937, 1448, 1352, 1174, 1120, 924 $cm^{-1}$; $^1H$ NMR ($CDCl_3$, 200 MHz) δ7.52–7.40 (m, 6 H), 7.34–7.20, (m, 9 H), 4.42–4.24 (m, 6 H), 3.90–3.64 (m, 4 H), 3.60–3.30 (m, 4 H), 3.24–3.00 (m, 3 H), 3.10 (s, 6 H), 3.05 (s, 3 H), 2.20–1.96 (m, 3 H)1.96–1.60 (m, 8 H), 1.60–0.94 (series of multiplets, 13 H), 0.91 (bs, 6 H), 0.65 (s, 3 H); $^{13}C$ NMR($CDCl_3$, 50 MHz) δ114.68, 128.85, 127.85, 126.96, 86.37, 81.37, 79.58, 76.58, 69.95, 69.43, 69.34, 66.52, 66.31, 65.59, 64.11, 46.80, 46.20, 42.65, 41.48, 39.35, 37.82, 37.48, 35.36, 34.92, 34.73, 32.37, 28.66, 28.01, 27.44, 27.03, 26.72, 23.17, 22.91, 22.72, 18.13, 12.50; HRFAB-MS (thioglycerol+$Na^+$ matrix) m/e: ($[M+Na]^+$) 1205.4176 (81.5%), calcd. 1205.4189.

Compound 19: To a round-bottom flask were added 17 (1.01 g, 1.25 mmol) in $CH_2Cl_2$ (50 mL) and $NEt_3$ (0.608 mL, 4.36 mmol). The mixture was put in ice-bath under $N_2$ followed by addition of mesyl chloride (0.318 mL, 4.11 mmol). After 30 minutes, water (10 mL) and then brine (80 mL) were added. The $CH_2Cl_2$ layer was washed with brine (2×20 mL) and dried over anhydrous $Na_2SO_4$. The combined aqueous mixture was extracted with EtOAc (3×40 mL). The combined extracts were washed with brine and dried over anhydrous $Na_2SO_4$. The desired product (1.07 g, 82%) was isolated as a pale yellowish oil after $SiO_2$ chromatography (EtOAc/hexanes 1:1). IR (neat) 2938, 1356, 1176, 1112 $cm^{-1}$; $^1H$ NMR ($CDCl_3$, 300 MHz) δ7.46–7.43, (m, 6 H), 7.32–7.22 (m, 9 H), 4.40–4.31 (m, 6 H), 3.72–3.64 (m, 2 H), 3.55 (dd, J=6.3, 5.8 Hz, 2 H), 3.51 (bs, 1 H), 3.32–3.14 (m, 3 H), 3.14–2.92 (m, 3 H), 3.01 (s, 3 H), 3.01 (s, 3 H), 3.00 (s, 3 H), 2.10–1.92 (m, 10 H), 1.92–1.58 (m, 8 H), 1.56–0.92 (series of multiplets, 12 H), 0.90 (s, 3 H), 0.89 (d, J=5.4 Hz, 3 H), 0.64 (s, 3 H); $^{13}C$ NMR($CDCl_3$, 75 MHz) δ144.67, 128.85, 127.85, 126.96, 86.42, 81.06, 79.83, 76.81, 68.12, 68.06, 68.02, 64.26, 64.06, 63.42, 46.76, 46.38, 42.73, 41.87, 39.73, 37.44, 37.32, 37.29, 35.52, 35.48, 35.32, 35.06, 32.53, 30.55, 30.28, 30.02, 29.15, 27.96, 27.69, 27.61, 26.75, 23.52, 23.02, 18.17, 12.64; HRFAB-MS (thioglycerol+$Na^+$ matrix) m/e: ($[M+Na]^+$) 1067.4672 (100%), calcd. 1067.4659.

Compound 20: To a round-bottom flask were added 18 (1.50 g, 1.50 mmol) in dry DMSO (20 mL) and $NaN_3$ (0.976 g, 15 mmol). The mixture was heated to 80° C. and stirred under $N_2$ overnight then diluted with water (100 mL). The resulted aqueous mixture was extracted with EtOAc (3×50 mL), and the combined extracts washed with brine and dried over anhydrous $Na_2SO_4$. The desired product (0.83 g, 66% yield) was isolated as a clear glass after $SiO_2$ chromatography (EtOAc/hexanes 1:5). IR (neat) 2935, 2106, 1448, 1302, 1114 $cm^{-1}$; $^1H$ NMR ($CDCl_3$, 200 MHz) δ7.50–7.42 (m, 6 H), 7.36–7.20 (m, 9 H), 3.84–3.70 (m, 2 H), 3.65 (t, J=4.9 Hz, 2 H), 3.55 (bs, 1 H), 3.44–3.08 (m, 10 H), 3.02 (t, J=6.4 Hz, 2 H), 2.38–0.96 (series of multiplets, 24 H), 0.92 (d, J=5.6 Hz, 3 H), 0.91 (s, 3 H), 0.65 (s, 3 H); $^{13}C$ NMR ($CDCl_3$, 50 MHz) δ114.84, 128.97, 127.92, 126.99, 86.42, 81.24, 80.12, 76.59, 67.84, 67.29, 66.66, 64.36, 51.67, 51.44, 51.18, 46.53, 46.23, 42.21, 41.93, 39.73, 35.66, 35.36, 35.06, 34.78, 32.40, 28.95, 27.76, 27.39, 26.87, 23.45, 22.98, 22.92, 17.98, 12.53; HRFAB-MS (thioglycerol+Na$^+$ matrix) m/e: ([M+Na]$^+$) 866.5040 (100%), calcd. 866.5057.

Compound 22: To a round-bottom flask were added 20 (830 mg, 0.984 mmol) in MeOH (30 mL) and CH$_2$Cl$_2$ (30 mL) and p-toluenesulfonic acid (9.35 mg, 0.0492 mmol). The solution was stirred at room temperature for 2.5 hours then saturated aqueous NaHCO$_3$ (10 mL) was introduced. Brine (30 mL) was added, and the mixture was extracted with EtOAc (4×20 mL). The combined extracts were dried over anhydrous Na$_2$SO$_4$. The desired product (0.564 g, 95% yield) was isolated as a pale yellowish oil after SiO$_2$ chromatography (EtOAc/hexanes 1:2). IR (neat) 3410, 2934, 2106, 1301, 1112 cm$^{-1}$; $^1$H NMR (CDCl$_3$, 200 MHz) δ3.80–3.54 (m, 7 H), 3.44–3.20 (m, 10 H), 2.35–0.96 (series of multiplets, 24 H), 0.95 (d, J=6.4 Hz, 3H), 0.92 (s, 3 H), 0.68 (s, 3 H); $^{13}$C NMR (CDCl$_3$, 50 MHz) δ81.10, 80.01, 76.60, 67.75, 67.16, 66.56, 63.63, 51.57, 51.34, 51.06, 46.29, 46.12, 42.12, 41.81, 39.60, 35.55, 35.23, 34.94, 34.66, 31.75, 29.48, 28.81, 27.72, 27.66, 27.29, 23.32, 22.86, 22.80, 17.85, 12.39; HRFAB-MS (thioglycerol+Na$^+$ matrix) m/e: ([M+Na]$^+$) 624.3965 (100%), calcd. 624.3962.

Compound 23: To a round-bottom flask were added 19 (1.07 g, 1.025 mmol) and NaN$_3$ (0.666 g, 10.25 mmol) followed the introduction of dry DMSO (15 mL). The mixture was heated up to 80° C. under N$_2$ overnight. After the addition of H$_2$O (100 mL), the mixture was extracted with EtOAc (4×40 mL) and the combined extracts were washed with brine (2×50 mL) and dried over anhydrous Na$_2$SO$_4$. After removal of solvent, the residue was dissolved in MeOH (15 mL) and CH$_2$Cl$_2$ (15 mL) followed by the addition of catalytic amount of p-toluenesulfonic acid (9.75 mg, 0.051 mmol). The solution was stirred at room temperature for 2.5 hours before the addition of saturated NaHCO$_3$ solution (15 mL). After the addition of brine (60 mL), the mixture was extracted with EtOAc (5×30 mL). The combined extracts were washed with brine (50 mL) and dried over anhydrous Na$_2$SO$_4$. The desired product (0.617 g, 94% yield for two steps) was obtained as a yellowish oil after SiO$_2$ chromatography (EtOAc/hexanes 1:2). IR (neat) 3426, 2928, 2094, 1456, 1263, 1107 cm$^{-1}$; $^1$H NMR (CDCl$_3$, 300 MHz) δ3.68–3.56 (m, 3 H), 3.56–3.34 (series of multiplets, 10 H), 3.28–3.00 (series of multiplets, 4 H), 2.20–2.00 (m, 3 H), 1.98–1.55 (series of multiplets, 15 H), 1.55–0.96 (series of multiplets, 13 H), 0.92 (d, J=6.6 Hz, 3 H), 0.89 (s, 3 H), 0.66 (s, 3 H); $^{13}$C NMR (CDCl$_3$, 75 MHz) δ80.63, 79.79, 76.04, 64.99, 64.45, 64.30, 63.72, 49.01, 48.94, 48.74, 46.49, 46.39, 42.70, 41.98, 39.80, 35.65, 35.42, 35.28, 35.08, 31.99, 29.78, 29.75, 29.70, 29.49, 29.06, 27.87, 27.79, 27.65, 23.53, 23.04, 22.85, 18.05, 12.59; HRFAB-MS (thioglycerol+Na matrix) m/e: ([M+Na]$^+$) 666.4415 (100%), calcd. 666.4431.

Compound 24: To a round-bottom flask were added 22 (0.564 g, 0.938 mmol) in CH$_2$Cl$_2$ (30 mL) and NEt$_3$ (0.20 mL, 1.40 mmol). The mixture was put in ice-bath under N$_2$ followed by addition of mesyl chloride (0.087 mL, 1.13 mmol). After 30 minutes, water (20 mL) and brine (100 mL) were added. The CH$_2$CL$_2$ layer was washed with brine (2×20 mL) and dried over anhydrous Na$_2$SO$_4$. The combined aqueous mixture was extracted with EtOAc (3×30 mL). The combined extracts were washed with brine and dried over anhydrous Na$_2$SO$_4$. The desired product (0.634 g, 99% yield) was isolated as a pale yellowish oil after SiO$_2$ chromatography (EtOAc/hexanes 1:2). IR (neat) 2935, 2106, 1356, 1175, 1113 cm$^{-1}$; $^1$H NMR (CDCl$_3$, 300 MHz) δ4.20 (t, J=6.8 Hz, 2 H), 3.80–3.75 (m, 1 H), 3.70–3.64 (m, 3 H), 3.55 (bs, 1 H), 3.44–3.01 (m, 10 H), 3.00 (s, 3 H), 2.32–2.17 (m, 3 H), 2.06–2.03 (m, 1 H), 1.90–0.88 (series of multiplets, 20 H), 0.95 (d, J=6.6 Hz, 3 H), 0.91 (s, 3 H), 0.68 (s, 3 H); $^{13}$C NMR (CDCl$_3$, 75 MHz) δ80.90, 79.86, 76.43, 70.78, 67.64, 66.99, 66.48, 51.50, 51.26, 50.97, 46.05, 45.96, 42.08, 41.71, 39.51, 37.33, 35.15, 34.86, 34.60, 31.34, 28.73, 27.62, 27.59, 27.51, 25.68, 23.22, 22.80, 22.70, 17.62, 12.33; HRFAB-MS (thioglycerol+Na$^+$ matrix) m/e: ([M+Na]$^+$) 702.3741 (100%), calcd. 702.3737.

Compound 25: To a round-bottom flask were added 23 (0.617 g, 0.96 mmol) in CH$_2$Cl$_2$ (30 mL) and NEt$_3$ (0.20 mL, 1.44 mmol). The mixture was put in ice-bath under N$_2$ followed by addition of mesyl chloride (0.089 mL, 1.15 mmol). After 30 minutes, water (20 mL) and brine (120 mL) were added. The CH$_2$Cl$_2$ layer was washed with brine (2×20 mL) and dried over anhydrous Na$_2$SO$_4$. The combined aqueous mixture was extracted with EtOAc (3×30 mL). The combined extracts were washed with brine and dried over anhydrous Na$_2$SO$_4$. The desired product (0.676 g, 97% yield) was isolated as a pale yellowish oil after removal of solvent. IR (neat) 2934, 2094, 1454, 1360, 1174, 1112 cm$^{-1}$; $^1$H NMR (CDCl$_3$, 300 MHz) δ4.17 (t, J=6.6 Hz, 2 H), 3.65–3.28 (series of multiplets, 11 H), 3.64–3.00 (series of multiplets, 4 H), 2.97 (s, 3 H), 2.18–1.96 (series of multiplets, 16 H), 1.54–0.94 (series of multiplets, 11 H), 0.89 (d, J=6.6 Hz, 3 H), 0.86 (s, 3 H), 0.63 (s, 3 H); $^{13}$C NMR (CDCl$_3$, 75 MHz) δ80.47, 79.67, 75.92, 70.84, 64.90, 64.37, 64.17, 48.90, 48.86, 48.66, 46.32, 46.26, 42.63, 41.87, 39.70, 37.39, 35.34, 35.28, 35.20, 34.99, 31.61, 29.68, 29.60, 28.96, 27.78, 27.68, 27.57, 25.79, 23.41, 22.95, 22.74, 17.82, 12.50; HRFAB-MS (thioglycerol matrix) m/e: ([M+H]$^+$) 722.4385 (22.1%), calcd. 722.4387.

Compound 26: To a 50 mL round-bottom flask was added 24 (0.634 g, 0.936 mmol) and N-benzylmethylamine (2 mL). The mixture was heated under N$_2$ at 80° C. overnight. Excess N-benzylmethylamine was removed under vacuum, and the residue was subjected to SiO$_2$ chromatography (EtOAc/hexanes 1:2). The desired product (0.6236 g, 95% yield) was isolated as a pale yellow oil. IR (neat) 2935, 2106, 1452, 1302, 1116 cm$^{-1}$; $^1$H NMR (CDCl$_3$, 200 MHz) δ7.32–7.24 (m, 5 H), 3.80–3.76 (m, 1 H), 3.70–3.60 (m, 3 H), 3.54 (bs, 1 H), 3.47 (s, 2 H), 3.42–3.10 (m, 10 H), 2.38–2.05 (m, 5 H), 2.17 (s, 3 H), 2.02–0.88 (series of multiplet, 21 H), 0.93 (d, J=7.0 Hz, 3 H), 0.91 (s, 3 H), 0.66 (s, 3 H); $^{13}$C NMR (CDCl$_3$, 50 MHz) δ139.60, 129.34, 128.38, 127.02, 81.22, 80.10, 76.71, 67.85, 67.29, 66.65, 62.45, 58.38, 51.65, 51.44, 51.16, 46.50, 46.21, 42.40, 42.20, 41.93, 39.72, 35.80, 35.34, 35.05, 34.76, 33.65, 28.93, 27082, 27.75, 27.38, 24.10, 23.45, 22.98, 22.91, 18.05, 12.50; HRFAB-MS (thioglycerol+Na$^+$ matrix) m/e: ([M−H]$^+$) 703.4748 (90.2%), calcd. 703.4772; ([M+H]$^+$) 705.4911 (100%), calcd. 705.4928; ([M+Na]$^+$) 727.4767 (1.5%), calcd. 727.4748.

Compound 27: To a 50 mL round-bottom flask was added 25 (0.676 g, 0.937 mmol) and N-benzylmethylamine (2 mL). The mixture was heated under N$_2$ at 80° C. overnight. Excess N-benzylmethylamine was removed under vacuum and the residue was subjected to SiO$_2$ chromatography (EtOAc/hexanes 1:2). The desired product (0.672 g, 96% yield) was isolated as a pale yellow oil. IR (neat) 2934, 2096, 1452, 1283, 1107 cm$^{-1}$; $^1$H NMR (CDCl$_3$, 300 MHz) δ7.34–7.20 (m, 5 H), 3.68–3.37 (series of multiplets, 13 H), 3.28–3.04 (m, 4 H), 2.33 (t, J=7.0 Hz, 2 H), 2.18 (s, 3 H), 2.20–2.00 (m, 3 H), 1.96–1.56 (series of multiplets, 14 H), 1.54–1.12 (m, 10 H), 1.10–0.96 (m, 3 H), 0.91 (d, J=8.7 Hz, 3 H), 0.89 (s, 3 H), 0.65 (s, 3 H); $^{13}$C NMR (CDCl$_3$, 75

MHz) δ139.48, 129.23, 128.30, 126.96, 80.66, 79.81, 76.08, 65.00, 64.46, 64.34, 62.50, 58.37, 49.02, 48.95, 48.75, 46.65, 46.40, 42.43, 42.00, 39.83, 35.86, 35.45, 35.30, 35.10, 33.83, 29.81, 29.78, 29.72, 29.09, 27.88, 27.81, 27.66, 24.19, 23.57, 23.06, 22.87, 18.15, 12.62; HRFAB-MS (thioglycerol matrix) m/e: ([M+H]$^+$) 747.5406 (77.2%), calcd. 747.5398.

Compound 1: To a round-bottom flask were added 26 (0.684 g, 0.971 mmol) in dry THF (30 mL) and LiAlH$_4$ (113.7 mg, 3.0 mmol) under N$_2$. The mixture was stirred at room temperature for 12 hours, and then Na$_2$SO$_4$.10 H$_2$O powder (10 g) was added slowly. After the grey color disappeared, the mixture was filtered through Celite and washed with dry THF. The product (0.581 g, 95% yield) was obtained as a colorless glass. IR (neat) 3372, 2937, 1558, 1455, 1362, 1102 cm$^{-1}$; $^1$H NMR (CDCl$_3$, 300 MHz) δ7.34–7.20 (m, 5 H), 3.68–3.48 (m, 5 H), 3.47 (s, 2 H), 3.29 (bs, 1 H), 3.22–3.00 (m, 3 H), 2.96–2.80 (m, 6 H), 2.32 (t, J=6.8, 5.4 Hz, 2 H), 2.17 (s, 3 H), 2.20–2.00 (m, 3 H), 1.96–0.96 (series of multiplets, 27 H), 0.93 (d, J=6.8 Hz, 3 H), 0.90, (s, 3 H), 0.67 (s, 3 H); $^{13}$C NMR (CDCl$_3$, 75 MHz) δ139.50, 129.22, 128.31, 126.96, 80.76, 79.85, 76.10, 70.90, 70.33, 70.24, 62.48, 58.27, 46.55, 46.45, 42.72, 42.58, 42.33, 41.99, 39.77, 35.78, 35.37, 35.01, 33.73, 29.07, 27.95, 27.71, 24.06, 23.46, 22.99, 18.14, 12.55; HRFAB-MS (thioglycerol matrix) m/e: ([M+H]$^+$) 627.5211 (100%), calcd. 627.5213.

HCl salt of compound 1: Compound 1 was dissolved in a minimum amount of CH$_2$Cl$_2$ and excess HCl in ether was added. Solvent and excess HCl were removed in vacuo and a noncrystalline white powder was obtained. $^1$H NMR (methanol-d4/15% (CDCl$_3$, 300 MHz) δ7.61–7.57 (m, 2 H), 7.50–7.48 (m, 3 H), 4.84 (bs, 10 H), 4.45 (bs, 1 H), 4.30 (bs, 1 H), 3.96–3.82 (m, 2 H), 3.78–3.69 (m, 2 H), 3.66 (bs, 1 H), 3.59–3.32 (series of multiplets, 4 H), 3.28–3.02 (m, 8 H), 2.81 (s, 3 H), 2.36–2.15 (m, 4 H), 2.02–1.68 (m, 8 H), 1.64–0.90 (series of multiplets, 12 H), 1.01 (d, J=6.35 Hz, 3 H), 0.96 (s, 3 H), 0.73 (s, 3 H); $^{13}$C NMR (methanol-d4/15% (CDCl$_3$, 75 MHz) δ132.31, 131.20, 130.92, 130.40, 83.13, 81.09, 78.48, 65.54, 64.98, 64.11, 60.87, 57.66, 47.51, 46.91, 43.52, 43.00, 41.38, 41.19, 41.16, 40.75, 40.30, 36.37, 36.08, 36.00, 35.96, 33.77, 29.68, 29.34, 28.65, 28.37, 24.42, 24.25, 23.33, 21.51, 18.80, 13.04.

Compound 2: To a round-bottom flask were added 27 (0.82 g, 1.10 mmol) in dry THF (150 mL) and LiAlH$_4$ (125 mg, 3.30 mmol) under N$_2$. The mixture was stirred at room temperature for 12 hours and Na$_2$SO$_4$.10 H$_2$O powder (10 g) was added slowly. After the grey color disappeared, the mixture was filtered through a cotton plug and washed with dry THF. THF was removed in vacuo and the residue dissolved in CH$_2$Cl$_2$ (50 mL). After filtration, the desired product was obtained as a colorless glass (0.73 g, 99% yield). IR (neat) 3362, 2936, 2862, 2786, 1576, 1466, 1363, 1103 cm$^{-1}$; $^1$H NMR (CDCl$_3$, 300 MHz) δ7.32–7.23 (m, 5 H), 3.67–3.63 (m, 1 H), 3.60–3.57 (m, 1 H), 3.53 (t, J=6.4 Hz, 2 H), 3.47 (s, 2 H), 3.46 (bs, 1 H), 3.24–3.17(m, 2 H), 3.12–2.99 (m, 2 H), 2.83–2.74 (series of multiplets, 6 H), 2.30 (t, J=7.3 Hz, 2 H), 2.15 (s, 3 H), 2.20–2.00 (m, 3 H), 1.95–1.51 (series of multiplets, 20 H), 1.51–1.08, (series of multiplets, 10 H), 1.06–0.80 (m, 3 H), 0.87 (d, J=8.1 Hz, 3 H), 0.86 (s, 3 H), 0.61 (s, 3 H); $^{13}$C NMR (CDCl$_3$, 75 MHz) δ139.35, 129.16, 128.22, 126.88, 80.44, 79.29, 75.96, 66.70, 66.52, 66.12, 62.45, 58.26, 46.76, 46.27, 42.69, 42.41, 42.02, 40.68, 40.10, 40.02, 39.82, 35.84, 35.47, 35.30, 35.06, 34.15, 34.09, 34.03, 33.80, 28.96, 27.93, 27.75, 27.71, 24.32, 23.53, 23.03, 22.75, 18.17, 12.58; HRFAB-MS (thioglycerol+Na$^+$ matrix) m/e: ([M+Na]$^+$) 691.5504 (38.5%), calcd. 691.5502.

HCl salt of compound 2: Compound 2 was dissolved in a minimum amount of CH$_2$Cl$_2$ and excess HCl in ether was added. Removal of the solvent and excess HCl gave a noncrystalline white powder. $^1$H NMR (methanol-d4/15% (CDCl$_3$, 300 MHz) δ7.60–7.59 (m, 2 H), 7.50–7.47 (m, 3 H), 4.82 (bs, 10 H), 4.43 (bs, 1 H), 4.32 (bs, 1 H), 3.85–3.79 (m, 1 H), 3.75–3.68 (m, 1 H), 3.64 (t, J=5.74 Hz, 2 H), 3.57 (bs, 1 H), 3.36–3.28 (m, 2 H), 3.25–3.00 (series of multiplets, 10 H), 2.82 (s, 3 H), 2.14–1.68 (series of multiplets, 19 H), 1.65–1.15 (series of multiplets, 11 H), 0.98 (d, J=6.6 Hz, 3 H), 0.95 (s, 3 H), 0.72 (s, 3 H); $^{13}$C NMR (methanol-d4/15% (CDCl$_3$, 75 MHz) δ132.21, 131.10, 130.58, 130.28, 81.96, 80.72, 77.60, 66.84, 66.58, 66.12, 61.03, 57.60, 44.16, 42.77, 40.62, 39.57, 39.43, 36.28, 36.03, 35.96, 35.78, 33.65, 29.48, 29.27, 29.11, 29.01, 28.61, 28.56, 28.35, 24.25, 23.56, 23.30, 21.17, 18.64, 12.90.

Compound 4: A suspension of 1 (79.1 mg, 0.126 mmol) and aminoiminomethanesulfonic acid (50.15 mg, 0.404 mmol) in methanol and chloroform was stirred at room temperature for 24 hours, and the suspension became clear. An ether solution of HCl (1 M, 1 mL) was added followed by the removal of solvent with N$_2$ flow. The residue was dissolved in H$_2$O (5 mL) followed by the addition of 20% aqueous NaOH (0.5 mL). The resulting cloudy mixture was extracted with CH$_2$Cl$_2$ (4×5 mL). The combined extracts were dried over anhydrous Na$_2$SO$_4$. Removal of solvent gave the desired product (90 mg, 95%) as white powder. m.p. 111–112° C. IR (neat) 3316, 2937, 1667, 1650, 1556, 1454, 1348, 1102 cm$^{-1}$; $^1$H NMR (5% methanol-d4/CDCl$_3$, 300 MHz) δ7.26–7.22 (m, 5 H), 4.37 (bs, 3 H), 3.71–3.51 (series of multiplets, 5 H), 3.44 (s, 2 H), 3.39–3.10 (series of multiplets, 10 H), 2.27 (t, J=6.83 Hz, 2 H), 2.13 (s, 3 H), 2.02–0.94 (series of multiplets, 33 H), 0.85 (d, J=5.62 Hz, 3 H), 0.84 (s, 3 H), 0.61 (s, 3 H); $^{13}$C NMR (5% methanol-d4/CDCl$_3$, 75 MHz) δ158.54, 158.48, 158.43, 138.27, 129.47, 128.32, 127.19, 81.89, 80.30, 77.34, 69.02, 68.46, 67.21, 62.36, 58.00, 47.36, 46.18, 43.26, 43.00, 42.73, 42.18, 41.48, 39.32, 35.55, 34.97, 34.89, 34.67, 33.63, 28.93, 28.28, 27.53, 27.16, 23.96, 23.28, 23.16, 22.77, 18.36, 12.58; HRFAB-MS (thioglycerol+Na$^+$ matrix) m/e: ([M+H]$^+$) 753.5858 (100%), calcd. 753.5867.

HCl salt of compound 4: Compound 4 was dissolved in minimum amount of CH$_2$Cl$_2$ and MeOH followed by addition of excess HCl in ether. The solvent was removed by N$_2$ flow, and the residue was subjected to high vacuum overnight. The desired product was obtained as noncrystalline white powder. $^1$H NMR (methanol-d4/20% (CDCl$_3$, 300 MHz) δ7.58 (bs, 2 H), 7.50–7.48 (m, 3 H), 4.76 (bs, 13 H), 4.45 (d, J=12.9 Hz, 1 H), 4.27 (dd, 1 H, J=12.9, 5.4 Hz), 3.82–3.00 (series of multiplets, 17 H), 2.81–2.80 (m, 3 H), 2.20–1.02 (series of multiplets, 27 H), 0.98 (d, J=6.59 Hz, 3 H), 0.95 (s, 3 H), 0.72 (s, 3 H); $^{13}$C NMR (methanol-d4/20% CDCl$_3$, 75 MHz) δ158.88, 158.72, 132.00, 131.96, 130.98, 130.15, 82.51, 81.07, 78.05, 68.50, 68.02, 67.94, 67.10, 60.87, 60.53, 57.38, 47.16, 46.91, 43.91, 43.11, 43.01, 42.91, 42.55, 40.28, 39.88, 39.95, 35.90, 35.73, 35.64, 33.53, 29.18, 28.35, 27.99, 24.02, 23.30, 21.35, 18.52, 18.44, 13.06.

Compound 5: A suspension of 2 (113 mg, 0.169 mmol) and aminoiminomethanesulfonic acid (67.1 mg, 0.541 mmol) in methanol and chloroform was stirred at room temperature for 24 hours. HCl in ether (1 M, 1 mL) was added followed by the removal of solvent with N$_2$ flow. The residue was subject to high vacuum overnight and dissolved in H$_2$O (5 mL) followed by the addition of 20% NaOH solution (1.0 mL). The resulting mixture was extracted with CH₂Cl₂ (5×5 mL). The combined extracts were dried over anhydrous Na₂SO₄. Removal of solvent gave desired the product (90 mg, 95% yield) as a white solid. m.p. 102–104° C. IR (neat) 3332, 3155, 2939, 2863, 1667, 1651, 1558, 1456, 1350, 1100 cm⁻¹; ¹H NMR (5% methanol-d4/CDCl₃, 300 MHz) δ7.35–7.24 (m, 5 H), 3.75–3.64 (m, 1 H), 3.57 (bs, 5 H), 3.50 (s, 2 H), 3.53–3.46 (m, 1 H), 3.40–3.10 (series of multiplets, 14 H), 2.34 (t, J=7.31 Hz, 2 H), 2.19 (s, 3 H), 2.13–0.96 (series of multiplets, 36 H), 0.91 (bs, 6 H), 0.66 (s, 3 H); ¹³C NMR (5% methanol-d4/CDCl₃, 75 MHz) δ157.49, 157.31, 157.23, 138.20, 129.52, 128.34, 127.23, 81.17, 79.19, 76.42, 65.63, 65.03, 64.70, 62.36, 58.02, 47.23, 46.24, 42.89, 42.18, 41.45, 39.45, 39.40, 39.30, 38.71, 35.61, 35.55, 35.02, 34.82, 33.69, 29.87, 29.59, 29.42, 28.84, 27.96, 27.56, 23.95, 23.40, 22.82, 22.64, 18.28, 12.54; HRFAB-MS (thioglycerol+Na⁺ matrix) m/e: ([M+H]⁺) 795.6356 (84.3%), calcd. 795.6337.

HCl salt of compound 5: Compound 5 was dissolved in minimum amount of CH₂Cl₂ and MeOH followed by the addition of excess HCl in ether. The solvent and excess HCl were removed by N₂ flow and the residue was subject to high vacuum overnight. The desired product was obtained as noncrystalline white powder. ¹H NMR (methanol-d4/10% CDCl₃, 300 MHz) δ7.62–7.54 (m, 2 H), 7.48–7.44 (m, 3 H), 4.84 (bs, 16 H), 4.46 (d, J=12.7 Hz, 1 H), 4.26 (dd, J=12.7, 3.42 Hz, 1 H), 3.78–3.56 (series of multiplets, 5 H), 3.38–3.05 (series of multiplets, 13 H), 2.80 (d, 3 H), 2.19–2.04 (m, 3 H), 2.02–1.04 (series of multiplets, 30 H), 0.98 (d, J=6.35 Hz, 3 H), 0.95 (s, 3 H), 0.72 (s, 3 H); ¹³C NMR (methanol-d4/10% CDCl₃, 75 MHz) δ158.75, 158.67, 132.32, 131.24, 130.83, 130.43, 82.49, 81.02, 77.60, 66.47, 65.93, 61.19, 60.85, 57.69, 47.79, 47.60, 44.29, 43.07, 40.86, 40.42, 40.19, 40.09, 39.76, 36.68, 36.50, 36.15, 35.94, 33.91, 30.75, 30.46, 29.74, 29.33, 28.71, 24.41, 24.03, 23.38, 22.21, 22.16, 18.59, 18.52, 13.09.

Example 2
Syntheses of Compounds 3, 28 and 29

Compound 28: A suspension of 19 (0.641 g, 0.614 mmol) and KCN (0.40 g, 6.14 mmol) in anhydrous DMSO (5 mL) was stirred under N₂ at 80° C. overnight followed by the addition of H₂O (50 mL). The aqueous mixture was extracted with EtOAc (4×20 mL). The combined extracts were washed with brine once, dried over anhydrous Na₂SO₄ and concentrated in vacuo. The residue was dissolved in CH₂Cl₂ (3 mL) and MeOH (3 mL) and catalytic amount of p-toluenesulfonic acid (5.84 mg, 0.03 mmol) was added. The solution was stirred at room temperature for 3 hours before the introduction of saturated NaHCO₃ solution (10 mL). After the addition of brine (60 mL), the mixture was extracted with EtOAc (4×30 mL). The combined extracts were washed with brine once and dried over anhydrous Na₂SO₄ and concentrated. The residue afforded the desired product (0.342 g, 92% yield) as pale yellowish oil after column chromatography (silica gel, EtOAc/hexanes 2:1). IR (neat) 3479, 2936, 2864, 2249, 1456, 1445, 1366, 1348, 1108 cm⁻¹; ¹H NMR (CDCl₃, 300 MHz) δ3.76–3.53 (m, 7 H), 3.32–3.06 (series of multiplets, 4 H), 2.57–2.46 (m, 6 H), 2.13–1.00 (series of multiplets, 31 H), 0.93 (d, J=6.35 Hz, 3 H), 0.90 (s, 3 H), 0.67 (s, 3 H); ¹³C NMR (CDCl₃, 75 MHz) δ119.91, 119.89, 80.75, 79.65, 76.29, 65.83, 65.37, 65.19, 63.63, 46.57, 46.44, 42.77, 41.79, 39.71, 35.63, 35.26, 35.02, 32.00, 29.46, 29.03, 27.96, 27.74, 26.64, 26.42, 26.12, 23.56, 22.98, 22.95, 18.24, 14.65, 14.54, 14.30, 12.60; HRFAB-MS (thioglycerol+Na⁺ matrix) m/e: ([M+Na]⁺) 618.4247 (67.8%), calcd. 618.4247.

Compound 29: To a solution of 28 (0.34 g, 0.57 mmol) in dry CH₂Cl₂ (15 mL) under N₂ at 0° C. was added NEt₃ (119.5 μL, 0.857 mmol) followed by the addition of mesyl chloride (53.1 μL, 0.686 mmol). The mixture was allowed to stir at 0° C. for 30 minutes before the addition of H₂O (6 mL). After the introduction of brine (60 mL), the aqueous mixture was extracted with EtOAc (4×20 mL). The combined extracts were washed with brine once, dried over anhydrous Na₂SO₄ and concentrated. To the residue was added N-benzylmethyl amine (0.5 mL) and the mixture was stirred under N₂ at 80° C. overnight. Excess N-benzylmethylamine was removed in vacuo and the residue was subject to column chromatography (silica gel, EtOAc/hexanes 2:1 followed by EtOAc) to afford product (0.35 g, 88% yield) as a pale yellow oil. IR (neat) 2940, 2863, 2785, 2249, 1469, 1453, 1366, 1348, 1108 cm⁻¹; ¹H NMR (CDCl₃, 300 MHz) δ7.34–7.21 (m, 5 H), 3.76–3.69 (m, 1 H), 3.64–3.50 (m, 4 H), 3.48 (s, 2 H), 3.31–3.05 (series of multiplets, 4 H), 2.52–2.46 (m, 6 H), 2.33 (t, J=7.32 H, 2 Hz), 2.18 (s, 3 H), 2.13–0.95 (series of multiplets, 30 H), 0.91 (d, J=6.80 H, 3 Hz), 0.90 (s, 3 H), 0.66 (s, 3 H); ¹³C NMR (CDCl₃, 75 MHz) δ139.37, 129.17, 128.26, 126.93, 119.96, 119.91, 80.73, 79.59, 76.26, 65.79, 65.35, 65.13, 62.47, 58.25, 46.74, 46.40, 42.72, 42.38, 41.76, 39.68, 35.78, 35.22, 34.98, 33.79, 28.99, 27.92, 27.71, 26.63, 26.38, 26.09, 24.21, 23.54, 22.96, 22.90, 18.28, 14.62, 14.51, 14.26, 12.58; HRFAB-MS (thioglycerol+Na⁺ matrix) m/e: ([M+H]⁺) 699.5226 (100%), calcd. 699.5213.

Compound 3: A solution of 29 (0.074 g, 0.106 mmol) in anhydrous TEF (10 mL) was added dropwise to a mixture of AlCl₃ (0.1414 g, 1.06 mmol) and LiAlH₄ (0.041 g, 1.06 mmol) in dry THF (10 mL). The suspension was stirred for 24 hours followed by the addition of 20% NaOH aqueous solution (2 mL) at ice-bath temperature. Anhydrous Na₂SO₄ was added to the aqueous slurry. The solution was filtered and the precipitate washed twice with THF. After removal of solvent, the residue was subject to column chromatography (silica gel, MeOH/CH₂Cl₂ 1:1 followed by MeOH/CH₂Cl₂/ NH₃.H₂O 4:4:1) to afford the desired product (0.038 g, 50% yield) as a clear oil. IR (neat) 3362, 2935, 2863, 2782, 1651, 1574, 1568, 1557, 1471, 1455, 1103 cm⁻¹; ¹H NMR (CDCl₃, 300 MHz) δ7.32–7.22 (m, 5 H), 3.60–3.02 (series of broad multiplets, 18 H), 2.90–2.70 (m, 5 H), 2.33 (t, J=7.20 Hz, 2 H), 2.24–2.04 (m, 3 H), 2.18 (s, 3 H), 1.96–0.96 (series of multiplets, 30 H), 0.90 (d, J=7.57 Hz, 3 H), 0.89 (s, 3 H), 0.64 (s, 3 H); ¹³C NMR (CDCl₃, 75 MHz) δ139.44, 129.24, 128.31, 126.97, 80.63, 79.65, 75.97, 68.44, 68.00, 67.96, 62.54, 58.40, 46.77, 46.30, 42.73, 42.43, 42.07, 41.92, 41.74, 41.72, 39.81, 35.82, 35.48, 35.07, 33.84, 31.04, 30.30, 30.10, 29.03, 28.11, 27.82, 27.81, 27.74, 27.67, 27.64, 24.31, 23.50, 23.04, 22.93, 18.22, 12.63; HRFAB-MS (thioglycerol+Na⁺ matrix) m/e: ([M+H]⁺) 711.6139 (100%), calcd. 711.6152; ([M+Na]⁺) 733.5974 (46.1%), calcd. 733.5972.

Example 3
Syntheses of Compounds 6, 7, and 30–33

Compound 30: Cholic acid (3.0 g, 7.3 mmol) was dissolved in CH₂Cl₂ (50 mL) and methanol (5 mL). Dicyclohexylcarbodiimide (DCC) (1.8 g, 8.8 mmol) was added followed by N-hydroxysuccinimide (~100 mg) and benzylmethylamine (1.1 g, 8.8 mmol). The mixture was stirred for 2 hours, then filtered. The filtrate was concentrated and chromatographed (SiO₂, 3% MeOH in CH₂Cl₂) to give 3.0 g of a white solid (81% yield). m.p. 184–186° C.; IR (neat) 3325, 2984, 1678 cm⁻¹; ¹H NMR (CDCl₃, 200 MHz) δ7.21 (m, 5 H), 4.51 (m, 2 H), 3.87 (m, 1 H), 3.74 (m, 2 H), 3.36 (m, 2 H), 2.84 (s, 3 H), 2.48–0.92 (series of multiplets, 28 H), 0.80 (s, 3 H), 0.58 (d, J=6.5 Hz, 3 H); ¹³C NMR (CDCl₃, 50 MHz) δ174.30, 173.94, 137.36, 136.63, 128.81, 128.46, 127.85, 127.50, 127.18, 126.28, 72.96, 71.76, 68.35, 53.39, 50.65, 48.77, 46.91, 46.33, 41.44, 39.36, 39.18, 35.76, 35.27, 34.76, 33.87, 31.54, 34.19, 31.07, 30.45, 28.11, 27.63, 26.14, 25.59, 24.92, 23.26, 17.51, 12.41; FAB-MS (thioglycerol+Na$^+$ matrix) m/e: ([M+H]$^+$) 512 (100%), calcd. 512.

Compound 31: Compound 30 (2.4 g, 4.7 mmol) was added to a suspension of LiAlH$_4$ (0.18 g, 4.7 mmol) in THF (50 mL). The mixture was refluxed for 24 hours, then cooled to 0° C. An aqueous solution of Na$_2$SO$_4$ was carefully added until the grey color of the mixture dissipated. The salts were filtered out, and the filtrate was concentrated in vacuo to yield 2.1 g of a white solid (88%). The product proved to be of sufficient purity for further reactions. m.p. 70–73° C.; IR (neat) 3380, 2983, 1502 cm$^{-1}$; $^1$H NMR (CDCl$_3$, 300 MHz) δ7.23 (m, 5 H), 3.98 (bs, 2 H), 3.81 (m, 3 H), 3.43 (m, 3 H), 2.74 (m, 2 H), 2.33 (m, 3 H), 2.25 (s, 3 H), 2.10–0.90 (series of multiplets, 24 H), 0.98 (s, 3 H), 0.78 (s, 3 H); $^{13}$C NMR (CDCl$_3$, 75 MHz) δ135.72, 129.63, 128.21, 128.13, 125.28, 72.91, 71.63, 62.05, 60.80, 56.79, 47.00, 46.23, 41.44, 40.81, 39.41, 35.42, 35.24, 34.63, 34.02, 33.22, 31.73, 30.17, 29.33, 29.16, 28.02, 27.49, 26.17, 25.55, 23.10, 22.48, 22.33, 17.54, 12.65; FAB-MS (thioglycerol matrix) m/e: ([M+H]$^+$) 498 (100%), calcd. 498.

Compound 32: Compound 31 (0.36 g, 0.72 mmol) was dissolved in CH$_2$Cl$_2$ (15 mL) and Bocglycine (0.51 g, 2.89 mmol), DCC (0.67 g, 3.24 mmol) and dimethylaminopyridine (DMAP) (~100 mg) were added. The mixture was stirred under N$_2$ for 4 hours then filtered. After concentration and chromatography (SiO$_2$, 5% MeOH in CH$_2$Cl$_2$), the product was obtained as a 0.47 g of a clear glass (68%). $^1$H NMR (CDCl$_3$, 300 MHz) δ7.30 (m, 5 H), 5.19 (bs, 1 H), 5.09 (bs, 3 H), 5.01 (bs, 1 H), 4.75 (m, 1 H), 4.06–3.89 (m, 6 H), 2.33 (m, 2 H), 2.19 (s, 3 H) 2.05–1.01 (series of multiplets, 26 H), 1.47 (s, 9 H), 1.45 (s, 18 H), 0.92 (s, 3 H), 0.80 (d, J=6.4 Hz, 3 H), 0.72 (s, 3 H). $^{13}$C NMR (CDCl$_3$, 75 MHz) δ170.01, 169.86, 169.69, 155.72, 155.55, 139.90, 129.05, 128.17, 126.88, 79.86, 76.53, 75.09, 72.09, 62, 35, 57.88, 47.78, 45.23, 43.12, 42.79, 42.16, 40.81, 37.94, 35.51, 34.69, 34.57, 34.36, 33.30, 31.31, 29.66, 28.80, 28.34, 27.22, 26.76, 25.61, 24.02, 22.83, 22.47, 17.93, 12.19; FAB-MS (thioglycerol matrix) m/e: ([M+H]$^+$) 970 (100%), calcd. 970.

Compound 33: Compound 31 (0.39 g, 0.79 mmol) was dissolved in CH$_2$Cl$_2$ (15 mL) and Boc-β-alanine (0.60 g, 3.17 mmol), DCC (0.73 g, 3.56 mmol) and dimethylaminopyridine (DMAP) (~100 mg) were added. The mixture was stirred under N$_2$ for 6 hours then filtered. After concentration and chromatography (SiO$_2$, 5% MeOH in CH$_2$Cl$_2$), the product was obtained as a 0.58 g of a clear glass (72%). IR (neat) 3400, 2980, 1705, 1510 cm$^{-1}$; $^1$H NMR (CDCl$_3$, 300 MHz) δ7.27 (m, 5 H), 5.12 (bs, 4 H), 4.93 (bs, 1 H), 4.71 (m, 1 H), 3.40 (m, 12 H), 2.59–2.48 (m, 6 H), 2.28 (m, 2 H), 2.17 (s, 3 H), 2.05–1.01 (series of multiplets, 26 H), 1.40 (s, 27 H), 0.90 (s, 3 H), 0.77 (d, J=6.1 Hz, 3 H), 0.70 (s, 3 H). $^{13}$C NMR (CDCl$_3$, 75 MHz) δ171.85, 171.50, 171.44, 155.73, 138.62, 129.02, 128.09, 126.87, 79.18, 75.53, 74.00, 70.91, 62.20, 57.67, 47.84, 44.99, 43.28, 41.98, 40.73, 37.67, 36.12, 34.94, 34.65, 34.47, 34.20, 33.29, 31.23, 29.57, 28.74, 28.31, 28.02, 27.86, 27.12, 26.73, 25.46, 24.86, 23.95, 22.77, 22.39, 17.91, 12.14; HRFAB-MS (thioglycerol+Na$^+$ matrix) m/e: ([M+H]$^+$) 1011.6619 (100%), calcd. 1011.6634.

Compound 6: Compound 32 (0.15 g, 0.15 mmol) was stirred with excess 4 N HCl in dioxane for 40 minutes. The dioxane and HCl were removed in vacuo leaving 0.12 g of a clear glass (~100%). $^1$H NMR (CD$_3$OD, 300 MHz) δ7.62 (bs, 2 H), 7.48 (bs, 3 H), 5.30 (bs, 1 H), 5.11 (bs, 1 H), 4.72 (bs (1 H), 4.46 (m, 1 H), 4.32 (m, 1H) 4.05–3.91 (m, 4 H), 3.10 (m, 2 H), 2.81 (s, 3 H), 2.15–1.13 (series of multiplets, 25 H), 1.00 (s, 3 H), 0.91 (bs, 3 H), 0.82 (s, 3 H). $^{13}$C NMR (CD$_3$OD, 125 MHz) δ166.86, 166.50, 131.09, 130.18, 129.17, 128.55, 76.60, 75.43, 72.61, 72.04, 70.40, 66.22, 60.07, 58.00, 57.90, 54.89, 54.76, 46.44, 44.64, 43.39, 42.22, 38.56, 36.78, 34.14, 33.92, 33.84, 31.82, 30.54, 29.67, 28.79, 27.96, 26.79, 26.00, 24.99, 23.14, 22.05, 21.82, 19.91, 17.27, 11.60; HRFAB-MS (thioglycerol+Na$^+$ matrix) m/e: ([M-4 Cl-3 H]$^+$) 669.4576 (100%), calcd. 669.4591.

Compound 7: Compound 33 (0.20 g, 0.20 mmol) was stirred with excess 4 N HCl in dioxane for 40 minutes. The dioxane and HCl were removed in vacuo leaving 0.12 g of a clear glass (~100%). $^1$H NMR (CD$_3$OD, 500 MHz) δ7.58 (bs, 2 H), 7.49 (bs, 3 H), 5.21 (bs, 1 H), 5.02 (bs, 1 H), 4.64 (m, 1 H), 4.44 (m, 1 H), 4.28 (m, 1 H), 3.30–2.84 (m, 14 H), 2.80 (s, 3 H), 2.11–1.09 (series of multiplets, 25 H), 0.99 (s, 3 H), 0.89 (d, J=4.1 Hz, 3 H), 0.80 (s, 3 H); $^{13}$C NMR (CD$_3$OD, 125 MHz) δ171.92, 171.56, 171.49, 132.44, 131.32, 131.02, 130.51, 78.13, 76.61, 61.45, 57.94, 46.67, 44.80, 42.36, 40.85, 39.33, 37.03, 36.89, 36.12, 36.09, 35.79, 35.63, 33.81, 33.10, 32.92, 32.43, 30.28, 28.43, 28.04, 26.65, 24.02, 22.86, 21.98, 18.70, 12.68; HRFAB-MS (thioglycerol+Na$^+$ matrix) m/e: ([M-4 Cl-3 H]$^+$) 711.5069 (43%), calcd. 711.5061.

Example 4

Syntheses of Compounds 8–10 and 34–40

Compound 34: Diisopropyl azodicarboxylate (DIAD) (1.20 mL, 6.08 mmol) was added to triphenylphosphine (1.60 g, 6.08 mmol) in THF (100 mL) at 0° C. and was stirred for half an hour during which time the yellow solution became a paste. Compound 14 (2.58 g, 4.06 mmol) and p-nitrobenzoic acid (0.81 g, 4.87 mmol) were dissolved in THF (50 mL) and added to the paste. The resulted mixture was stirred at ambient temperature overnight. Water (100 mL) was added and the mixture was made slightly basic by adding NaHCO$_3$ solution followed by extraction with EtOAc (3×50 mL). The combined extracts were washed with brine once and dried over anhydrous Na$_2$SO$_4$. The desired product (2.72 g, 85% yield) was obtained as white powder after SiO$_2$ chromatography (Et$_2$O/hexanes 1:2). m.p. 207–209° C.; IR (KBr) 3434, 3056, 2940, 2868, 1722, 1608, 1529, 1489, 1448, 1345 cm$^{-1}$; $^1$H NMR (CDCl$_3$, 300 MHz) δ8.30–8.26 (m, 2 H), 8.21–8.16 (m, 2 H), 7.46–7.42 (m, 6 H), 7.31–7.18 (m, 9 H)5.33 (bs, 1 H), 4.02 (bs, 1 H), 3.90 (bs, 1 H), 3.09–2.97 (m, 2 H), 2.68 (td, J=14.95, 2.56 Hz, 1 H), 2.29–2.19 (m, 1 H), 2.07–1.06 (series of multiplets, 24 H), 1.01 (s, 3 H), 0.98 (d, J=6.6 Hz, 3 H), 0.70 (s, 3 H); $^{13}$C NMR (CDCl$_3$, 75 MHz) δ164.21, 150.56, 144.70, 136.79, 130.77, 128.88, 127.86, 126.98, 123.70, 86.47, 73.24, 73.00, 68.70, 64.22, 47.79, 46.79, 42.15, 39.76, 37.47, 35.52, 35.34, 34.23, 33.79, 32.46, 31.12, 28.74, 27.71, 26.85, 26.30, 25.16, 23.41, 17.98, 12.77; HRFAB-MS (thioglycerol+Na$^+$ matrix) m/e: ([M+Na]$^+$) 808.4203 (53.8%), calcd. 808.4189. The nitrobenzoate (2.75 g, 3.5 mmol) was dissolved in CH$_2$Cl$_2$ (40 mL) and MeOH (20 mL) and 20% aqueous NaOH (5 mL) were added. The mixture was heated up to 60° C. for 24 hours. Water (100 mL) was introduced and extracted with EtOAc. The combined extracts were washed with brine and dried over anhydrous Na$_2$SO$_4$. The desired product (1.89 g, 85% yield) was obtained as white solid after SiO$_2$ chromatography (3% MeOH in CH$_2$Cl$_2$ as eluent). m.p. 105–106° C.; IR (KBr) 3429, 3057, 2936, 1596, 1489, 1447, 1376, 1265, 1034, 704 cm$^{-1}$; $^1$H NMR (CDCl$_3$, 300 MHz) δ7.46–7.42 (m, 6 H), 7.32–7.19 (m, 9 H), 4.06 (bs, 1 H), 3.99 (bs, 1 H), 3.86 (bd, J=2.44 Hz, 1 H), 3.09–2.97 (m, 2 H), 2.47 (td, J=14.03, 2.44 Hz, 1 H), 2.20–2.11 (m, 1 H), 2.04–1.04 (series of multiplets, 25 H), 0.97 (d, J=6.59 Hz, 3 H), 0.94 (s, 3 H), 0.68 (s, 3 H); $^{13}$C NMR (CDCl$_3$, 75 MHz) δ144.70, 128.88, 127.86, 126.97, 86.45, 73.31, 68.84, 67.10, 64.23, 47.71, 46.74, 42.10, 39.70, 36.73, 36.73, 36.15, 35.53, 35.45, 34.45, 32.46, 29.93, 28.67, 27.86, 27.71, 26.87, 26.04, 23.43, 23.16, 17.94, 12.75; HRFAB-MS (thioglycerol+Na$^+$ matrix) m/e: ([M+Na]$^+$) 659.4064 (100%), calcd. 659.4076.

Compound 35: To a round-bottom flask were added 34 (2.0 g, 3.14 mmol), NaH (60% in mineral oil, 3.8 g, 31.4 mmol) and THF (150 mL). The suspension was refluxed for 2 hours followed by the addition of allyl bromide (2.72 mL, 31.4 mL). After refluxing for 28 hours, another 10 eq. of NaH and allyl bromide were added. After 72 hours, another 10 eq. of NaH and allyl bromide were added. After 115 hours, TLC showed almost no starting material or intermediates. Water (100 mL) was added to the suspension carefully, followed by extraction with EtOAc (5×50 mL). The combined extracts were washed with brine and dried over anhydrous Na$_2$SO$_4$. The desired product (1.81 g, 79% yield) was obtained as a yellowish glass after SiO$_2$ chromatography (5% EtOAc/hexanes). IR (neat) 3060, 3020, 2938, 2865, 1645, 1596, 1490, 1448, 1376, 1076, 705 cm$^{-1}$; $^1$H NMR (CDCl$_3$, 300 MHz) δ7.46–7.42 (m, 6 H), 7.31–7.18 (m, 9 H), 6.06–5.85 (m, 3 H), 5.35–5.20 (m, 3 H), 5.15–5.06 (m, 3 H), 4.10–4.00 (m, 2 H), 3.93–3.90 (m, 2 H), 3.85–3.79 (ddt, J=13.01, 4.88, 1.59 Hz, 1 H), 3.73–3.66 (ddt, J=13.01, 5.38, 1.46 Hz, 1 H), 3.58 (bs, 1 H), 3.54 (bs, 1 H), 3.32 (d, J=2.93 Hz, 1 H), 3.07–2.96 (m, 2 H), 2.36 (td, J=13.67, 2.68 Hz, 1 H), 2.24–2.10 (m, 2 H), 2.03–1.94 (m, 1 H), 1.87–0.86 (series of multiplets, 20 H), 0.91 (s, 3 H), 0.90 (d, J=6.83 Hz, 3 H), 0.64 (s, 3 H); $^{13}$C NMR (CDCl$_3$, 75 MHz) δ144.77, 136.29, 136.21, 136.13, 128.90, 127.86, 126.94, 116.13, 115.51, 115.42, 86.44, 81.11, 75.65, 73.92, 69.40, 68.81, 64.43, 46.68, 46.54, 42.93, 39.93, 36.98, 35.66, 35.14, 35.14, 32.83, 32.54, 30.48, 28.51, 27.72, 27.64, 26.82, 24.79, 23.65, 23.43, 23.40, 18.07, 12.80; HRFAB-MS (thioglycerol+Na$^+$ matrix) m/e: ([M+H]$^+$) 757.5185 (12.9%), calcd. 757.5196.

Compound 36: Ozone was bubbled through a solution of 35 (0.551 g, 0.729 mmol) in CH$_2$Cl$_2$ (40 mL) and MeOH (20 mL) at −78° C. until the solution turned a deep blue. Excess ozone was blown off with oxygen. Methylsulfide (1 mL) was added followed by the addition of NaBH$_4$ (0.22 g, 5.80 mmol) in 5% NaOH solution and methanol. The resulted mixture was stirred overnight at room temperature and washed with brine. The brine was then extracted with EtOAc (3×20 mL). The combined extracts were dried over Na$_2$SO$_4$. The desired product (0.36 g, 65% yield) was obtained as a colorless glass after SiO$_2$ chromatography (5% MeOH/CH$_2$Cl$_2$). IR (neat) 3396, 3056, 2927, 1596, 1492, 1462, 1448, 1379, 1347, 1264, 1071 cm$^{-1}$; $^1$H NMR (CDCl$_3$, 300 MHz) δ7.46–7.42 (m, 6 H), 7.32–7.18 (m, 9 H), 3.77–3.57 (series of multiplets, 10 H), 3.48–3.44 (m, 2 H), 3.36–3.30 (m, 2 H), 3.26–3.20 (m, 1 H), 3.04–2.99 (m, 2 H), 2.37–0.95 (series of multiplets, 27 H), 0.92 (s, 3 H), 0.91 (d, J=6.59 Hz, 3 H), 0.67 (s, 3 H); $^{13}$C NMR (CDCl$_3$, 75 MHz) δ144.69, 128.87, 127.84, 126.94, 86.44, 81.05, 76.86, 74.65, 69.91, 69.22, 68.77, 64.24, 62.44, 62.42, 62.26, 46.92, 46.54, 42.87, 39.73, 36.86, 35.52, 35.13, 32.82, 32.54, 30.36, 28.71, 27.61, 27.44, 26.79, 24.82, 23.51, 23.38, 23.31, 18.28, 12.74; HRFAB-MS (thioglycerol+Na$^+$ matrix) m/e: ([M+Na]$^+$) 791.4844 (96.4%), calcd. 791.4863.

Compound 37: NEt$_3$ (0.23 mL, 1.66 mmol) was added to a solution of 36 (0.364 g, 0.47 mmol) in dry CH$_2$Cl$_2$ (30 mL) at 0° C. under N$_2$ followed by the introduction of mesyl chloride (0.12 mL, 1.56 mmol). The mixture was stirred for 10 minutes and H$_2$O (10 mL) added to quench the reaction, followed by extraction with EtOAc (3×30 mL). The combined extracts were washed with brine and dried over anhydrous Na$_2$SO$_4$. SiO$_2$ chromatography (EtOAc/hexanes 1:1) gave the desired product (0.411 g, 86% yield) as white glass. IR (neat) 3058, 3029, 2939, 2868, 1491, 1461, 1448, 1349, 1175, 1109, 1019 cm$^{-1}$; $^1$H NMR (CDCl$_3$, 300 MHz) δ7.46–7.42 (m, 6 H), 7.31–7.19 (m, 9 H), 4.35–4.26 (m, 6 H), 3.84–3.74 (m, 2 H), 3.64–3.56 (m, 4 H), 3.49–3.34 (m, 3 H), 3.06 (s, 3 H), 3.04 (s, 3 H), 3.02 (s, 3 H), 3.09–2.95 (m, 2 H), 2.28 (bt, J=14.89 Hz, 1 H), 2.09–0.86 (series of multiplets, 21 H), 0.92 (s, 3 H), 0.90 (d, J=6.78 Hz, 3 H), 0.66 (s, 3 H); $^{13}$C NMR (CDCl$_3$, 75 MHz) δ144.66, 128.86, 127.86, 126.97, 86.46, 81.28, 77.18, 75.00, 70.14, 69.89, 69.13, 66.49, 65.85, 65.72, 64.22, 47.06, 46.35, 42.77, 39.58, 37.81, 37.64, 37.55, 36.75, 35.48, 35.02, 32.59, 32.52, 30.27, 28.43, 27.56, 27.52, 26.92, 24.62, 23.34, 23.25, 23.10, 18.24, 12.64; HRFAB-MS (thioglycerol+Na$^+$ matrix) m/e: ([M+Na]$^+$) 1025.4207 (100%), calcd. 1025.4189.

Compound 38: The suspension of 37 (0.227 g, 0.227 mmol) and NaN$_3$ (0.147 g, 2.27 mmol) in dry DMSO (5 mL) was stirred at 80° C. overnight, diluted with H$_2$O (50 mL) and extracted with EtOAc (3×20 mL). The extracts were washed with brine once and dried over anhydrous Na$_2$SO$_4$. SiO$_2$ chromatography (EtOAc/hexanes 1:8) afforded the desired product (0.153 g, 80% yield) as a yellow oil. IR (neat) 2929, 2866, 2105, 1490, 1466, 1448, 1107, 705 cm$^{-1}$; $^1$H NMR (CDCl$_3$, 300 MHz) δ7.46–7.42 (m, 6 H), 7.32–7.19 (m, 9 H), 3.80–3.74 (m, 1 H), 3.70–3.55 (series of multiplets, 5 H), 3.41–3.19 (series of multiplets, 9 H), 3.04–2.98 (m, 2 H), 2.41 (td, J=13.1, 2.44 Hz, 1 H), 2.29–2.14 (m, 2 H), 2.04–0.86 (series of multiplets, 20 H), 0.93 (s, 3 H), 0.91 (d, J=6.60 Hz, 3 H), 0.66 (s, 3 H); $^{13}$C NMR (CDCl$_3$, 75 MHz) δ144.78, 128.93, 127.87, 126.96, 86.46, 81.30, 77.16, 75.21, 67.99, 67.44, 67.03, 64.41, 51.64, 51.57, 51.33, 46.71, 46.30, 42.35, 39.75, 36.72, 35.64, 35.20, 32.52, 32.42, 30.17, 28.63, 27.80, 27.22, 26.90, 24.80, 23.55, 23.30, 23.24, 18.23, 12.65; HRFAB-MS (thioglycerol+Na$^+$ matrix) m/e: ([M+Na]$^+$) 866.5049 (96.9%), calcd. 866.5057.

Compound 39: p-Toluenesulfonic acid (1.72 mg) was added into the solution of 38 (0.153 g, 0.18 mmol) in CH$_2$Cl$_2$ (5 mL) and MeOH (5 mL), and the mixture was stirred for 2.5 hours. Saturated NaHCO$_3$ solution (5 mL) was introduced followed by the introduction of brine (30 mL). The aqueous mixture was extracted with EtOAc and the combined extracts washed with brine and dried over Na$_2$SO$_4$. The desired product (0.10 g, 92% yield) was obtained as a pale yellowish oil after SiO$_2$ chromatography (EtOAc/hexanes 1:3). IR (neat) 3426, 2926, 2104, 1467, 1441, 1347, 1107 cm$^{-1}$; $^1$H NMR (CDCl$_3$, 300 MHz) δ3.81–3.74 (m, 1 H), 3.71–3.54 (m, 7 H), 3.41–3.19 (m, 9 H), 2.41 (td, J=13.61, 2.32 Hz, 1 H), 2.30–2.14 (m, 2 H), 2.07–1.98 (m, 1 H), 1.94–0.95 (series of multiplets, 21 H), 0.95 (d, J=6.35 Hz, 3 H), 0.93 (s, 3 H), 0.69 (s, 3 H); $^{13}$C NMR (CDCl$_3$, 75 MHz) δ81.22, 77.08, 75.13, 67.94, 67.36, 66.97, 63.76, 51.59, 51.51, 51.26, 46.51, 46.24, 42.31, 39.68, 36.64, 35.58, 35.12, 32.34, 31.92, 30.11, 29.55, 28.54, 27.82, 27.16, 24.75, 23.47, 23.23, 23.18, 18.15, 12.56; HRFAB-MS (thioglycerol+Na$^+$ matrix) m/e: ([M+Na]$^+$) 624.3966 (54.9%), calcd. 624.3962.

Compound 40: To a solution of 39 (0.10 g, 0.166 mmol) in CH$_2$C$_2$ (8 mL) at 0° C. was added NEt$_3$ (34.8 μL, 0.25 mmol) under N$_2$ followed by the introduction of mesyl chloride (15.5 μL, 0.199 mmol). The mixture was stirred 15 minutes. Addition of $H_2O$ (3 mL) and brine (20 mL) was followed by extraction with EtOAc (4×10 mL). The combined extracts were washed with brine once and dried over $Na_2SO_4$. After removal of solvent, the residue was mixed with N-benzylmethylamine (0.5 mL) and heated to 80° C. under $N_2$ overnight. Excess N-benzyl methylamine was removed in vacuo and the residue was subjected to $SiO_2$ chromatography (EtOAc/hexanes 1:4) to give the product (0.109 g, 93% yield) as a yellow oil. IR (neat) 2936, 2784, 2103, 1467, 1442, 1346, 1302, 1106, 1027 $cm^{-1}$; $^1H$ NMR ($CDCl_3$, 300 MHz) δ7.32–7.23 (m, 5 H), 3.81–3.74 (m, 1 H), 3.71–3.55 (m, 5 H), 3.47 (s, 2 H), 3.41–3.19 (m, 9 H), 2.46–2.11 (m, 5 H), 2.18 (s, 3 H), 2.03–0.85 (series of multiplets, 20 H), 0.93 (s, 3 H), 0.93 (d, J=6.35 Hz, 3 H,), 0.67 (s, 3 H); $^{13}C$ NMR ($CDCl_3$, 75 MHz) δ139.54, 129.26, 128.32, 126.97, 81.26, 77.12, 75.17, 67.98, 67.42, 67.00, 62.50, 58.41, 51.61, 51.54, 51.29, 46.66, 46.28, 42.46, 42.32, 39.72, 36.68, 35.76, 35.16, 33.75, 32.38, 30.15, 28.59, 27.85, 27.19, 24.77, 24.15, 23.53, 23.28, 23.22, 18.28, 12.60; HRFAB-MS (thioglycerol+$Na^+$ matrix) m/e: ([M+H]$^+$) 705.4929 (100%), calcd. 705.4928.

Compound 8: A suspension of 40 (0.109 g, 0.155 mmol) and $LiAlH_4$ (23.5 mg, 0.62 mmol) in THF (20 mL) was stirred under $N_2$ overnight. $Na_2SO_4 \cdot 10H_2O$ was carefully added and stirred until no grey color persisted. Anhydrous $Na_2SO_4$ was added and the white precipitate was filtered out and rinsed with dry THF. After removal of solvent, the residue was dissolved in minimum $CH_2Cl_2$ and filtered. The desired product (0.091 g, 94% yield) was obtained as a colorless oil after the solvent was removed. IR (neat) 3371, 3290, 3027, 2938, 2862, 2785, 1586, 1493, 1453, 1377, 1347, 1098 $cm^{-1}$; $^1H$ NMR ($CDCl_3$, 300 MHz) δ7.31–7.21 (m, 5 H), 3.65–3.53 (m, 4 H), 3.47 (s, 2 H), 3.42–3.34 (m, 2 H), 3.30 (bs, 1 H), 3.26–3.20 (m, 1 H), 3.14–3.09 (m, 1 H), 2.89–2.81 (m, 6 H), 2.39–2.27 (m, 3 H), 2.17 (s, 3 H), 2.15–0.88 (series of multiplets, 29 H), 0.93 (d, J=6.59 Hz, 3 H), 0.92 (s, 3 H), 0.67 (s, 3 H); $^{13}C$ NMR ($CDCl_3$, 75 MHz) δ139.34, 129.16, 128.24, 126.90, 80.75, 76.44, 74.29, 70.58, 69.88, 69.75, 62.47, 58.27, 46.66, 46.47, 42.75, 42.63, 42.51, 42.35, 39.77, 36.87, 35.73, 35.04, 33.77, 32.90, 30.38, 28.71, 27.70, 27.32, 24.89, 24.09, 23.53, 23.36, 23.25, 18.24, 12.62; HRFAB-MS (thioglycerol+$Na^+$ matrix) m/e: ([M+H]$^+$) 627.5199 (23.3%), calcd. 627.5213.

Compound 9: To a solution of 23 (0.18 g, 0.28 mmol) in dry DMF (4 mL) were added NaH (0.224 g, 60% in mineral oil, 5.60 mmol) and 1-bromo octane (0.48 mL, 2.80 mmol). The suspension was stirred under $N_2$ at 65° C. overnight followed by the introduction of $H_2O$ (60 mL) and extraction with ether (4×20 mL). The combined extracts were washed with brine and dried over $Na_2SO_4$. $SiO_2$ chromatography (hexanes and 5% EtOAc in hexanes) afforded the desired product (0.169 g, 80% yield) as a pale yellowish oil. IR (neat) 2927, 2865, 2099, 1478, 1462, 1451, 1350, 1264, 1105 $cm^{-1}$; $^1H$ NMR ($CDCl_3$, 300 MHz) δ3.69–3.35 (series of multiplets, 15 H), 3.26–3.02 (series of multiplets, 4 H), 2.19–2.02 (m, 3 H), 1.97–1.16 (series of multiplets, 37 H), 1.12–0.99 (m, 2 H), 0.92–0.86 (m, 9 H), 0.65 (s, 3 H); $^{13}C$ NMR ($CDCl_3$, 75 MHz) δ80.69, 79.84, 76.13, 71.57, 71.15, 65.07, 64.49, 64.39, 49.08, 48.99, 48.80, 46.68, 46.45, 42.72, 42.05, 39.88, 35.74, 35.49, 35.36, 35.14, 32.42, 32.03, 30.01, 29.85, 29.81, 29.76, 29.67, 29.48, 29.14, 27.92, 27.80, 27.70, 26.58, 26.42, 23.59, 23.09, 22.92, 22.86, 18.11, 14.31, 12.65; HRFAB-MS (thioglycerol+$Na^+$ matrix) m/e: ([M+Na]$^+$) 778.5685 (22.1%), calcd. 778.5683. The triazide (0.169 g, 0.224 mmol) and $LiAlH_4$ (0.025 g, 0.67 mmol) were suspended in anhydrous THF (10 mL) and stirred under $N_2$ at room temperature overnight followed by careful introduction of $Na_2SO_4$ hydrate. After the grey color disappeared, anhydrous $Na_2SO_4$ was added and stirred. The white precipitate was removed by filtration and washed with THF. After removal of solvent, the residue was dissolved in 1 M hydrochloric acid and the aqueous solution was extracted with ether (5 mL) once. The aqueous solution was then made basic by adding 20% aqueous NaOH solution followed by extraction with $Et_2O$ (4×5 mL). The combined extracts were washed, dried and concentrated. The residue was then subject to $SiO_2$ chromatography (MeOH/$CH_2Cl_2$ (1:1) followed by MeOH/$CH_2Cl_2$/$NH_3 \cdot H_2O$ (4:4:1)) to afford the desired product (0.091 g, 60% yield) as a colorless oil. IR (neat) 3361, 2927, 2855, 1576, 1465, 1351, 1105 $cm^{-1}$; $^1H$ NMR ($CD_3OD$, 300 MHz) δ4.86 (bs, 6 H), 3.77–3.72 (m, 1 H), 3.70–3.61 (m, 1 H), 3.57–3.53 (m, 3 H), 3.43–3.38 (m, 4 H), 3.34–3.27 (m, 2 H), 3.18–3.10 (m, 2 H), 2.84–2.71 (m, 6 H), 2.22–2.07 (m, 3 H), 2.00–1.02 (series of multiplets, 39 H), 0.97–0.88 (m, 9 H), 0.71 (s, 3 H); $^{13}C$ NMR ($CD_3OD$, 75 MHz) δ82.20, 81.00, 77.62, 72.52, 72.06, 68.00, 67.92, 67.39, 48.20, 47.53, 44.26, 43.40, 41.42, 41.15, 40.84, 40.35, 36.88, 36.73, 36.42, 36.11, 34.24, 34.05, 33.94, 33.67, 33.17, 30.95, 30.72, 30.62, 29.81, 29.35, 28.87, 28.79, 27.51, 24.57, 23.90, 23.83, 23.44, 18.76, 14.62, 13.07; HRFAB-MS (thioglycerol matrix) m/e: ([M+H]$^+$) 678.6133 (100%), calcd. 678.6149.

Compound 10: A suspension of 23 (0.126 g, 0.196 mmol) and $LiAlH_4$ (0.037 g, 0.98 mmol) in THF (40 mL) was stirred at room temperature under $N_2$ overnight followed by careful addition of $Na_2SO_4 \cdot 10H_2O$. After the grey color in the suspension disappeared, anhydrous $Na_2 SO_4$ was added and stirred until organic layer became clear. The white precipitate was removed by filtration and washed with twice THF. The THF was removed in vacuo, and the residue was subject to $SiO_2$ chromatography (MeOH/$CH_2Cl_2$/$NH_3 \cdot H_2O$ (4:4:1)) to afford the desired product (0.066 g, 60% yield) as a colorless oil. IR (neat) 3365, 2933, 2865, 1651, 1471, 1455, 1339, 1103 $cm^{-1}$; $^1H$ NMR ($CDCl_3$/30% $CD_3OD$, 300 MHz) δ4.43 (bs, 7 H), 3.74–3.68 (m, 1 H), 3.66–3.60 (m, 1 H), 3.57–3.50 (m, 5 H), 3.34–3.25 (M, 2 H), 3.17–3.06 (M, 2 H), 2.84–2.74 (M, 6 H), 2.19–2.01 (M, 3 H), 1.97–0.96 (series of multiplets, 27 H), 0.94 (d, J=7.2 Hz, 3 H), 0.92 (s, 3 H), 0.69 (s, 3 H); $^{13}C$ NMR ($CDCl_3$, 75 MHz) δ80.44, 79.27, 75.77, 66.59, 66.53, 65.86, 62.51, 46.21, 45.84, 42.55, 41.53, 40.09, 39.43, 39.31, 39.02, 35.16, 34.93, 34.86, 34.57, 32.93, 32.71, 31.57, 28.66, 28.33, 27.64, 27.22, 23.04, 22.40, 22.29, 17.60, 11.98; HRFAB-MS (thioglycerol+$Na^+$ matrix) m/e: ([M+H]$^+$) 566.4889 (8.9%), calcd. 566.4897.

Example 5
Syntheses of Compounds 11 and 43–47

Compound 43: Compound 41 was prepared following the method reported by D. H. R. Barton, J. Wozniak, S. Z. Zard, A SHORT AND EFFICIENT DEGRADATION OF THE BILE ACID SIDE CHAIN. SOME NOVEL REACTIONS OF SULPHINES AND A-KETOESTERS, Tetrahedron, 1989, vol. 45, 3741–3754. A mixture of 41 (1.00 g, 2.10 mmol), ethylene glycol (3.52 mL, 63 mmol) and p-TsOH (20 mg, 0.105 mmol) was refluxed in benzene under $N_2$ for 16 hours. Water formed during the reaction was removed by a Dean-Stark moisture trap. The cooled mixture was washed with $NaHCO_3$ solution (50 mL) and extracted with $Et_2O$ (50 mL, 2×30 mL). The combined extracts were washed with brine and dried over anhydrous $Na_2SO_4$. Removal of the solvent gave the product (1.09 g, 100%) as a white glass. IR (neat) 2939, 2876, 1735, 1447, 1377, 1247, 1074, 1057, 1039 $cm^{-1}$; $^1H$ NMR ($CDCl_3$, 300 MHz) δ5.10 (t, J=2.70

Hz, 1 H), 4.92 (d, J=2.69 Hz, 1 H), 4.63–4.52 (m, 1 H), 3.98–3.80 (m, 4 H), 2.32 (t, J=9.51 Hz, 1 H), 2.13 (s, 3 H), 2.08 (s, 3 H), 2.05 (s, 3 H), 2.00–1.40 (series of multiplets, 15 H), 1.34–0.98 (m, 3 H), 1.20 (s, 3 H), 0.92 (s, 3 H), 0.82 (s, 3 H); $^{13}$C NMR (CDCl$_3$, 75 MHz) δ170.69, 170.63, 170.47, 111.38, 75.07, 74.23, 70.85, 64.95, 63.43, 49.85, 44.73, 43.39, 41.11, 37.37, 34.84, 34.80, 34.52, 31.42, 29.18, 27.02, 25.41, 24.16, 22.72, 22.57, 22.44, 21.73, 21.63, 13.40; HRFAB-MS (thioglycerol+Na$^+$ matrix) m/e: ([M+H]$^+$) 521.3106 (38.6%), calcd. 521.3114. The triacetate (1.09 g, 2.10 mmol) was dissolved in MeOH (50 mL). NaOH (0.84 g, 21 mmol) was added to the solution. The suspension was then refluxed under N$_2$ for 24 hours. MeOH was then removed in vacuo and the residue was dissolved in Et$_2$O (100 mL) and washed with H$_2$O, brine, and then dried over anhydrous Na$_2$SO$_4$. The desired product (0.80 g, 96% yield) was obtained as white solid after removal of solvent. m.p. 199–200° C. IR (neat) 3396, 2932, 1462, 1446, 1371, 1265, 1078, 1055 cm$^{-1}$; $^1$H NMR (10% CD$_3$OD in CDCl$_3$, 300 MHz) δ4.08–3.83 (series of multiplets, 9 H), 3.44–3.34 (m, 1 H), 2.41 (t, J=9.28 Hz, 1 H), 2.22–2.10 (m, 2 H), 1.96–1.50 (series of multiplets, 12 H), 1.45–0.96 (series of multiplets, 4 H), 1.32(s, 3 H), 0.89 (s, 3 H), 0.78 (s, 3 H); $^{13}$C NMR (10% CD$_3$OD in CDCl$_3$, 75 MHz) δ112.11, 72.35, 71.57, 68.09, 64.54, 63.24, 49.36, 45.90, 41.48, 41.45, 39.18, 38.79, 35.29, 34.71, 34.45, 29.90, 27.26, 26.60, 23.65, 22.54, 22.44, 22.35, 13.46; HRFAB-MS (thioglycerol+Na$^+$ matrix) m/e: ([M+Na]$^+$) 417.2622 (87.3%), calcd. 417.2617.

Compound 44: To a round-bottom flask were added 43 (0.80 g, 2.03 mmol) and dry THF (100 mL) followed by the addition of NaH (60% in mineral oil, 0.81 g, 20.3 mmol). The suspension was refluxed under N$_2$ for 30 minutes before the addition of allyl bromide (1.75 mL, 20.3 mmol). After 48 hours of reflux, another 10 eq. of NaH and allyl bromide were added. After another 48 hours, TLC showed no intermediates left. Cold water (50 mL) was added to the cooled suspension. The resulted mixture was extracted with Et$_2$O (60 mL, 2×30 mL). The combined extracts were washed with brine and dried over anhydrous Na$_2$SO$_4$. SiO$_2$ column chromatography (6% EtOAc in hexanes) gave the desired product (0.94 g, 90% yield) as a pale yellow oil. IR (neat) 3076, 2933, 2866, 1645, 1446, 1423, 1408, 1368, 1289, 1252, 1226, 1206, 1130, 1080, 1057 cm$^{-1}$; $^1$H NMR (CDCl$_3$, 300 MHz) δ6.02–5.84 (m, 3 H), 5.31–5.04 (m, 6 H), 4.12–4.05 (m, 2 H), 4.01–3.81 (m, 7 H), 3.70 (dd, J=12.94, 5.62 Hz, 1 H), 3.55 (t, J=2.56 Hz, 1 H), 3.33 (d, J=2.93 Hz, 1 H), 3.18–3.08 (m, 1 H), 2.65 (t, J=10.01 Hz, 1 H), 2.32–2.14 (m, 3 H, 1.84–1.45 (series of multiplets, 10 H), 1.41–1.22 (m, 3 H), 1.27 (s, 3 H), 1.14–0.92 (m, 2 H), 0.89 (s, 3 H), 0.75 (s, 3 H); $^{13}$C NMR (CDCl$_3$, 75 MHz) δ136.38, 136.07, 136.00, 116.31, 115.54, 115.38, 112.34, 80.07, 79.22, 75.05, 69.83, 69.34, 68.82, 65.14, 63.24, 48.80, 45.96, 42.47, 42.15, 39.40, 35.55, 35.16, 35.15, 29.04, 28.22, 27.52, 24.21, 23.38, 23.11, 22.95, 22.58, 13.79; HRFAB-MS (thioglycerol+Na$^+$ matrix) m/e: ([M+Na]$^+$) 537.3549 (100%), calcd. 537.3556.

Compound 45: To the solution of 44 (0.94 g, 1.83 mmol) in dry THF (50 mL) was added 9-BBN (0.5 M solution in THF, 14.7 mL, 7.34 mmol) and the mixture was stirred under N$_2$ at room temperature for 12 hours before the addition of 20% NaOH solution (4 mL) and 30% H$_2$O$_2$ solution (4 mL). The resulted mixture was then refluxed for an hour followed by the addition of brine (100 mL) and extracted with EtOAc (4×30 mL). The combined extracts were dried over anhydrous Na$_2$SO$_4$. After the removal of solvent, the residue was purified by SiO$_2$ column chromatography (EtOAc followed by 10% MeOH in CH$_2$Cl$_2$) to give the product (0.559 g, 54% yield) as a colorless oil. IR (neat) 3410, 2933, 2872, 1471, 1446, 1367, 1252, 1086 cm$^{-1}$; $^1$H NMR (CDCl$_3$, 300 MHz) δ4.02–3.52 (series of multiplets, 17 H), 3.41–3.35 (m, 1 H), 3.29 (d, J=2.44 Hz, 1 H), 3.22–3.15 (m, 3 H), 2.58 (t, J=10.01 Hz, 1 H), 2.27–1.95 (m, 3 H), 1.83–1.48 (series of multiplets, 16 H), 1.40–0.93 (series of multiplets, 5 H), 1.27 (s, 3 H), 0.90 (s, 3 H), 0.75 (s, 3 H); $^{13}$C NMR (CDCl$_3$, 75 MHz) δ112.41, 80.09, 79.09, 76.31, 66.70, 66.02, 65.93, 64.80, 63.26, 61.53, 61.25, 60.86, 48.59, 45.80, 42.51, 41.72, 39.10, 35.36, 35.02, 34.98, 32.87, 32.52, 32.40, 28.88, 27.94, 27.21, 24.33, 23.02, 22.84 (2 C's), 22.44, 13.69; HRFAB-MS (thioglycerol+Na$^+$ matrix) m/e: ([M+Na]$^+$) 591.3881 (100%), calcd. 591.3873.

Compound 46: To a solution of 45 (0.559 g, 0.98 mmol) in acetone (40 mL) and water (4 mL) was added PPTS (0.124 g, 0.49 mmol) and the solution was refluxed under N$_2$ for 16 hours. The solvent was removed under reduced pressure. Water (40 mL) was then added to the residue and the mixture was extracted with EtOAc (40 mL, 2×20 mL). The combined extracts were washed with brine, dried and evaporated to dryness. SiO$_2$ column chromatography (8% MeOH in CH$_2$Cl$_2$) of the residue afforded the desired product (0.509 g, 98% yield) as clear oil. IR (neat) 3382, 2941, 2876, 1699, 1449, 1366, 1099 cm$^{-1}$; $^1$H NMR (CDCl$_3$, 300 MHz) δ3.83–3.72 (m, 8 H), 3.66 (t, J=5.62 Hz, 2 H), 3.54 (bs, 2 H), 3.43–3.28 (m, 4 H), 3.24–3.12 (m, 2 H), 2.26–2.00 (m, 4 H), 2.08 (s, 3 H), 1.98–1.50 (series of multiplets, 15 H), 1.42–0.96 (series of multiplets, 6 H), 0.90 (s, 3 H), 0.62 (s, 3 H); $^{13}$C NMR (CDCl$_3$, 75 MHz) δ210.49, 78.87 (2 C's), 76.30, 66.86, 66.18, 65.69, 61.74, 61.43, 60.71, 55.31, 48.05, 43.02, 41.58, 39.53, 35.28, 35.09, 34.96, 32.77, 32.70, 32.31, 31.12, 28.72, 27.88, 27.14, 23.47, 22.75, 22.47, 22.34, 13.86; HRFAB-MS (thioglycerol+Na$^+$ matrix) m/e: ([M+Na]$^+$) 547.3624 (100%), calcd. 547.3611.

Compound 47: To a solution of 46 (0.18 g, 0.344 mmol) in dry CH$_2$Cl$_2$ (10 mL) at 0° C. was added Et$_3$N (0.168 mL, 1.20 mmol) followed by the addition of mesyl chloride (0.088 mL, 1.13 mmol). After 10 minutes, H$_2$O (3 mL) and brine (30 mL) were added. The mixture was extracted with EtOAc (30 mL, 2×10 mL) and the extracts were washed with brine and dried over anhydrous Na$_2$SO$_4$. After removal of solvent, the residue was dissolved in DMSO (5 mL) and NaN$_3$ (0.233 g, 3.44 mmol). The suspension was heated up to 50° C. under N$_2$ for 12 hours. H$_2$O (50 mL) was added to the cool suspension and the mixture was extracted with EtOAc (30 mL, 2×10 mL) and the extracts were washed with brine and dried over anhydrous Na$_2$SO$_4$. SiO$_2$ column chromatography (EtOAc/hexanes 1:5) afforded the product (0.191 g, 88% yield for two steps) as a pale yellow oil. IR (neat) 2933, 2872, 2096, 1702, 1451, 1363, 1263, 1102 cm$^{-1}$; $^1$H NMR (CDCl$_3$, 300 MHz) δ3.72–3.64 (m, 2 H), 3.55–3.24 (series of multiplets, 11 H), 3.18–3.02 (m, 2 H), 2.22–2.02 (m, 4 H), 2.08 (s, 3 H), 1.95–1.46 (series of multiplets, 15 H), 1.38–0.96 (series of multiplets, 6 H), 0.89 (s, 3 H), 0.62 (s, 3 H); $^{13}$C NMR (CDCl$_3$, 75 MHz) δ210.36, 79.69, 79.22, 75.98, 65.08, 64.80, 64.53, 55.31, 48.93, 48.86, 48.76, 48.06, 43.03, 41.91, 39.66, 35.44, 35.31, 35.12, 31.04, 29.77, 29.69, 29.67, 28.99, 28.10, 27.65, 23.60, 22.99, 22.95, 22.50, 14.00; HRFAB-MS (thioglycerol+Na$^+$ matrix) m/e: ([M+Na]$^+$) 622.3820 (100%), calcd. 622.3805.

Compound 11: Compound 47 (0.191 g, 0.319 mmol) was dissolved in dry THF (20 mL) followed by the addition of LiAlH$_4$ (60.4 mg, 1.59 mmol). The grey suspension was stirred under $N_2$ at room temperature for 12 hours. $Na_2SO_4 \cdot 10H_2O$ powder was carefully added. After the grey color in the suspension disappeared, anhydrous $Na_2SO_4$ was added and the precipitate was filtered out. After the removal of solvent, the residue was purified by column chromatography (silica gel, $MeOH/CH_2Cl_2/28\%$ $NH_3 \cdot H_2O$ 3:3:1). After most of the solvent was rotavapped off from the fractions collected, 5% HCl solution (2 mL) was added to dissolve the milky residue. The resulted clear solution was then extracted with $Et_2O$ (2×10 mL). 20% NaOH solution was then added until the solution became strongly basic. $CH_2Cl_2$ (20 mL, 2×10 mL) was used to extract the basic solution. The combined extracts were dried over anhydrous $Na_2SO_4$ and removal of solvent gave the desired product (0.115 g, 69% yield) as a colorless oil. From $^1H$ NMR it appears that this compound was a mixture of two stereoisomers at $C_{20}$ with a ratio of approximately 9:1. The stereoisomers were not separated, but used as recovered. Spectra for the most abundant isomer: IR (neat) 3353, 2926, 2858, 1574, 1470, 1366, 1102 $cm^{-1}$; $^1H$ NMR (20% $CDCl_3$ in $CD_3OD$, 300 MHz) δ4.69 (bs, 7 H), 3.76–3.69 (m, 1 H), 3.63–3.53 (m, 5 H), 3.50–3.40 (m, 1 H), 3.29 (bs, 1 H), 3.18–3.07 (m, 2 H), 2.94–2.83 (m, 1 H), 2.81–2.66 (m, 5 H), 2.23–2.06 (m, 4H), 1.87–1.50 (series of multiplets, 15 H), 1.39–0.96 (series of multiplets, 6 H), 1.11 (d, J=6.10 Hz, 3 H), 0.93 (s, 3 H), 0.75 (s, 3 H); $^{13}C$ NMR (20% $CDCl_3$ in $CD_3OD$, 75 MHz) δ81.46, 80.67, 77.32, 70.68, 67.90, 67.66, 67.18, 50.32, 47.17, 43.30, 43.06, 40.74, 40.64, 40.38, 40.26, 36.31, 36.28, 35.93, 34.30, 34.02, 33.29, 29.63, 29.31, 28.43, 26.10, 24.67, 24.09, 23.96, 23.50, 13.30 for the major isomer; HRFAB-MS (thioglycerol+$Na^+$ matrix) m/e: ($[M+H]^+$) 524.4431(64.2%), calcd. 524.4427.

Example 6
Syntheses of Compounds 12, 48 and 49

Compound 48: To a solution of 23 (0.15 g, 0.233 mmol) in dry $CH_2Cl_2$ (15 mL) at 0° C. was added $Et_3N$ (48.8 μL, 0.35 mmol) followed by the addition of $CH_3SO_2Cl$ (21.7 μL, 0.28 mmol). The mixture was stirred for 15 minutes before $H_2O$ (3 mL) was added. Saturated NaCl solution (20 mL) was then added, and the mixture was extracted with EtOAc (40 mL, 2×20 mL). The combined extracts were washed with brine and dried over anhydrous $Na_2SO_4$. The solvent was rotavapped off and to the residue were added NaBr (0.12 g, 1.17 mmol) and DMF (10 mL). The suspension was heated up to 80° C. under $N_2$ for 2 hours. DMF was removed under vacuum and the residue was chromatographed on silica (EtOAc/hexanes 1:10) to give the desired product (0.191 g, 97% yield) as a pale yellow oil. $^1H$ NMR ($CDCl_3$, 300 MHz) δ3.69–3.35 (series of multiplets, 13 H), 3.28–3.02 (series of multiplets, 4 H), 2.18–2.04 (m, 3 H), 2.00–1.60 (series of multiplets, 16 H), 1.58–0.96 (series of multiplets, 11 H), 0.92 (d, J=6.34 Hz, 3 H), 0.89 (s, 3 H), 0.66 (s, 3 H); $^{13}C$ NMR ($CDCl_3$, 75 MHz) δ80.62, 79.81, 76.08, 65.07, 64.50, 64.34, 49.03, 48.98, 48.79, 46.49, 46.46, 42.73, 42.02, 39.85, 35.47, 35.34, 35.12, 34.79, 34.72, 29.82, 29.80, 29.74, 29.11, 27.91, 27.78, 27.69, 23.55, 23.07, 22.88, 18.10, 12.62; HRFAB-MS (thioglycerol+$Na^+$ matrix) m/e: ($[M-H]^+$) 706.3609 (63.1%), calcd. 706.3591; 704.3616 (52.8%), calcd. 704.3611.

Compound 49: Compound 48 (0.191 g, 0.269 mmol) and 23 (0.295 g, 0.459 mmol) was dissolved in DMF (3 mL, distilled over BaO at 6 mm Hg before use) followed by the addition of NaH (0.054 g, 60% in mineral oil). The suspension was stirred under $N_2$ at room temperature for 24 hours. $H_2O$ (100 mL) was added to quench excess NaH and the mixture was then extracted with $Et_2O$ (40 mL, 3×20 mL) and the combined extracts were washed with brine and dried over anhydrous $Na_2SO_4$. The desired product (0.177 g, 52% yield based on compound 23) was obtained as a pale yellow oil after $SiO_2$ chromatography (EtOAc/hexanes 1:6, then 1:2). IR (neat) 2940, 2862, 2095, 1472, 1456, 1362, 1263, 1113 $cm^{-1}$; $^1H$ NMR($CDCl_3$, 300 MHz) δ3.68–3.35 (series of multiplets, 26 H), 3.28–3.02 (series of multiplets, 8 H), 2.20–2.04 (m, 6 H), 1.96–1.60 (series of multiplets, 30 H), 1.52–0.98 (series of multiplets, 12 H), 0.91 (d, J=6.59 Hz, 6 H), 0.89 (s, 6 H), 0.65 (s, 6 H); $^{13}C$ NMR($CDCl_3$, 75 MHz) δ80.68, 79.83, 76.13, 71.71, 65.06, 64.48, 64.39, 49.08, 48.98, 48.80, 46.64, 46.44, 42.71, 42.04, 39.88, 35.73, 35.49, 35.36, 35.14, 32.41, 29.84, 29.81, 29.76, 29.14, 27.92, 27.78, 27.69, 26.58, 23.59, 23.08, 22.92, 18.12, 12.64.

Compound 12: Compound 49 (0.219 g, 0.173 mmol) was dissolved in dry THF (10 mL) followed by the addition of $LiAlH_4$ (65 mg, 1.73 mmol). The grey suspension was stirred under $N_2$ at room temperature for 12 hours. $Na_2SO_4 \cdot 10H_2O$ powder was carefully added. After the grey color in the suspension disappeared, anhydrous $Na_2SO_4$ was added and the precipitate was filtered out. After the removal of solvent, the residue was purified by column chromatography (silica gel, $MeOH/CH_2Cl_2/28\%$ $NH_3 \cdot H_2O$ 2.5:2.5:1). After most of the solvent was rotavapped off from the fractions collected, 5% HCl solution (2 mL) was added to dissolve the milky residue. The resulted clear solution was then extracted with $Et_2O$ (2×10 mL). 20% NaOH solution was then added until the solution became strongly basic. $CH_2Cl_2$ (20 mL, 2×10 mL) was used to extract the basic solution. The combined extracts were dried over anhydrous $Na_2SO_4$ and removal of solvent gave the desired product (0.147 g, 76% yield) as a white glass. IR (neat) 3364, 3287, 2934, 2861, 1596, 1464, 1363, 1105 $cm^{-1}$; $^1H$ NMR (20% $CDCl_3$ in $CD_3OD$, 500 MHz) δ4.74 (bs, 12 H), 3.75–3.70 (m, 2 H), 3.65–3.61 (m, 2 H), 3.57–3.52 (m, 6 H), 3.40 (t, J=3.60 Hz, 4 H), 3.30 (bs, 4 H), 3.16–3.10 (m, 4 H), 2.84–2.73 (m, 12 H), 2.18–2.07 (m, 6 H), 1.97–1.61 (series of multiplets, 30 H), 1.58–0.98 (series of multiplets, 24 H), 0.95 (d, J=6.84 Hz, 6 H), 0.94 (s, 6 H), 0.70 (s, 6 H); $^{13}C$ NMR (20% $CDCl_3$ in $CD_3OD$, 125 MHz) δ81.70, 80.52, 77.09, 72.34, 67.75 (2 C's), 67.07, 47.80, 47.13, 43.76, 42.87, 41.20, 40.65, 40.58, 40.14, 36.43, 36.25, 36.08, 35.77, 34.15, 33.87 (2 C's), 33.18, 29.55, 28.92, 28.47, 28.42, 27.25, 24.27, 23.54, 23.41, 18.70, 13.07; HRFAB-MS (thioglycerol+$Na^+$ matrix) m/e: ($[M+H]^+$) 1113.9625 (68.8%), calcd. 1113.9610.

Example 7
Syntheses of Compounds 111–113 and 116 a–d

Compounds 116a–d: Representative procedure: preparation of 116b. NaH (0.06 g, 60% in mineral oil, 1.49 mmol) and propyl bromide (0.136 mL, 1.49 mmol) were added to a DMF solution of compound 23 (described in Li et al., *J. Am. Chem. Soc.* 1998, 120, 2961) (0.096 g, 0.149 mmol). The suspension was stirred under $N_2$ for 24 hr. $H_2O$ (20 mL) was added, and the mixture was extracted with hexanes (3×10 mL). The combined extracts were dried over $Na_2SO_4$ and concentrated in vacuo. Silica gel chromatography (10% EtOAc in hexanes) afforded the desired product (92 mg, 90% yield) as a pale yellow oil. 1H NMR ($CDCl_3$, 500 MHz) δ3.68–3.64 (m, 1 H), 3.61–3.57 (m, 1 H), 3.52 (t, J=6.1 Hz, 2 H), 3.49 (bs, 1 H), 3.46–3.35 (m, 10 H), 3.25 (d, J=2.4 Hz, 1 H), 3.23–3.19 (m, 1 H), 3.16–3.11 (m, 1 H), 3.09–3.03 (m, 1 H), 2.17–2.03 (m, 3 H), 1.95–1.55 (m, 17 H), 1.51–1.40 (m, 4 H), 1.38–1.17 (m, 5 H), 1.11–0.96 (m, 3 H), 0.93–0.89 (m, 9 H), 0.65 (s, 3 H); $^{13}C$ NMR ($CDCl_3$, 75 MHz) δ80.64, 79.79, 76.08, 72.67, 71.59, 65.01, 64.44, 64.33, 49.04, 48.94, 48.75, 46.61, 46.40, 42.68, 42.00, 39.83, 35.72, 35.45, 35.30, 35.10, 32.38, 29.81, 29.77, 29.72, 29.09, 27.88, 27.76, 27.65, 26.52, 23.55, 23.12, 23.04, 22.87, 12.60, 10.79; HRFAB-MS (thioglycerol+Na$^+$ matrix) m/e: ([M+Na]$^+$) 708.4910 (23.5%), calcd. 708.4920.

Compounds 111–113: Representative procedure: preparation of 112. Compound 116b (0.092 g, 0.134 mmol) was dissolved in THF (10 mL) followed by the addition of LiAlH$_4$ (0.031 g, 0.81 mmol). The suspension was stirred under N$_2$ for 12 hr. Na$_2$SO$_4$.10H$_2$O (~1 g) was then carefully added. After the gray color in the suspension dissipated, anhydrous Na$_2$SO$_4$ was added, and the precipitate was removed by filtration. Concentration and silica gel chromatography (CH$_2$Cl$_2$/MeOH/28% NH$_3$.H$_2$O 12:6:1, then 10:5:1) yielded a glass which was dissolved in 1 M HCl (2 mL). The resulting clear solution was washed with Et$_2$O (2×10 mL). 20% NaOH solution was added to the aqueous phase until the solution became strongly basic. CH$_2$Cl$_2$ (3×10 mL) was used to extract the basic solution. The combined extracts were dried over anhydrous Na$_2$SO$_4$ and concentrated in vacuo to give the desired product (0.045 g, 55% yield) as a white glass. 112: $^1$H NMR (20% CDCl$_3$ in CD$_3$OD, 500 MHz) δ4.73 (bs, 6 H), 3.74–3.70 (m, 1 H), 3.65–3.61 (m, 1 H), 3.55 (t, J=6.3 Hz, 2 H), 3.42–3.38 (m, 4 H), 3.33–3.30 (m, 2 H), 3.16–3.10 (m, 2 H), 2.83–2.73 (m, 6 H), 2.18–2.06 (m, 3 H), 1.96–1.20 (series of multiplets, 26 H), 1.12–0.98 (m, 3 H), 0.95–0.92 (m, 9 H), 0.70 (s, 3 H); $^{13}$C NMR (~20% CDCl$_3$ in CD$_3$OD, 75 MHz) δ81.67, 80.49, 77.04, 73.44, 72.28, 67.77, 67.71, 67.06, 47.74, 47.08, 43.75, 42.82, 41.21, 40.60, 40.56, 40.12, 36.47, 36.19, 36.04, 35.74, 34.09, 33.82, 33.78, 33.16, 29.49, 28.87, 28.43, 27.18, 24.22, 23.66, 23.49, 23.40, 18.64, 13.04, 11.03; HRFAB-MS (thioglycerol+Na$^+$ matrix) m/e: ([M+H]$^+$) 608.5348 (100%), calcd. 608.5330. 111: $^1$H NMR (~20% CDCl$_3$ in CD$_3$OD, 500 MHz) δ4.79 (bs, 6H), 3.74–3.71 (m, 1 H), 3.66–3.62 (m, 1 H), 3.55 (t, J=6.1 Hz, 2 H), 3.52 (bs, 1 H), 3.38–3.28 (series of multiplets, 4 H), 3.33 (s, 3 H), 3.16–3.10 (m, 2H), 2.83–2.72 (m, 6 H), 2.19–2.07 (m, 3 H), 1.97–1.62 (series of multiplets, 15 H), 1.58–1.20 (series of multiplets, 9 H), 1.13–0.98 (m, 3 H), 0.95 (d, J=6.3 Hz, 3 H), 0.93 (s, 3 H), 0.70 (s, 3 H); $^{13}$C NMR (~20% CDCl$_3$ in CD$_3$OD, 75 MHz) δ81.82, 80.65, 77.20, 74.43, 67.85, 67.18, 58.90, 47.80, 47.22, 43.91, 43.01, 41.31, 40.78, 40.69, 40.22, 36.63, 36.35, 36.18, 35.86, 34.27, 33.97, 33.26, 29.60, 29.03, 28.58, 28.53, 27.14, 24.33, 23.61, 23.45, 18.68, 13.06; HRFAB-MS (thioglycerol+Na$^+$ matrix) m/e: ([M+Na]$^+$) 602.4855 (100%), calcd. 602.4873. 113: $^1$H NMR (~50% CDCl$_3$ in CD$_3$OD, 500 MHz) δ4.08 (bs, 6 H), 3.71–3.67 (m, 1 H), 3.62–3.58 (m, 1 H), 3.53 (t, J=6.3 Hz, 2 H), 3.49 (bs, 1 H), 3.43–3.38 (m, 4 H), 3.31–3.27 (m, 2 H), 3.14–3.07 (m, 2 H), 2.83–2.73 (m, 6 H), 2.16–2.03 (m, 3 H), 1.93–1.17 (series of multiplets, 30 H), 1.10–0.96 (m, 3 H), 0.93–0.89 (m, 9 H), 0.67 (s, 3 H); $^{13}$C NMR (~50% CDCl$_3$ in CD$_3$OD, 75 MHz) δ80.51, 79.35, 75.85, 71.29, 70.83, 66.73, 66.62, 65.96, 46.68, 45.98, 42.59, 41.63, 40.20, 39.53, 39.43, 39.21, 35.34, 35.04, 35.00, 34.71, 33.11, 32.90, 32.82, 32.00, 29.15, 28.49, 28.15, 27.75, 27.35, 26.22, 23.18, 22.60, 22.45, 22.34, 17.77, 13.75, 12.22; HRFAB-MS (thioglycerol+Na$^+$ matrix) m/e: ([M+H]$^+$) 636.5679 (100%), calcd. 636.5669.

Example 8
Syntheses of Compounds 106 and 124

Compound 124: Compound 47 (0.256 g, 0.489 mmol) was dissolved in CH$_2$Cl$_2$ (10 mL), and cooled to 0° C. followed by the addition of Na$_2$HPO$_4$ (0.69 g, 4.89 mmol) and urea-hydrogen peroxide complex (UHP) (0.069 g, 0.733 mmol). Trifluoroacetic anhydride (TFAA) (0.138 mL, 0.977 mmol) was then added dropwise. The suspension was stirred for 12 hr, and additional UHP (23 mg, 0.25 mmol) and TFAA (0.069 mL, 0.49 mmol) were added. After another 12 hr, H$_2$O (30 mL) was added, and the resulting mixture was extracted with EtOAc (3×20 mL). The combined extracts were washed with brine (50 mL), dried over anhydrous Na$_2$SO$_4$, and concentrated in vacuo. SiO$_2$ chromatography (EtOAc/hexanes 1:5) afforded the desired product (0.145 g, 55% yield) as a colorless oil. $^1$H NMR (CDCl$_3$, 300 MHz) δ5.21 (dd, J=9.3 and 7.3 Hz, 1 H), 3.70–3.57 (m, 2 H), 3.55 (t, J=6.0 Hz, 2 H), 3.43–3.37 (m, 6 H), 3.32–3.25 (m, 3 H), 3.17–3.02 (m, 2 H), 2.28–2.05 (m, 4 H), 2.03 (s, 3 H), 1.86–1.19 (series of multiplets, 19 H), 0.97 (dd, J=14.5 and 3.3 Hz, 1 H), 0.90 (s, 3 H), 0.78 (s, 3 H); $^{13}$C NMR (CDCl$_3$, 75 MHz) δ171.08, 79.71, 78.03, 75.72, 75.53, 65.41, 65.04, 64.53, 48.79, 48.70, 46.49, 41.92, 39.44, 37.81, 35.45, 35.22, 35.10, 29.73, 29.63, 28.89, 28.33, 27.50, 27.34, 23.39, 22.97, 22.92, 21.28, 12.72; HRFAB-MS (thioglycerol+Na$^+$ matrix) m/e: ([M−H]$^+$) 614.3798 (24.5%), calcd. 614.3778.

Compound 106: Compound 124 (0.145 g, 0.236 mmol) was dissolved in CH$_2$Cl$_2$ (2 mL) and MeOH (1 mL). 20% NaOH solution (0.2 mL) was added. The mixture was stirred for 12 hr, and anhydrous Na$_2$SO$_4$ was used to remove water. After concentration in vacuo, the residue was purified by silica gel chromatography (EtOAc/hexanes 1:3) to afford the desired product (0.124 g, 92% yield) as a colorless oil. $^1$H NMR (CDCl$_3$, 300 MHz) δ4.29 (bs, 1 H), 3.69–3.60 (m, 2 H), 3.52 (t, J=6.0 Hz, 2 H), 3.45–3.32 (m, 8 H), 3.26 (d, J=2.7 Hz, 1 H), 3.17–3.02 (m, 2 H), 2.19–1.94 (m, 4 H), 1.90–1.62 (series of multiplets, 13 H), 1.57–1.20 (series of multiplets, 7 H), 0.97 (dd, J=14.3 and 3.1 Hz, 1 H), 0.90 (s, 3 H), 0.73 (s, 3 H); $^{13}$C NMR (CDCl$_3$, 75 MHz) δ79.69, 78.03, 75.47, 73.38, 65.46, 65.00, 64.47, 48.87, 48.68, 46.83, 41.93, 39.71, 37.87, 35.43, 35.20, 35.09, 29.96, 29.69, 29.59, 29.53, 28.89, 28.44, 27.48, 23.72, 22.91, 22.71, 11.77. The alcohol (0.124 g, 0.216 mmol) was dissolved in dry THF (20 mL) followed by the addition of LiAlH$_4$ (33 mg, 0.866 mmol). The gray suspension was stirred under N$_2$ for 12 hr. Na$_2$SO$_4$.10 H$_2$O (~2 g) was carefully added. After the gray color in the suspension dissipated, anhydrous Na$_2$SO$_4$ was added and the precipitate was removed by filtration. After the removal of solvent, the residue was purified by column chromatography (SiO$_2$, MeOH/CH$_2$Cl$_2$/28% NH3.H$_2$O 2.5:2.5:1). After concentration of the relevant fractions, 1 M HCl (2 mL) was added to dissolve the milky residue. The resulting clear solution was washed with Et$_2$O (2×10 mL). To the aqueous phase, 20% NaOH solution was added until the solution became strongly basic. CH$_2$Cl$_2$ (20 mL, 2×10 mL) was used to extract the basic solution. The combined extracts were dried over anhydrous Na$_2$SO$_4$ and removal of solvent gave the desired product (0.050 g, 47% yield) as a colorless oil. $^1$H NMR (20% CDCl$_3$ in CD$_3$OD, 300 MHz) δ4.77 (s, 7 H), 4.25 (t, J=8.5 Hz, 1 H), 3.75–3.68 (m, 1 H), 3.66–3.58 (m, 1 H), 3.55 (t, J=6.1 Hz, 2 H), 3.48–3.41 (m, 1 H), 3.34 (bs, 1 H), 3.30 (d, J=3.6 Hz, 1 H), 3.17–3.08 (m, 2 H), 2.86–2.70 (m, 6 H), 2.20–1.91 (m, 4 H), 1.88–1.16 (series of multiplets, 19 H), 1.00 (dd, J=14.2 and 3.0 Hz, 1 H), 0.93 (s, 3 H), 0.73 (s, 3 H); $^{13}$C NMR (20% CDCl$_3$ in CD$_3$OD, 75 MHz) δ80.62, 79.12, 76.74, 73.77, 68.50, 67.79, 67.17, 47.69, 43.04, 40.76, 40.64, 40.62, 40.22, 39.01, 36.32, 36.25, 35.94, 34.27, 33.97, 33.72, 30.13, 29.53, 28.43, 24.48, 23.58, 23.40, 12.38; HRFAB-MS (thioglycerol+Na$^+$ matrix) m/e: ([M+H]$^+$) 496.4108 (100%), calcd. 496.4114.

Example 9
Syntheses of Compounds 109, and 126–129

Compound 126: Compound 125 (2.30 g, 3.52 mmol) was dissolved in MeOH (50 mL) and $CH_2Cl_2$ (100 mL). A small amount of $Et_3N$ was added, and the solution was cooled to −78° C. Ozone was bubbled through the solution until a blue color persisted. $Me_2S$ (4 mL) was introduced followed by the addition of $NaBH_4$ (0.266 g, 0.703 mmol) in MeOH (10 mL). The resulting solution was allowed to warm and stir overnight. The solution was concentrated in vacuo, and brine (60 mL) was added. The mixture was extracted with EtOAc (40 ml, 2×30 mL), and the combined extracts were washed with brine and dried over anhydrous $Na_2SO_4$. Silica gel chromatography (EtOAc) afforded the product (1.24 g, 76% yield) as a white solid. m.p. 219–220° C.; $^1H$ NMR ($CDCl_3$, 300 MHz) δ5.10 (t, J=2.8 Hz, 1 H), 4.90 (d, J=2.7 Hz, 1 H), 3.73–3.59 (m, 2 H), 3.56–3.44 (m, 1 H), 2.13 (s, 3 H), 2.09 (s, 3 H), 2.07–0.95 (series of multiplets, 23 H), 0.91 (s, 3 H), 0.83 (d, J=6.3 Hz, 3 H), 0.74 (s, 3 H); $^{13}C$ NMR ($CDCl_3$, 75 MHz) δ170.84, 170.82, 75.63, 71.77, 71.03, 60.73, 48.10, 45.26, 43.54, 41.16, 38.78, 37.89, 35.00, 34.43, 32.26, 31.50, 30.60, 29.07, 27.50, 25.70, 22.96, 22.71, 21.81, 21.63, 18.18, 12.35; HRFAB-MS (thioglycerol+$Na^+$ matrix) m/e: ([M+H]$^+$) 465.3197 (20%), calcd. 465.3216.

Compound 127: Compound 126 (1.24 g, 2.67 mmol) was dissolved in MeOH (30 mL), and NaOH (0.54 g, 13.4 mmol) was added. The suspension was refluxed under $N_2$ for 24 hr. The MeOH was removed in vacuo followed by the addition of $H_2O$ (50 mL). The precipitate was filtered, washed with $H_2O$ and then dried in vacuo to give a white solid (1.02 g). This solid was dissolved in DMF (40 mL) followed by the sequential addition of $NEt_3$ (1.12 mL, 8.02 mmol), DMAP (16.3 mg, 0.13 mmol) and trityl chloride (1.49 g, 5.34 mmol). The suspension was stirred under $N_2$ for 12 hr and then heated up to 50° C. for 24 hr. $H_2O$ (100 mL) was added to the cooled suspension, and the mixture was extracted with EtOAc (3×50 mL). The combined extracts were washed with brine (100 mL), dried over anhydrous $Na_2SO_4$, and concentrated in vacuo. Silica gel chromatography (EtOAc) afforded the product (1.20 g, 72% yield) as a pale yellow glass. To this glass was added dry THF (80 mL) and NaH (60% in mineral oil, 0.77 g, 19.3 mmol). The suspension was refluxed under $N_2$ for half an hour before the introduction of allylbromide (1.67 mL, 19.3 mmol). After 48 hr at reflux, another 10 eq. of NaH and allylbromide were introduced. After another 48 hr, the reaction mixture was cooled and $H_2O$ (100 mL) was slowly added. The resulting mixture was extracted with hexanes (3×50 mL), and the combined extracts were washed with brine (100 mL) and dried over anhydrous $Na_2SO_4$. Silica gel chromatography (5% EtOAc in hexanes) afforded the product (1.27 g, 64% yield for all three steps) as a clear glass. $^1H$ NMR ($CDCl_3$, 300 MHz) δ7.46–7.43 (m, 6 H), 7.29–7.16 (m, 9 H), 5.98–5.81 (m, 3 H), 5.29–5.18 (m, 3 H), 5.14–5.03 (m, 3 H), 4.11–3.97 (m, 4 H), 3.75–3.67 (m, 2 H), 3.49 (bs, 1 H), 3.32–3.13 (d, J=2.4 Hz, 1 H), 3.20–3.13 (m, 2 H), 3.00 (m, 1 H), 2.33–2.12 (m, 3 H), 2.03–0.92 (series of multiplets, 19 H), 0.88 (s, 3 H), 0.78 (d, J=6.6 Hz, 3 H), 0.65 (s, 3 H); $^{13}C$ NMR ($CDCl_3$, 75 MHz) δ144.71, 136.08, 136.04, 135.94, 128.80, 127.76, 126.86, 116.30, 115.57, 86.53, 80.77, 79.20, 74.96, 69.42, 69.34, 68.81, 62.00, 46.87, 46.48, 42.67, 42.11, 39.90, 36.15, 35.50, 35.14, 35.10, 33.23, 28.99, 28.09, 27.75, 27.56, 23.36, 23.32, 23.12, 18.24, 12.66; HRFAB-MS (thioglycerol+$Na^+$ matrix) m/e: ([M+Na]$^+$) 765.4875 (100%), calcd. 765.4859.

Compound 128: To a THF (40 mL) solution of 127 (1.27 g, 1.71 mmol) was added 9-BBN (0.5 M solution in THF, 17.1 mL). The mixture was stirred for 12 hr before the addition of NaOH (20% solution, 10 mL) and $H_2O_2$ (30% solution, 10 mL). The resulted mixture was refluxed for 1 hr followed by the addition of brine (100 mL) and extraction with EtOAc (4×30 mL). The combined extracts were dried over anhydrous $Na_2SO_4$ and concentrated in vacuo. Silica gel chromatography (5% MeOH in $CH_2Cl_2$) afforded the product (1.26 g, 93% yield) as a clear glass. $^1H$ NMR (5% $CD_3OD$ in $CDCl_3$, 300 MHz) δ7.46–7.43 (m, 6 H), 7.32–7.20 (m, 9 H), 3.94 (s, 3 H), 3.78–3.56 (m, 10 H), 3.48 (bs, 1 H), 3.32–3.26 (m, 2 H), 3.24–3.12 (m, 3 H), 3.00 (dd, J=8.2 and 6.1 Hz, 1 H), 2.23–1.96 (m, 3 H), 1.90–0.95 (series of multiplets, 25 H), 0.90 (s, 3 H), 0.77 (d, J=6.6 Hz, 3 H), 0.66 (s, 3 H); $^{13}C$ NMR (5% $CD_3OD$ in $CDCl_3$, 75 MHz) δ144.52, 128.64, 127.64, 126.76, 86.43, 80.55, 79.31, 77.65, 77.23, 76.80, 76.06, 66.17, 66.01, 65.41, 61.93, 61.20, 60.73, 60.39, 47.29, 46.08, 42.65, 41.62, 39.49, 36.02, 35.10, 34.89, 34.77, 32.89, 32.71, 32.41, 32.26, 28.68, 27.70, 27.51, 27.19, 23.26, 22.66, 22.50, 18.23, 12.34; HRFAB-MS (thioglycerol+$Na^+$ matrix) m/e: ([M+Na]$^+$) 819.5169 (100%), calcd. 819.5099.

Compound 129: To a $CH_2Cl_2$ (50 mL) solution of compound 128 (1.26 g, 1.58 mmol) at 0° C. was added $Et_3N$ (0.92 mL, 6.60 mmol) followed by mesyl chloride (0.47 mL, 6.05 mmol). After 15 minutes, $H_2O$ (10 mL) was followed by brine (80 mL). The mixture was extracted with EtOAc (60 mL, 2×30 mL) and the combined extracts were dried over anhydrous $Na_2SO_4$. After removal of solvent in vacuo, the residue was dissolved in DMSO (10 mL) and $NaN_3$ (1.192 g, 18.3 mmol) was added. The suspension was heated to 60° C. under $N_2$ overnight. $H_2O$ (100 mL) was added, and the mixture was extracted with EtOAc (3×40 mL). The combined extracts were washed with brine and dried over anhydrous $Na_2SO_4$. Removal of the solvent in vacuo afforded a pale yellow oil. The oil was dissolved in MeOH (10 mL) and $CH_2Cl_2$ (20 mL) and TsOH (17.4 mg, 0.092 mmol) was added. After 12 hr, saturated aqueous $NaHCO_3$ (20 mL) and brine (50 mL) were added and the mixture was extracted with EtOAc (3×40 mL). The combined extracts were washed with brine (50 mL) and dried over anhydrous $Na_2SO_4$. Silica gel chromatography (EtOAc/hexanes 1:3) afforded the desired product (0.934, 94%) as a pale yellow oil. $^1H$ NMR ($CDCl_3$, 500 MHz) δ3.75–3.70 (m, 1 H), 3.68–3.63 (m, 2 H), 3.62–3.57 (m, 1 H), 3.53 (t, J=6.1 Hz, 2 H), 3.50 (bs, 1 H), 3.46–3.38 (m, 6 H), 3.26 (d, J=2.4 Hz, 1 H), 3.24–3.20 (m, 1 H), 3.16–3.12 (m, 1 H), 3.10–3.04 (m, 1 H), 2.17–2.04 (m, 3 H), 1.96–1.63 (m, 14 H), 1.53–1.45 (m, 3 H), 1.35–1.20 (m, 7 H), 1.08–1.00 (m, 1 H), 0.97–0.88 (m, 1 H), 0.94 (d, J=6.8 Hz, 3 H), 0.89 (s, 3 H), 0.67 (s, 3 H); $^{13}C$ NMR ($CDCl_3$, 75 MHz) δ80.64, 79.81, 76.06, 65.05, 64.49, 64.34, 61.03, 49.02, 48.98, 48.78, 46.93, 46.53, 42.76, 42.01, 39.83, 39.14, 35.46, 35.33, 35.12, 32.97, 29.79, 29.73, 29.10, 27.90, 27.68, 23.56, 23.06, 22.88, 18.24, 12.60; HRFAB-MS (thioglycerol+$Na^+$ matrix) m/e: ([M+Na]$^+$) 652.4285 (100%), calcd. 652.4295.

Compound 109: Compound 129 (0.245 g, 0.391 mmol) was dissolved in THF (30 mL) followed by the addition of $LiAlH_4$ (59 mg, 1.56 mmol). The gray suspension was stirred under $N_2$ 12 hr. $Na_2SO_4 \cdot 10H_2O$ powder (~1 g) was carefully added. After the gray color in the suspension dissipated, anhydrous $Na_2SO_4$ was added and the precipitate was removed by filtration. After the removal of solvent, the residue was purified by silica gel chromatography ($CH_2Cl_2$/MeOH/28% $NH_3 \cdot H_2O$ 10:5:1 then 10:5:1.5). The solvent was removed from relevant fractions, and 1 M HCl (4 mL) was added to dissolve the residue. The resulting clear solution was extracted with $Et_2O$ (3×10 mL). 20% NaOH solution was added until the solution became strongly basic. CH$_2$Cl$_2$ (4×10 mL) was used to extract the basic solution. The combined extracts were dried over anhydrous Na$_2$SO$_4$, and removal of solvent in vacuo gave the desired product (0.15 g, 71% yield) as a colorless oil. $^1$H NMR (~20% CD$_3$OD in CDCl$_3$, 500 MHz) δ4.73 (bs, 7 H), 3.74–3.70 (m, 1 H), 3.65–3.60 (m, 2 H), 3.56–3.52 (m, 4 H), 3.31–3.28 (m, 2 H), 3.16–3.09 (m, 2 H), 2.82–2.71 (m, 6 H), 2.19–2.06 (m, 3 H), 1.97–1.66 (series of multiplets, 15 H), 1.58–1.48 (m, 3 H), 1.38–0.98 (m, 7 H), 0.96 (d, J=6.8 Hz, 3 H), 0.93 (s, 3 H), 0.71 (s, 3 H); $^{13}$C NMR (~20% CD$_3$OD in CDCl$_3$, 75 MHz) δ81.80, 80.60, 77.17, 67.88, 67.86, 67.18, 60.73, 48.11, 47.28, 43.93, 42.99, 41.34, 40.76, 40.72, 40.24, 39.70, 36.33, 36.18, 35.86, 34.29, 33.99, 33.96, 33.83, 29.60, 29.00, 28.57, 28.54, 24.33, 23.59, 23.48, 18.86, 13.04; HRFAB-MS (thioglycerol+Na$^+$ matrix) m/e: ([M+H]$^+$) 552.4756 (100%), calcd. 552.4772.

Example 10
Syntheses of Compounds 108 and 130

Compound 130: o-NO$_2$C$_6$H$_4$SeCN (0.094 g, 0.21 mmol) and Bu$_3$P (0.095 mL, 0.38 mmol) were stirred in dry THF (5 mL) at 0° C. for ½ hr followed by the addition of compound 129 (0.10 g, 0.159 mmol) in THF (2 mL). The suspension was stirred for 1 hr followed by the addition of H$_2$O$_2$ (30% aqueous solution, 2 mL). The mixture was stirred for 12 hr followed by extraction with hexanes (4×10 mL). The combined extracts were dried over anhydrous Na$_2$SO$_4$. The desired product (0.035 g, 36% yield) was obtained as pale yellowish oil after silical gel chromatography (10% EtOAc/hexanes). $^1$H NMR (CDCl$_3$, 500 MHz) δ5.73–5.66 (ddd, J=17.1, 10.2, 8.3 Hz, 1 H), 4.90 (dd, J=17.1, 2.0 Hz, 1 H), 4.82 (dd, J=10.2 Hz, 1.96 Hz, 1 H), 3.68–3.64 (m, 1 H), 3.62–3.58 (m, 1 H), 3.54–3.26 (m, 9 H), 3.25–3.22 (m, 2 H), 3.15–3.11 (m, 1 H), 3.10–3.04 (m, 1 H), 2.17–1.62 (series of multiplets, 18 H), 1.51–1.43 (m, 2 H), 1.35–1.18 (m, 4 H), 1.06–0.91 (m, 2 H), 1.02 (d, J=6.3 Hz, 3 H), 0.90 (s, 3 H), 0.68 (s, 3 H); $^{13}$C NMR (CDCl$_3$, 75 MHz) δ145.50, 111.72, 80.60, 79.82, 76.09, 65.06, 64.50, 64.45, 49.05, 48.97, 48.79, 46.43, 46.13, 42.76, 42.03, 41.30, 39.84, 35.49, 35.34, 35.15, 29.82, 29.80, 29.75, 29.11, 28.00, 27.84, 27.68, 23.56, 23.08, 22.95, 19.79, 12.87; HRFAB-MS (thioglycerol+Na$^+$ matrix) m/e: ([M+Na]$^+$) 634.4167 (90.6%), calcd. 634.4169.

Compound 108: Compound 130 (0.105 g, 0.172 mmol) was dissolved in CH$_2$Cl$_2$ (5 mL) and MeOH (5 mL) at −78° C. O$_3$ was bubbled into the solution for ca. 20 min. Me$_2$S (1 mL) was added followed, and the solvent was removed in vacuo. The residue was dissolved in THF (15 mL), and LiAlH$_4$ (0.033 g, 0.86 mmol) was added. The suspension was stirred for 12 hr. Na$_2$SO$_4$·10H$_2$O (~2 g) was carefully added. After the gray color of the suspension dissipated, anhydrous Na$_2$SO$_4$ was added and the precipitate was removed by filtration. Concentration and silica gel chromatography (CH$_2$Cl$_2$/MeOH/28% NH$_3$·H$_2$O 10:5:1.5 then 9:6:1.8) yielded a white glass. To this material was added 1 M HCl (4 mL). The resulting clear solution was washed with Et$_2$O (3×10 mL). 20% NaOH solution was added to the aqueous phase until the solution became strongly basic. CH$_2$Cl$_2$ (4×10 mL) was used to extract the basic solution. The combined extracts were dried over anhydrous Na$_2$SO$_4$ and removal of solvent gave the desired product (0.063 g, 68% yield) as a colorless oil. $^1$H NMR (~10% CD$_3$OD in CDCl$_3$, 500 MHz) δ4.76 (bs, 7 H), 3.75–3.71 (m, 1 H), 3.66–3.62 (m, 1 H), 3.58–3.52 (m, 4 H), 3.33–3.29 (m, 2 H), 3.22 (dd, J=10.5 and 7.6 Hz, 1 H), 3.15–3.09 (m, 1 H), 2.81 (t, J=6.8 Hz, 2 H), 2.76–2.71 (m, 4 H), 2.19–2.08 (m, 3 H), 2.00–1.66 (series of multiplets, 14 H), 1.58–1.45 (m, 3 H), 1.40–1.08 (m, 5 H), 1.03 (d, J=6.8 Hz, 3 H), 1.02–0.96 (m, 1 H), 0.93 (s, 3 H), 0.72 (s, 3 H); $^{13}$C NMR (10% CD$_3$OD in CDCl$_3$, 75 MHz) δ81.74, 80.64, 77.23, 67.95, 67.87, 67.18, 47.32, 44.59, 43.72, 43.01, 41.26, 40.80, 40.71, 40.23, 40.02, 36.36, 36.20, 35.87, 34.27, 33.99, 33.90, 29.60, 29.05, 28.58, 28.08, 24.49, 23.62, 23.46, 16.84, 13.12; HRFAB-MS (thioglycerol+Na$^+$ matrix) m/e: ([M+H]$^+$) 538.4578 (4.7%), calcd. 538.4584.

Example 11
Syntheses of Compounds 132–135

Compound 132: Compound 115 (0.118 g, 0.183 mmol) was dissolved in dry CH$_2$Cl$_2$ (10 mL), and SO$_3$ pyridine complex (0.035 g, 0.22 mmol) was added. The suspension was stirred for 12 hr. The solvent was removed in vacuo to give white powder. To the white powder was added 1 M HCl (10 mL) and the resulting mixture was extracted with CH$_2$Cl$_2$ (4×10 mL). The combined extracts were dried over anhydrous Na$_2$SO$_4$. The desired product (0.11 g, 84%) was obtained as a pale yellow oil after silica gel chromatography (10% MeOH in CH$_2$Cl$_2$). $^1$H NMR (~10% CD$_3$OD in CDCl$_3$, 500 MHz) δ4.03 (t, J=6.8 Hz, 2 H), 3.69–3.65 (m, 1 H), 3.62–3.58 (m, 1 H), 3.55 (t, J=6.1 Hz, 2 H), 3.51 (bs, 1 H), 3.46–3.38 (m, 6 H), 3.27 (d, J=2.4 Hz, 1 H), 3.26–3.21 (m, 1 H), 3.18–3.07 (m, 2 H), 2.18–2.03 (m, 3 H), 1.95–1.47 (series of multiplets, 19 H), 1.40–0.96 (series of multiplets, 9 H), 0.92 (d, J=6.8 Hz, 3 H), 0.91 (s, 3 H), 0.66 (s, 3 H); $^{13}$C NMR (10% CD$_3$OD in CDCl$_3$, 75 MHz) δ80.43, 79.68, 75.87, 69.30, 64.82, 64.32, 64.14, 48.78, 48.73, 48.50, 46.44, 46.21, 42.49, 41.76, 39.61, 35.36, 35.17, 35.06, 34.85, 31.73, 29.53, 29.46, 29.44, 28.84, 27.68, 27.48, 27.38, 25.91, 23.30, 22.75, 22.66, 17.70, 12.32; HRFAB-MS (thioglycerol+Na$^+$ matrix) m/e: ([M−H+2Na]$^+$) 768.3831 (100%), calcd. 768.3843. The azides were reduced by treating the triazide (0.11 g, 0.15 mmol) with Ph$_3$P (0.20 g, 0.77 mmol) in THF (10 mL) and H$_2$O (1 mL). The mixture was stirred for 3 days. The solvent was removed in vacuo, and the residue was purified by silica gel chromatography (CH$_2$Cl$_2$/MeOH/28% NH$_3$·H$_2$O 12:6:1 then 10:5:1.5) to afford the desired product (0.077 g, 78% yield) as a glass. HCl in Et$_2$O (1 M, 0.5 mL) was added to the glass to give the corresponding HCl salt. $^1$H NMR (~10% CDCl$_3$ in CD$_3$OD, 500 MHz) δ4.81 (s, 10 H), 4.07–3.97 (m, 2 H), 3.82 (bs, 1 H), 3.71 (bs, 1 H), 3.65 (t, J=5.2 Hz, 2 H), 3.57 (bs, 1 H), 3.37–3.30 (m, 2 H), 3.22–3.02 (m, 8 H), 2.12–1.71 (series of multiplets, 17 H), 1.65–1.01 (series of multiplets, 13 H), 0.97 (d, J=6.8 Hz, 3 H), 0.94 (s, 3 H), 0.73 (s, 3 H); $^{13}$C NMR (~10% CDCl$_3$ in CD$_3$OD, 75 MHz) δ81.89, 80.58, 77.50, 70.04, 66.71, 66.56, 66.02, 47.11, 46.76, 44.20, 42.66, 40.50, 39.60, 39.40, 36.24, 36.11, 35.89, 35.67, 32.28, 29.38, 29.23, 29.10, 28.94, 28.49, 26.06, 24.21, 23.46, 23.30, 18.50, 12.86; HRFAB-MS (thioglycerol+Na$^+$ matrix) m/e: ([M+Na]$^+$) 668.4271 (100%), calcd. 668.4258.

Compound 133: The mesylate derived from 23 (0.19 g, 0.264 mmol) was stirred with excess octyl amine (2 mL) at 80° C. for 12 hr. After removal of octylamine in vacuo, the residue was chromatographed (silica gel, EtOAc/hexanes 1:4 with 2% Et$_3$N) to afford the desired product (0.19 g, 95% yield) as a pale yellow oil. $^1$H NMR (CDCl$_3$, 300 MHz) δ3.69–3.37 (series of multiplets, 11 H), 3.26–3.00 (m, 4 H), 2.61–2.53 (m, 4 H), 2.20–2.02 (m, 3 H), 1.98–0.99 (series of multiplets, 40 H), 0.92–0.85 (m, 9 H), 0.65 (s, 3H); $^{13}$C NMR (CDCl$_3$, 75 MHz) δ80.60, 79.74, 76.05, 64.97, 64.40, 64.28, 50.79, 50.25, 49.00, 48.90, 48.71, 46.47, 46.34, 42.65, 41.96, 39.80, 35.77, 35.41, 35.27, 35.05, 33.73, 31.96, 30.25, 29.76, 29.74, 29.67, 29.39, 29.05, 27.84, 27.61, 27.55, 26.70, 23.50, 23.00, 22.82, 22.79, 18.06, 14.23, 12.54; HRFAB-MS (thioglycerol+Na$^+$ matrix) m/e: ([M+H]$^+$) 755.6012 (100%), calcd. 755.6024. The triazide (0.18 g, 0.239 mmol) was dissolved in THF (10 mL) and EtOH (10 mL). Lindlar catalyst (44 mg) was added, and the suspension was shaken under H$_2$ (50 psi) for 12 hr. After removal of the solvent in vacuo, the residue was purified by silica gel chromatography (CH$_2$Cl$_2$/MeOH/28% NH$_3$.H$_2$O 10:5:1, then 10:5:1.5). To the product, 1 M HCl (2 mL) and the resulting clear solution was extracted with Et$_2$O (2×10 mL). 20% NAOH solution was added until the solution became strongly basic. CH$_2$Cl$_2$ (20 mL, 2×10 mL) was used to extract the basic solution. The combined extracts were dried over anhydrous Na$_2$SO$_4$, and removal of solvent in vacuo gave the desired product (0.114 g, 68% yield) as a clear oil. $^1$H NMR (~20% CDCl$_3$ in CD$_3$OD, 500 MHz) δ4.79 (bs, 7 H), 3.74–3.70 (m, 1 H), 3.66–3.61 (m, 1 H), 3.56–3.51 (m, 3 H), 3.31–3.29 (m, 2 H), 3.16–3.09 (m, 2 H), 2.88–2.72 (m, 6 H), 2.59–2.51 (m, 4 H), 2.18–2.07 (m, 3 H), 1.97–1.66 (series of multiplets, 14 H), 1.62–0.97 (series of multiplets, 25 H), 0.95 (d, J=6.3 Hz, 3 H), 0.93 (s, 3 H), 0.89 (t, J=6.8 Hz, 3 H), 0.70 (s, 3 H); $^{13}$C NMR (~20% CDCl$_3$ in CD$_3$OD, 75 MHz) δ81.82, 80.63, 77.23, 67.85, 67.19, 51.20, 50.69, 47.82, 47.24, 43.92, 43.01, 41.30, 40.80, 40.68, 40.22, 36.74, 36.38, 36.20, 35.87, 34.66, 34.15, 33.87, 32.90, 30.54, 30.39, 30.30, 29.64, 29.03, 28.59, 28.41, 26.96, 24.37, 23.65, 23.48, 18.75, 14.63, 13.09; HRFAB-MS (thioglycerol+Na$^+$ matrix) m/e: ([M+H]$^+$) 677.6309 (46.6%), calcd. 677.6309.

Compound 134: Compound 133 (0.08 g, 0.12 mmol) was dissolved in CHCl$_3$ (5 mL) and MeOH (5 mL), aminoiminosulfonic acid (0.045 g, 0.36 mmol) was added, and the suspension was stirred for 12 hr. The solvent was removed in vacuo, and the residue was dissolved in 1 M HCl (6 mL) and H$_2$O (10 mL). The solution was washed with Et$_2$O (3×5 mL), and 20% NaOH solution was then added dropwise until the solution became strongly basic. The basic mixture was extracted with CH$_2$Cl$_2$ (4×5 mL). The combined extracts were dried over anhydrous Na$_2$SO$_4$ and concentrated in vacuo to give the desired product (0.087 g, 91% yield) as a white glass. $^1$H NMR (~20% CDCl$_3$ in CD$_3$OD, 500 MHz) δ4.96 (bs, 13 H), 3.74–3.68 (m, 1 H), 3.65–3.50 (m, 4 H), 3.38–3.18 (series of multiplets, 10 H), 2.60–2.50 (m, 4 H), 2.15–1.99 (m, 3 H), 1.88–1.72 (m, 14 H), 1.60–0.99 (series of multiplets, 25 H), 0.94 (bs, 6 H), 0.89 (t, J=6.6 Hz, 3 H), 0.71 (s, 3 H); $^{13}$C NMR (~20% CDCl$_3$ in CD$_3$OD, 75 MHz) δ159.00, 158.87, 158.72, 81.68, 79.93, 76.95, 66.59, 65.93, 65.45, 50.82, 50.40, 47.64, 46.94, 43.67, 42.27, 40.18, 39.25, 36.19, 35.66, 35.40, 34.21, 32.45, 30.51, 30.26, 30.18, 30.10, 29.86, 29.35, 28.71, 28.15, 28.00, 26.87, 23.94, 23.44, 23.23, 23.12, 18.61, 14.42, 12.98; HRFAB-MS (thioglycerol+Na$^+$ matrix) m/e: ([M+H]$^+$) 803.6958 (18.4%), calcd. 803.6953.

Compound 135: The mesylate derived from 23 (0.092 g, 0.128 mmol) was dissolved in DMSO (2 mL) followed by the addition of NaN$_3$ (0.0167 g, 0.256 mmol). The suspension was heated to 70° C. for 12 hr. H$_2$O (20 mL) was added to the cooled suspension, and the mixture was extracted with EtOAc/hexanes (1:1) (20 mL, 3×10 mL). The combined extracts were washed with brine (30 mL), dried over anhydrous Na$_2$SO$_4$, and concentrated in vacuo to give the product (0.081 g, 95% yield) as a pale yellow oil. $^1$H NMR (CDCl$_3$, 300 MHz) δ3.69–3.36 (m, 11 H), 3.25–3.02 (m, 6 H), 2.20–2.02 (m, 3 H), 1.97–1.60 (m, 15 H), 1.55–0.98 (m, 13 H), 0.92 (d, J=6.3 Hz. 3 H), 0.89 (s, 3 H), 0.66 (s, 3 H); $^{13}$C NMR (CDCl$_3$, 75 MHz) δ⁻80.59, 79.77, 76.03, 65.01, 64.46, 64.30, 52.12, 48.99, 48.95, 48.76, 46.44, 46.42, 42.70, 41.99, 39.82, 35.56, 35.44, 35.31, 35.09, 33.09, 29.79, 29.77, 29.71, 29.08, 27.88, 27.78, 27.66, 25.65, 23.53, 23.03, 22.85, 18.00, 12.58; HRFAB-MS (thioglycerol+Na$^+$ matrix) m/e: ([M+Na]$^+$) 691.4512 (100%), calcd. 691.4496. The tetraazide (0.081 g, 0.12 mmol) was dissolved in THF (5 mL) and EtOH (10 mL). Lindlar catalyst (30 mg) was added, and the suspension was shaken under H$_2$ (50 psi) for 12 hr. After removal of the solvent in vacuo, the residue was purified by silica gel chromatography (CH$_2$Cl$_2$/MeOH/28% NH$_3$.H$_2$O 5:3:1, then 2:2:1). To the product, 1 M HCl (2 mL) was added, and the resulting solution was washed with Et$_2$O (2×10 mL). 20% NaOH solution was added to the aqueous phase until the solution became strongly basic. CH$_2$Cl$_2$ (10 mL, 2×5 mL) was used to extract the basic solution. The combined extracts were dried over anhydrous Na$_2$SO$_4$, and concentration in vacuo gave the desired product (0.044 g, 64% yield) as a colorless oil. $^1$H NMR (~20% CDCl$_3$ in CD$_3$OD, 500 MHz) δ4.79 (bs, 8 H), 3.74–3.70 (m, 1 H), 3.66–3.62 (m, 1 H), 3.56–3.52 (m, 3 H), 3.31–3.27 (m, 2 H), 3.16–3.10 (m, 2 H), 2.82–2.70 (m, 6 H), 2.64–2.54 (m, 2 H), 2.19–2.07 (m, 3 H), 1.99–1.66 (series of multiplets, 14 H), 1.58–0.96 (series of multiplets, 13 H), 0.96 (d, J=6.6 Hz, 3 H), 0.93 (s, 3 H), 0.70 (s, 3 H); $^{13}$C NMR (~20% CDCl$_3$ in CD$_3$OD, 75 MHz) δ81.96, 90.76, 77.33, 67.92, 67.26, 47.84, 47.33, 44.04, 43.24, 43.15, 41.40, 40.91, 40.78, 40.29, 36.82, 36.48, 36.28, 35.96, 34.39, 34.11, 30.59, 29.69, 29.13, 28.68, 28.64, 24.43, 23.69, 23.48, 18.77, 13.06; HRFAB-MS (thioglycerol+Na$^+$ matrix) m/e: ([M+H]$^+$) 565.5041 (100%), calcd. 565.5057.

Example 12

Syntheses of Compounds 203a–b, 207a–c, 208a–c, 209a–c and 210a–b

Compounds 203a–b, 207a–c, 208a–c, 209a–c, and 210a–b: BOC-glycine was reacted with DCC, DMAP and cholic acid derivative 201 (Scheme 11) to give triester 202a in good yield. A similar reaction incorporating BOC-β-alanine was also successful, giving 202b. Deprotection of 202a and 202b with HCl in dioxane, followed by purification (SiO$_2$ chromatography with a CH$_2$Cl$_2$MeOH/NH$_4$OH eluent), gave triesters 203a and 203b in good yield.

Triamides of glycine and β-alanine (207a and 207b, respectively) were formed using the same reaction conditions (Scheme 12). Triamides with α-branched amino acids could also be formed. For example, under the conditions described, a triamide with bis-BOC-lysine side chains was formed (compound 207c). The C24 esters of 207a–c were hydrolyzed with LiOH in THF and methanol to give alcohols 208a–c. Deprotection using HCl in dioxane (208a–c) gave triamides 209a–c in good yield. In addition, alcohols 208a and 208b were mesylated and reacted with benzylmethyl amine. Deprotection of the resulting compounds with HCl in dioxane gave triamides 210a and 210b (Scheme 12). The antibacterial properties of these compounds are summarized in Table 14.

Example 13

Synthesis of Compounds 302, 312–321, 324–326, 328–331 and 341–343

Compound 302: Compound 308 (5β-cholanic acid 3,7, 12-trione methyl ester) was prepared from methyl cholate and pyridinium dichromate in near quantitative yield from methyl cholate. Compound 308 can also be prepared as described in Pearson et al., *J. Chem. Soc. Perkins Trans. 1* 1985, 267; Mitra et al., *J. Org. Chem.* 1968, 33, 175; and Takeda et al., *J. Biochem. (Tokyo)* 1959, 46, 1313. Compound 308 was treated with hydroxyl amine hydrochloride and sodium acetate in refluxing ethanol for 12 hr (as described in Hsieh et al., *Bioorg. Med. Chem.* 1995, 3, 823), giving 309 in 97% yield.

A 250 ml three neck flask was charged with glyme (100 ml); to this was added 309 (1.00 g, 2.16 mmol) and sodium borohydride (2.11 g, 55.7 mmol). TiCl$_4$ (4.0 mL, 36.4 mmol) was added to the mixture slowly under nitrogen at 0° C. The resulting green mixture was stirred at room temperature for 24 hours and then refluxed for another 12 h. The flask was cooled in an ice bath, and ammonium hydroxide (100 mL) was added. The resulting mixture was stirred for 6 hours at room temperature. Conc. HCl (60 mL) was added slowly, and the acidic mixture was stirred for 8 hours. The resulting suspension was made alkaline by adding solid KOH. The suspension was filtered and the solids were washed with MeOH. The combined filtrate and washings were combined and concentrated in vacuo. The resulting solid was suspended in 6% aqueous KOH (100 mL) and extracted with CH$_2$Cl$_2$ (4×75 mL). The combined extracts were dried over Na$_2$SO$_4$, and solvent was removed in vacuo to give 1.14 g of a white solid. The mixture was chromatographed on silica gel (CH$_2$Cl$_2$/MeOH/NH$_4$OH 12:6:1) giving 302 (0.282 g, 33% yield), 3 (0.066 g, 8% yield), 4 (0.118 g, 14% yield).

Compound 302: m.p. 200–202° C.; $^1$H NMR (~10% CDCl$_3$ in CD$_3$OD, 300 MHz) δ4.81 (bs, 7 H), 3.57–3.49 (m, 2 H), 3.14 (t, J=3.2 Hz, 1 H), 2.97 (bs, 1 H), 2.55–2.50 (m, 1 H), 2.15–2.10 (m, 1 H), 1.95–1.83 (m, 3 H), 1.74–0.99 (series of multiplets, 20 H), 1.01 (d, J=6.4 Hz, 3 H), 0.95 (s, 3 H), 0.79 (s, 3 H); $^{13}$CNMR (~10% CDCl$_3$ in CD$_3$OD, 75 MHz) 63.28, 55.01, 52.39, 49.20, 48.69, 47.00, 43.24, 42.77, 41.03, 40.27, 36.82, 36.35, 35.75, 35.12, 32.77, 31.36, 30.10, 28.54, 27.88, 26.96, 24.35, 23.38, 18.18, 14.23, HRFAB-MS (thioglycerol+Na$^+$ matrix) m/e; ([M+H]$^+$) 392.3627 (100%); calcd. 392.3641.

Octanyl cholate (328): Cholic acid (3.14 g, 7.43 mmol) and 10-camphorsulfonic acid (0.52 g, 2.23 mmol) were dissolved in octanol (3.5 mL, 23.44 mmol). The solution was warmed to 40–50° C. in oil bath under vacuum (~13 mm/Hg). After 14 h, the remaining octanol was evaporated under high vacuum. The crude product was purified via chromatography (silica gel, 5% MeOH in CH$_2$Cl$_2$) to afford the desired product (2.81 g, 73% yield) as a white powder. $^1$H NMR (CDCl$_3$, 500 MHz) δ4.06 (t, J=6.7 Hz, 2 H), 3.98 (s, 1 H), 3.86 (s, 1 H), 3.48–3.44 (m, 1 H), 2.41–2.34 (m, 1 H), 2.28–2.18 (m, 3 H), 1.98–1.28 (series of multiplets, 35 H), 0.99 (d, J=3.3 Hz, 3 H), 0.90 (s, 3 H), 0.89 (t, J=7 Hz, 3 H), 0.69 (s, 3 H); $^{13}$C NMR (CDCl$_3$, 75 MHz) δ154.38, 73.18, 72.14, 68.63, 56.07, 50.02, 49.32, 47.07, 46.74, 41.96, 41.67, 39.84, 39.76, 35.66, 35.45, 34.95, 34.86, 34.15, 32.97, 32.91, 31.65, 31.11, 30.68, 28.39, 27.78, 26.66, 26.52, 25.82, 25.70, 25.54, 25.15, 24.95, 23.45, 22.69, 17.77, 12.71; HRFAB-MS (thioglycerol+Na$^+$ matrix) m/e: ([M+Na]$^+$) 543.4015 (100%), calcd. 543.4026.

Representative synthesis of compounds 329–331: Octanyl cholate (328) (0.266 g, 0.511 mmol), N-t-Boc-glycine (0.403 g, 2.298 mmol), DCC (0.474 g, 2.298 mmol) and DMAP (0.0624 g, 0.051 mmol) were mixed in CH$_2$Cl$_2$ (15 mL) for 3 h. The resulting white precipitate was removed by filtration. The filtrate was concentrated, and the product was purified by chromatography (silica gel, EtOAc/Hexane 1:2) to afford the desired product (0.481 g, 95% yield) as a white powder. Compound 329 $^1$H NMR (CDCl$_3$, 300 MHz) δ5.18 (br, 3 H), 5.01 (s, 1 H), 4.61 (m, 1 H), 4.04 (t, J=6.5 Hz, 2 H), 3.97–3.88 (series of multiplets, 6 H), 2.39–2.15 (series of multiplets, 2 H), 2.06–1.02 (series of multiplets, 35 H), 1.46 (s, 18 H), 1.45 (s, 9 H), 0.93 (s, 3 H), 0.88 (t, J=6.7 Hz, 3 H), 0.81 (d, J=6 Hz, 3 H), 0.74 (s, 3 H); $^{13}$C NMR (CDCl$_3$, 75 MHz) δ174.26, 170.19, 169.9, 169.78, 155.87, 155.67, 79.95, 76.47, 75.167, 72.11, 64.55, 47.40, 45.28, 43.17, 42.86, 40.82, 37.94, 34.71, 34.63, 34.43, 31.86, 31.340, 31.20, 30.76, 29.29, 29.25, 28.80, 28.72, 28.42, 28.06, 27.96, 27.19, 26.81, 26.29, 26.012, 25.66, 22.87, 22.71, 22.57, 17.55, 14.18, 12.27; HRFAB-MS (thioglycerol+Na$^+$ matrix) m/e: ([M+Na]$^+$) 1014.6261 (100%), calcd. 1014.6242. Compound 330: $^1$H NMR (CDCl$_3$, 500 MHz) δ5.10 (s, 1 H), 4.92 (d, J=2.44 Hz, 1 H), 4.55 (m, 1 H), 4.00 (t, J=6.8 Hz, 2 H), 3.39–3.33 (series of multiplets, 6 H), 2.595–2.467 (series of multiplets, 6 H), 2.31–2.12 (series of multiplets, 2 H), 2.01–1.00 (series of multiplets, 37 H), 1.39 (s, 27 H), 0.88 (s, 3 H), 0.84 (t, J=6.8 Hz, 3 H), 0.76 (d, J=6.3 Hz, 3 H), 0.69 (s, 3 H); $^{13}$C NMR (CDCl$_3$, 75 MHz) δ174.16, 172.10, 171.78, 171.67, 155.95, 79.45, 75.67, 74.21, 71.10, 64.63, 47.79, 45.27, 43.52, 40.97, 37.92, 36.35, 35.14, 35.05, 34.90, 34.71, 34.46, 31.91, 31.45, 30.95, 29.35, 29.31, 28.96, 28.78, 28.56, 28.55, 27.22, 26.98, 26.269, 25.71, 23.00, 22.77, 22.64, 17.75, 14.24, 12.39; HRFAB-MS (thioglycerol+Na$^+$ matrix) m/e: ([M+Na]$^+$) 1056.6702 (100%), calcd. 1056.6712. Compound 331 $^{13}$C NMR (CDCl$_3$, 125 MHz) δ174.00, 172.75, 172.41, 172.30, 156.03, 79.00, 75.28, 73.79, 70.77, 64.39, 47.43, 45.04, 43.21, 40.76, 40.00, 39.93, 37.78, 34.74, 34.62, 34.23, 32.19, 32.01, 31.70, 31.24, 30.77, 29.13, 29.10, 28.67, 38.58, 28.38, 25.86, 25.37, 22.56, 22.38, 17.51, 14.05, 12.13; HRFAB-MS (thioglycerol+Na$^+$ matrix) m/e: ([M+Na]$^+$) 1098.7181 (100%), calcd. 1098.7181.

Representative synthesis of compounds 341–343: To compound 329 (0.463 g, 0.467 mmol) was added HCl in dioxane (0.3 mL, 4.0 M). After stirring the mixture for 30 min, the excess HCl and solvent were removed in vacuo. The product was isolated, after chromatography (silica gel, CH$_2$Cl$_2$/MeOH/NH$_3$.H$_2$O 10:1.2:0.1) as a (0.271 g, 84%) pale oil. The trihydrochloride salt of 341 was prepared by addition of HCl in dioxane and evaporation of excess HCl and dioxane in vacuo giving a white powder. Compound 341: $^1$H NMR (CDCl$_3$ with ~10% CD$_3$OD, 500 MHz) δ5.16 (s, 1 H), 4.99 (t, J=3.6 Hz, 1 H), 4.61 (m, 1 H), 4.04 (t, J=6.8 Hz, 2 H), 3.51–3.36 (m, 6 H), 2.34–2.15 (m, 2 H), 2.00–1.05 (series of multiplets, 40 H), 0.93 (s, 3 H), 0.88 (t, J=7.1 Hz, 3 H), 0.80 (d, J=3.2 Hz, 3 H), 0.74 (s, 3 H); $^{13}$C NMR (CDCl$_3$ and ~10% CD$_3$OD, 75 MHz) δ174.32, 173.92, 173.81, 76.08, 74.67, 71.61, 64.73, 47.64, 45.39, 44.41, 43.49, 40.97, 37.99, 34.99, 34.77, 34.71, 34.52, 31.96, 31.54, 31.35, 30.96, 29.39, 29.36, 29.02, 28.82, 27.32, 27.11, 26.11, 25.83, 23.01, 22.82, 22.69, 17.79, 14.28, 12.41; HRFAB-MS (thioglycerol+Na$^+$ matrix) m/e: ([M+Na]$^+$) 714.4651 (100%), calcd. 714.4669. Compound 342: $^1$H NMR (CDCl$_3$ and ~10% CD$_3$OD, 300 MHz) δ5.142 (s, 1 H), 4.96 (d, J=2.7 Hz, 1 H), 4.60, (m, 1 H), 4.04 (t, J=6.6 Hz, 2 H), 3.07–2.95 (series of multiplets, 6 H), 2.56–2.43 (series of multiplets, 6 H), 2.38–2.13 (series of multiplets, 2 H), 2.07–1.02 (series of multiplets, 36 H), 0.92 (s, 3 H), 0.88 (t, J=6.6 Hz, 3 H), 0.82 (d, J=6.6 Hz, 3 H), 0.73 (s, 3 H); $^{13}$C NMR (CDCl$_3$ and CD$_3$OD, 75 MHz) δ174.29, 172.29, 171.98, 171.92, 75.52, 74.09, 70.98, 64.67, 47.78, 45.26, 43.52, 40.98, 38.73, 38.62, 38.35, 38.07, 38.03, 37.99, 35.01, 34.81, 34.77, 34.49, 31.92, 31.50, 31.40, 30.99, 29.36, 29.33, 28.93, 28.80, 27.43, 26.96, 26.08, 25.56, 23.07, 22.79, 22.62, 17.73, 14.25, 12.34; HRFAB-MS (thioglycerol+Na$^+$ matrix) m/e: ([M+Na]$^+$) 714.4651 (100%), calcd. 714.4669. Compound 343: $^1$H NMR (CDCl$_3$ and CD$_3$OD, 500 MHz) δ5.12 (s, 1 H) 4.93 (s, 1 H), 4.59 (m, 1 H), 4.04 (t, J=7 Hz, 2 H), 2.79–2.69 (series of multiplets, 6 H), 2.4621–2.2999 (series of multiplets, 6 H), 2.2033–1.0854 (series of multiplets, 42 H), 0.94 (s, 2 H), 0.91 (s, 1 H), 0.88 (t, J=7 Hz, 3 H), 0.82 (d, J=6.4 Hz, 3 H), 0.75 (s, 3 H); $^{13}$C NMR (CDCl$_3$ and CD$_3$OD, 75 MHz) δ174.70, 171.97, 171.86, 171.75, 76.10, 74.55, 71.56, 64.85, 47.96, 45.31, 43.37, 40.87, 38.09, 34.86, 34.80, 34.73, 34.46, 32.84, 32.62, 32.27, 31.87, 31.75, 31.42, 31.08, 29.31, 29.28, 29.26, 28.78, 28.73, 27.38, 26.91, 26.05, 25.37, 23.24, 23.15, 22.95, 22.74, 22.71, 22.43, 17.78, 14.11, 12.28; HRFAB-MS (thioglycerol+Na$^+$ matrix) m/e: ([M+Na]$^+$) 798.5624 (100%), calcd. 798.5609.

Benzyl cholate (312): Cholic acid (4.33 g, 10.62 mmol) and 10-caphorsulfonic acid (0.493 g, 2.21 mmol) were dissolved in benzyl alcohol (1.97 mL, 19.3 mmol). The suspension was heated to 50° C. in oil bath and stirred under vacuum (~13 mm/Hg) for 16 h. Excess benzyl alcohol was removed in vacuo, and the crude product was chromatographed (silica gel, 5% MeOH in CH$_2$Cl$_2$) to give the desire product as a white powder (4.23 g, 81% yield). $^1$H NMR (CDCl$_3$, 500 MHz) δ7.34–7.33 (m, 5 H), 5.10 (d, J=1.5 Hz, 2 H), 3.92 (s, 1 H), 3.81 (s, 1 H), 3.42 (s, 1 H), 3.40 (br, m, 3 H), 2.44–2.38 (m, 1 H), 2.31–2.25 (m, 1 H), 2.219 (t, J=12 Hz, 2 H), 0.96 (d, J=5.5 Hz, 3 H), 0.86 (s, 3 H), 0.63 (s, 3 H); $^{13}$C NMR (CDCl$_3$, 125 MHz) δ174.25, 136.30, 128.66, 128.63, 128.32, 128.28, 128.24, 73.18, 71.98, 68.54, 66.18, 47.14, 46.56, 41.69, 39.65, 35.51, 35.37, 34.91, 34.84, 31.49, 31.08, 30.50, 28.31, 27.62, 26.47, 23.35, 22.65, 22.60, 17.42, 12.63, 12.57; HRFAB-MS (thioglycerol+Na$^+$ matrix) m/e: ([M+Na]$^+$) 521.3235 (100%), calcd. 521.3242.

Representative synthesis of compounds 313–315: Benzyl cholate (312) (0.248 g, 0.499 mmol), N-t-Boc-glycine (0.404 g, 2.30 mmol), DCC (0.338 g, 1.49 mmol) and DMAP (0.051 g, 0.399 mmol) were added to CH$_2$Cl$_2$ (15 mL), and the suspension was stirred for 16 h. The resulting white precipitate was removed by filtration, and the filtrate was concentrated. The product was obtained after chromatorgraphy (silica gel, EtOAc/Hexane 0.6:1) as a white powder (0.329 g, 68%). Compound 313: $^1$H NMR (CDCl$_3$, 300 MHz) δ7.34–7.33 (m, 5 H), 5.16 (s, 1 H), 5.08 (dd, J=22.5 Hz, 12.3 Hz, 4 H), 5.00 (s, 1 H), 4.60 (m, 1 H), 4.04–3.81 (series of multiplets, 6 H), 2.43–1.01 (series of multiplets, 25 H), 1.46 (s, 9 H), 1.44 (s, 18 H), 0.92 (s, 3 H), 0.797 (d, J=5.7 Hz, 3 H), 0.69 (s, 1 H); $^{13}$C NMR (CDCl$_3$, 75 MHz) δ173.99, 170.25, 170.05, 169.85, 155.73, 136.19, 128.69, 128.45, 128.35, 80.06, 77.65, 77.23, 76.80, 76.53, 75.24, 72.19, 66.29, 47.46, 45.35, 43.24, 42.91, 40.89, 38.00, 34.79, 34.66, 34.49, 31.43, 31.25, 30.77, 28.88, 28.40, 27.23, 26.89, 25.74, 22.94, 22.65, 17.61, 12.32; FAB-MS (thioglycerol+Na$^+$ matrix) m/e: ([M+Na]$^+$) 992.5468 (100%), calcd. 992.5460.

Representative synthesis of compounds 316–318: Compound 313 (0.505 g, 0.520 mmol) and Pd (5 wt. % on active carbon, 0.111 g, 0.0521 mmol) were added to MeOH (5 mL). The suspension was stirred under H$_2$ (50 psi) for 20 hours. The solids were removed by filtration and the filtrate was concentrated. Purification of the product via chromatography (silica gel, 5% MeOH in CH$_2$Cl$_2$) gave a white powder (0.450 g, 98% yield). Compound 316: $^1$H NMR (CDCl$_3$, 500 MHz) δ5.20 (s, 1 H), 5.12 (br., 2 H), 4.92 (s, 1 H), 4.55 (m, 1 H), 3.98–3.83 (series of multiplets, 6 H), 2.30–2.13 (series of multiplets, 2 H), 1.96–0.98 (series of multiplets, 30 H), 1.40 (s, 9 H), 1.39 (s, 18 H), 0.87 (s, 3 H), 0.76 (d, J=6.3 Hz, 3 H), 0.68 (s, 3 H); $^{13}$C NMR (CDCl$_3$ 75 MHz) δ174.11, 165.60, 165.41, 165.22, 151.28, 151.14, 75.48, 75.26, 71.81, 70.57, 67.50, 45.95, 42.58, 40.65, 38.52, 38.16, 36.17, 33.28, 30.01, 29.78, 26.71, 26.42, 25.95, 24.16, 23.78, 23.40, 23.31, 22.55, 22.16, 21.03, 18.23, 17.93, 12.91, 7.61; FAB-MS (thioglycerol+Na$^+$ matrix) m/e: ([M+Na]$^+$) 902.4997 (21%), calcd. 902.4990.

Representative synthesis of compounds 319–321: Compound 316 (0.375 g, 0.427 mmol), DCC (0.105 g, 0.512 mmol) and DMAP (0.062 g, 0.512 mmol) and N,N-dimethylethanolamine (0.09 ml, 0.896 mmol) were added to CH$_2$Cl$_2$ (15 mL). The mixture for 16 h, and solvent and excess N,N-dimethylethanolamine were removed in vacuo. The product was purified via chromatography (silica gel EtOAc/hexane/Et$_3$N, 12:10:0.6) giving a white powder (0.330 g, 82% yield). $^1$H NMR (CDCl$_3$ and ~10% CD$_3$OD, 500 MHz) δ5.18 (s, 1 H), 5.00 (s, 1 H), 4.19 (t, J=5.0 Hz, 2 H), 3.92 (s, 3 H), 3.81 (s, 3 H), 2.62 (t, J=10 Hz, 2 H), 2.30 (s, 6 H), 1.47 (s, 9 H), 1.47 (s, 1 H), 1.45 (s, 1 H), 2.12–1.05 (series of multiplets, 27 H), 0.96 (s, 3 H), 0.84 (d, J=10.5 Hz, 3 H), 0.78 (s, 3 H); $^{13}$C NMR (CDCl$_3$ and ~10% CD$_3$OD, 125 MHz) δ174.19, 170.05, 169.87, 156.21, 79.36, 79.27, 76.06, 76.90, 71.80, 61.19, 57.04, 46.88, 44.87, 44.67, 44.53, 42.78, 42.15, 42.01, 40.43, 37.47, 34.32, 34.11, 33.92, 33.35, 33.25, 30.74, 30.56, 30.16, 28.40, 27.67, 27.62, 26.73, 26.19, 25.18, 25.10, 24.72, 24.49, 22.29, 21.81, 16.76, 11.56; FAB-MS (thioglycerol+Na$^+$ matrix) m/e: ([M+Na]$^+$) 973.5723 (100%), calcd. 973.5725. The white solid from the previous reaction (0.680 g, 0.714 mmol) and MeI (1 M in CH$_2$Cl$_2$, 1.5 mL) were stirred together for 2 h. The solvent and excess MeI were removed in vacuo giving a white solid (0.812 g ~100%). The product was carried on without further purification.

Representative synthesis of compounds 324–326: Compound 319 (0.812 g, 0.714 mmol) was dissolved in CH$_2$Cl$_2$ (5 mL) and trifluoroacetic acid (0.5 mL) was added. The mixture was stirred for 16 min. The solvent and excess acid were removed in vacuo, and the resulting oil was chromatographed (silica gel, CH$_2$Cl$_2$/MeOH/NH$_3$.H$_2$O 4:4:1) to give the desired product as a pale glass (0.437 g, 90% yield). Addition of HCl (2 M in ethyl ether, 2.5 mL) gave the trihydrochloride salt of 324 as a pale yellow powder. Compound 324: $^1$H NMR (50% CDCl$_3$, 50% CD$_3$OD, 300 MHz) δ5.43 (s, 1 H), 5.24 (s, 1 H), 4.84 (m, 1 H), 4.66 (m, 2 H), 4.16–3.96 (series of multiplets, 6 H), 3.88 (m, 2 H), 3.37 (s, 9 H), 0.67 (s, 3 H), 0.59 (d, J=6.3 Hz, 3 H), 0.56 (s, 3 H); $^{13}$C NMR (50% CDCl$_3$, 50% CD$_3$OD, 75 MHz) δ173.47, 167.06, 167.01, 166.70, 78.01, 76.49, 73.78, 64.98, 57.67, 53.36, 47.49, 46.99, 45.61, 43.28, 40.83, 40.23, 40.10, 37.69, 34.80, 34.48, 34.28, 31.03, 30.63, 30.44, 28.94, 27.05, 26.56, 25.50, 22.53, 21.56, 16.95, 11.37; FAB-MS (thioglycerol+Na$^+$ matrix) m/e: ([M–I]$^+$) 665.4475 (85.6%), calcd 665.4489. Compounds 325 and 326 proved too unstable to chromatograph using the basic eluent used for the purification of 324. Consequently, 325 and 326 were prepared by deprotection of 320 and 321 using HCl (2 M in diethyl ether), followed by tituration with ethyl acetate. The compounds were then used without further purification. $^1$H NMR spectroscopy indicated that compounds 325 and 326 were >95% pure. Compound 325: $^1$H NMR (50% CDCl$_3$, 50% CD$_3$OD, 500 MHz) δ5.21 (s, 1 H), 5.02 (d, J=4 Hz, 1 H), 4.64 (m, 1 H), 4.53 (m, 2 H), 3.74 (m, 2 H), 3.31–3.01 (series of multiplets, 6 H), 3.23 (s, 9 H), 2.96–2.73 (series of multiples, 6 H), 2.51–2.44 (m, 1 H), 2.35–2.29 (m, 1 H), 2.14–1.09 (series of multiplets, 26 H), 0.99 (s, 3 H), 0.85 (d, J=6.5 Hz, 3 H), 0.80 (s, 3 H); $^{13}$C NMR (50% CDCl$_3$, 50% CD$_3$OD, 125 MHz) δ172.77, 169.88, 169.56, 169.50, 75.94, 74.44, 71.57, 64.31, 56.94, 52.92, 46.78, 44.59, 42.70, 40.21, 37.16, 34.80, 34.72, 34.66, 34.05, 34.00, 33.78, 33.62, 30.95, 30.91, 30.81, 30.41, 29.96, 29.81, 28.20, 26.37, 26.06, 24.74, 24.24, 22.04, 21.13, 16.54, 10.97; FAB-MS (thioglycerol+Na$^+$ matrix) m/e: ([M–I]$^+$) 707.4958 (25.6%), cacld 707.4958. Compound 326: $^1$H NMR (50% CDCl$_3$, 50% CD$_3$OD, 500 MHz) δ5.12 (s, 1H), 4.94 (d, J=2.5 Hz, 1 H), 4.56 (m. 1 H), 4.51 (t, J=2.3 Hz, 2 H), 3.74 (m, 2 H), 3.23 (s, 9 H), 3.05–3.01 (m, 4 H), 2.98 (t, J=7.5 Hz, 2 H), 2.63–2.43 (series of multiplets, 6 H), 2.31–2.24 (series of multiplets, 2 H), 2.07–1.87 (series of multiplets, 12 H), 1.17–1.05 (series of multiplets, 23 H), 0.94 (s, 3 H), 0.82 (d, J=6.0 Hz, 3 H), 0.76 (s, 3 H); $^{13}$C NMR (50% CDCl$_3$, 50% CD$_3$OD, 125 MHz) δ171.87, 169.79, 169.59, 169.50, 76.12, 74.70, 71.65, 65.57, 65.08, 64.40, 57.68, 53.74, 52.78, 45.33, 43.54, 41.04, 39.12, 37.92, 43.85, 34.72, 34.56, 34.34, 32.30, 31.47, 31.27, 30.87, 30.58, 29.03, 27.053, 26.84, 25.51, 24.95, 24.91, 22.87, 22.82, 22.65, 21.93, 17.31, 11.81; FAB-MS (thioglycerol+Na$^+$ matrix) m/e: ([M–I]$^+$) 749.5432 (100%), cacld 749.5436.

Example 14
Stability Tests of Compounds 352–354

Figure 9:
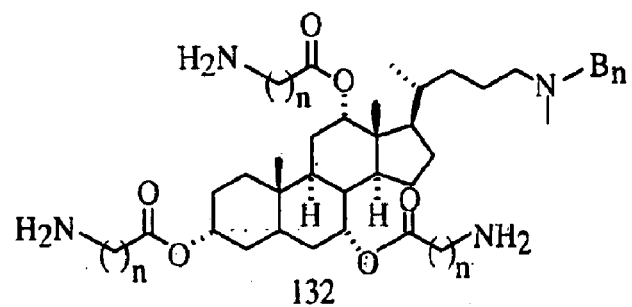
FIG. 9 is a drawing showing compounds 352–354.
Figure 10:
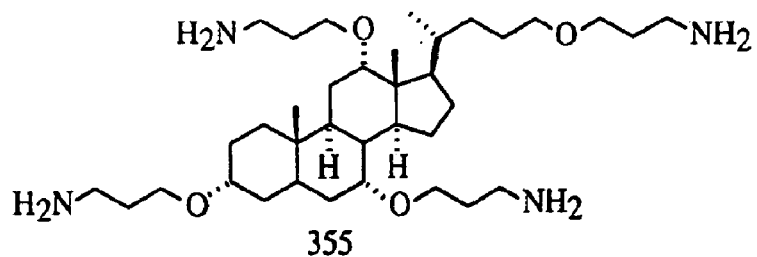
FIG. 10 is a drawing showing compound 355.

Compounds 352–354 were dissolved in 50 mM phosphate buffered water (pH 2.0, 7.0 or 12.0) at approximately 10 mM concentrations. The structures of compounds 352–354 are given in FIG. 9. Decomposition of the compounds was observed via HPLC (cyano-silica column, 0.15% TFA water-acetonitrile gradient elution). Table 15 shows the stabilities (half-lives) of compounds 352–354 in phosphate buffer at room temperature, pH 2.0, pH 7.0 and pH 12.0. These compounds were used since they contain a chromophore that facilitated monitoring of decomposition by absorption methods common in the HPLC apparatus used.

At low pH, the amines are expected to be protonated and the compounds showed relative stability. At higher pH, the amines were less strongly protonated and became involved in ester hydrolysis. The γ-aminobutyric acid-derived compound was especially susceptible to hydrolysis, presumably yielding pyrrolidone. In general, the compounds are believed to hydrolyse to give cholic acid, choline or octanol, and glycine, beta-alanine, or pyrrolidone, depending on the particular compound.

Decomposition through ester hydrolysis yielded compounds that were less polar and easily separable from the starting compounds. Initially, only one benezene-containing decomposition product was observed; at longer reaction times, two other decomposition products were observed which presumably corresponded to sequential ester hydrolysis.

Example 15
Further Syntheses of Compounds of Formula I

Compounds of formula I can also be prepared as shown in the following scheme.

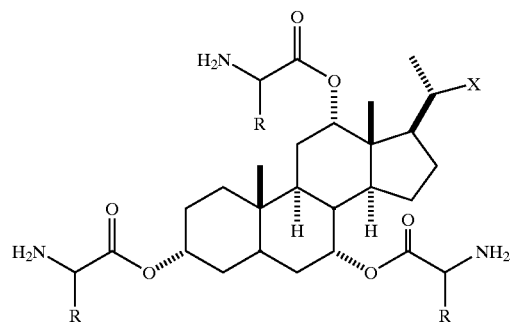

The R groups correspond to the side chain of any combination of amino acids (D or L)

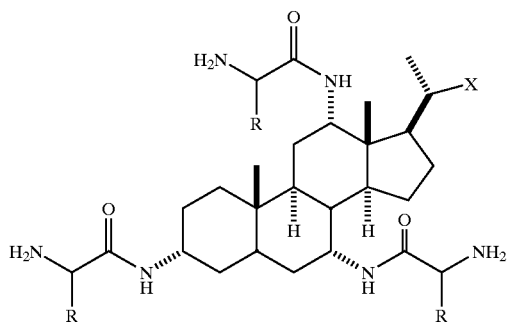

The R groups correspond to the side chain of any combination of amino acids (D or L)

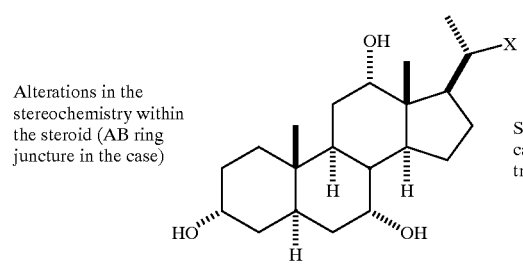

Alterations in the stereochemistry within the steroid (AB ring juncture in the case)

Schemes described above can be used for this transformation.

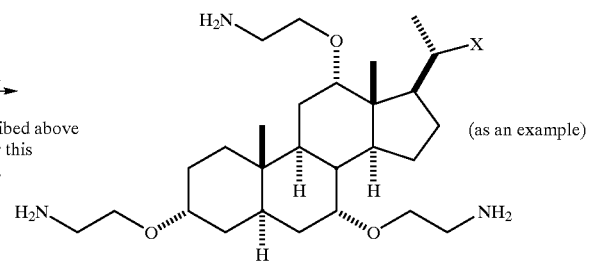

(as an example)

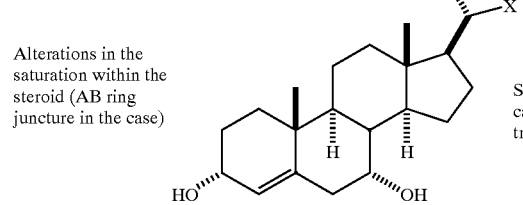

Alterations in the saturation within the steroid (AB ring juncture in the case)

Schemes described above can be used for this transformation.

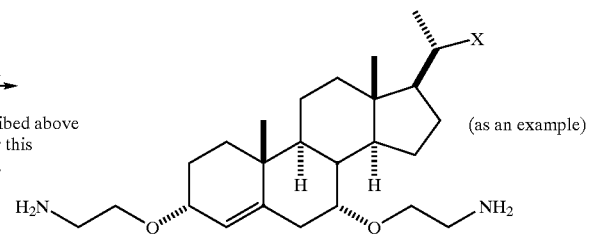

(as an example)

-continued

Alterations in the number of hydroxyl groups on the steroid (OH-12 in this case)

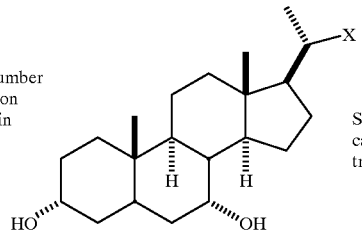

Schemes described above can be used for this transformation.

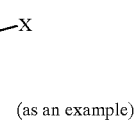

(as an example)

Alterations in the other groups on the steroid (in the A ring this case)

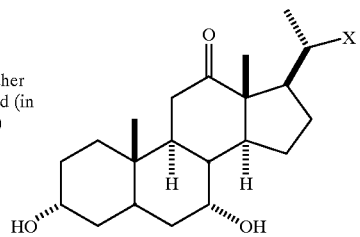

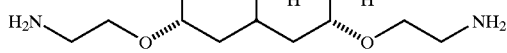

(as an example)

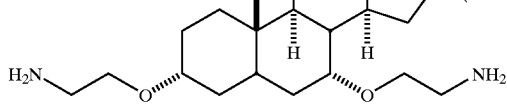

ethylene glycol, acid, benzene, reflux

MeOH, acid (or suitable protecting group)

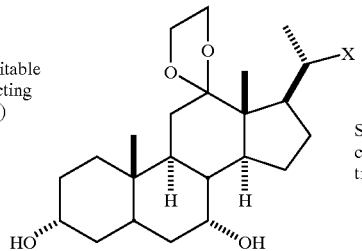

Schemes described above can be used for this transformation.

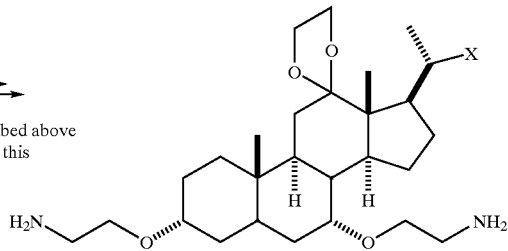

Descriptions of the steroid starting materials shown above can be found in Dictionary of Steroids, Hill, R. A.; Kirk, D. N.; Makin, H. L. J.; Murphy, G. M.; eds., Chapman and Hall: New York, 1991.

Example 15
Testing of Compounds with Gram-Negative Bacteria MIC and MBC Measurements General: Microorganisms. Reference strains were purchased from the American Type Culture Collection (Rockville, Md.) or Bactrol disks from Difeo Laboratories (Detroit, Mich.). The following specific ATCC strains were used: 10798 *Escherichia coli,* 25922 *Escherichia coli,* 13883 *Klebsiella pneumoniae,* 27853 *Pseudomonas aeruginosa,* 14028 *Salmonella typhimurium,* 29212 *Enterococcus faecalis,* 25923 *Staphylococcus aureus,* 19615 *Streptococcus pyogenes,* and 90028 *Candida albicans.* Bacterial strains were maintained on Mueller-Hinton agar plates, and *Candida albicans* was maintained on Sabouraud Dextrose agar plates.

Tryptic soy broth (TSB) was made by dissolving 27.5 grams of tryptic soy broth without dextrose (DIFCO Laboratories) in 1 liter of deionized water and sterilizing at 121° C. for 15 minutes. Solid agar (TSA) plates were made by dissolving 6.4 grams of tryptic soy broth and 12 grams of agar (purified grade, Fischer Scientific) in 800 mL of deionized water and sterilizing at 121° C. for 20 minutes. Aliquots (20 mL) of the homogeneous solution were then poured in sterile plastic petri dishes (100×15 mm, Fisher Scientific). Solutions of compounds were made by dissolving the HCl salt of the respective compound into an appropriate amount of deionized and sterilized water followed by microfiltration.

Representative procedure for measuring MIC and MBC values: A suspension was prepared of *E. coli* (ATCC 10798) containing ~10 CFU (colony forming units)/mL from a culture incubated in TSB at 37° C. for 24 hours. Aliquots of 1 mL of the suspension were added to test tubes containing 1 mL TSB and incrementally varied concentrations of cholic acid derivatives and/or erythromycin or novobiocin. In the sensitization experiments, erythromycin or novobiocin were added 15 minutes later than the cholic acid derivatives. The samples were subjected to stationary incubation at 37° C. for 24 hours. Sample turbidity was determined by measuring absorption at 760 nm (HP 8453 UV-Visible Chemstation, Hewlett Packard). Additionally, an alliquot from each of the samples showing no measurable turbidity was subcultured on TSA plates (alliquots were diluted to provide fewer than 300 CFU). Colonies that grew on the subculture after overnight incubation were counted and the number of CFU/mL in the samples were calculated. The calculated values were compared to the number of CFU/mL in the original inoculum. MIC values were determined as the concentrations of the studied compounds at which the number of CFU/mL remained constant or decreased after incubation for 24 hours. The MBC values were determined as the lowest concentrations of the studied compounds that allowed less than 0.1% of the original bacterial suspension to survive.

Example 16
Demonstration of Membrane Disrupting Properties of the Cholic Acid Derivatives Using a technique described by J. M. Shupp, S. E. Travis, L. B. Price, R. F. Shand, P. Keim, RAPID BACTERIAL PERMEABILIZATION REAGENT USEFUL FOR ENZYME ASSAYS, Biotechniques, 1995, vol. 19, 18–20, we have shown that the cholic acid derivatives increase the permeability of the outer membrane of Gram-negative bacteria. The values for half maximum luminescence (indicating permeabilization of the outer membrane allowing luciferin to enter the cell) for 2 is 7 µg/mL and for 10 is 33 µg/mL. These values correspond to the measured MICs of 2 and 10.

PMB is known to have membrane permeabilization and bactericidal properties. PMB has a hydrophobic acyl group and a macrocylic heptapeptide containing a D amino acid and four diaminobutyric acid (DAB) residues. One of the DAB side chains is involved in forming the macrocylic ring, leaving the other three side chains with free amines. Thus, PMB has an array of amines oriented on one face, or plane, of a hydrophobic scaffolding. It has been suggested that the primary role of the macrocylic ring is to orient the amine groups in a specific arrangement necessary for binding the lipid A portion of LPS. The relative spatial orientation of these primary amine groups is the same in the cholic acid derivatives as in PMB.

The stereochemistry of the steroid backbone results in different activities of the cholic acid derivatives (compare 2 and 8, Tables 1, 2, 6 and 7). Compounds with guanidine groups attached to the steroid have lower MIC values than compounds containing amine groups (compare 1, 2, 4 and 5, compare Tables 1–8). The length of the tether between the amine or guanidine groups and the steroid backbone also influences activity (compare 1–3, Tables 1, 2, 6 and 7). Ester tethers between amine groups and the steroid backbone provide compounds with MIC values that are higher than the corresponding compounds containing ether tethers (compare 1, 2, 6 and 7, Tables 1 and 2).

The group attached to the backbone at C-20 or C-24 also influences the activity of the cholic acid derivatives. A long carbon chain attached to the steroid via an ether linkage at C-24 lowers the MIC of the compound as compared to the compound with a hydroxyl group at C-24 (compare 2, 9 and 10, Tables 1, 2, 6 and 7). Short chains of carbon or oxygen attached at C-20 decrease the MIC values of the cholic acid derivatives (compare 10 and 11, Tables 1 and 2). Covalently linking the cholic acid derivatives increases the activity of the compounds (compare 10 and 12, Tables 1 and 2).

Ability to permeabilize outer membrane: Compounds 11, 106, and 108–114 (FIG. 1) were tested for antibiotic activity. They were also tested for the ability to permeabilize the outer membrane of Gram-negative bacteria, causing sensitization to hydrophobic antibiotics that cannot cross the outer membrane. The permeabilization of the outer membrane was measured using erythromycin and novobiocin. These antibiotics are active against Gram-positive bacteria, but inactive against Gram-negative bacteria, due to the barrier formed by the outer membrane of Gram-negative bacteria.

Most of the experiments were performed with *Escherichia coli* K-12 strain ATCC 10798; however, to demonstrate that the activity of the cholic acid derivatives was not species dependent, the activity of selected compounds was also measured with *Pseudomonas aeruginosa* (ATCC 27853). The MICs of erythromycin and novobiocin against *E. coli* (ATCC 10798) at 70 and >500 µg/mL were measured. The threshold measure of permeabilization was the concentration of the cholic acid derivatives required to lower the MIC of either erythromycin or novobiocin to 1 µg/mL.

Figure 2:
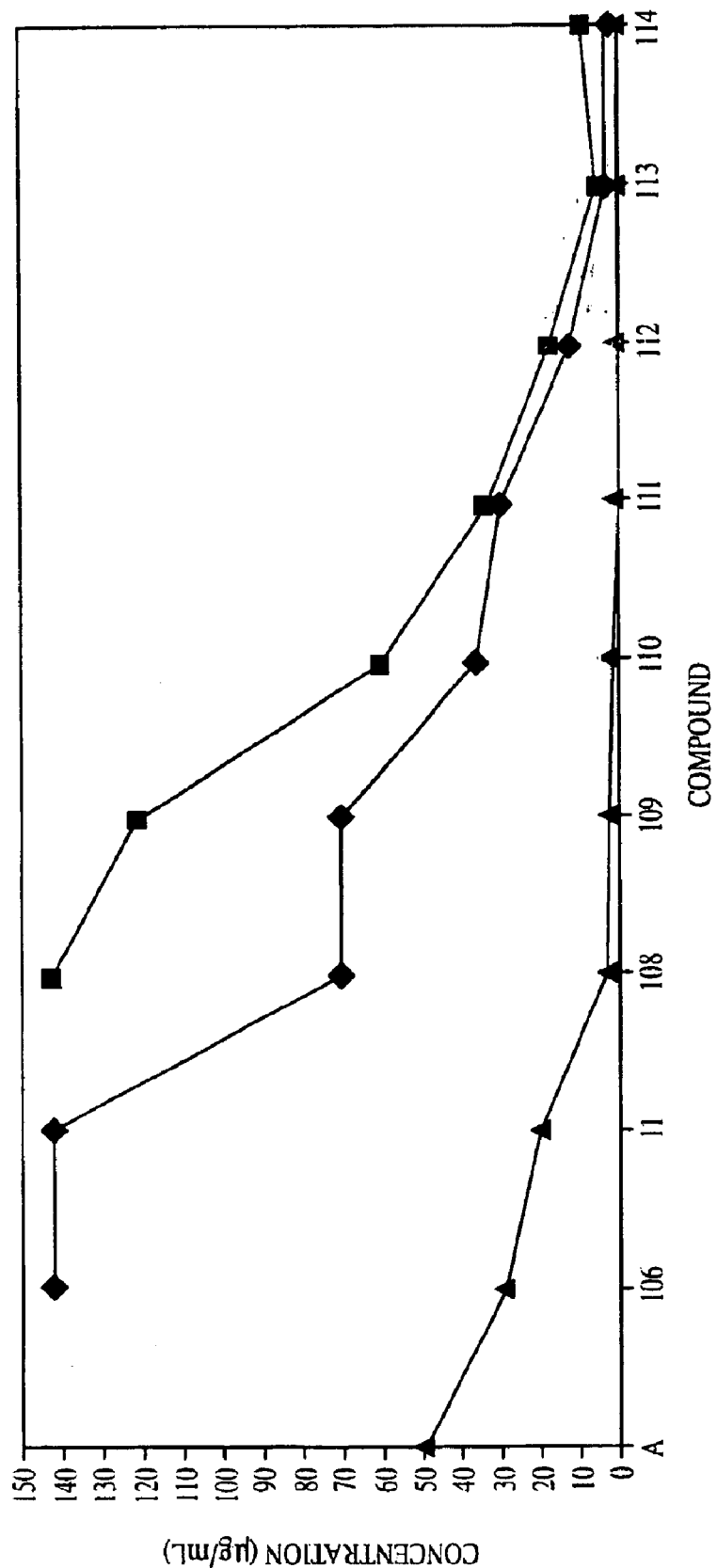
FIG. 2 is a graph showing the concentrations of compounds of the invention required to lower the MIC of erythromycin to 1 μg/ml, as well as MIC and MBC values of each of the compounds.
Figure 3:
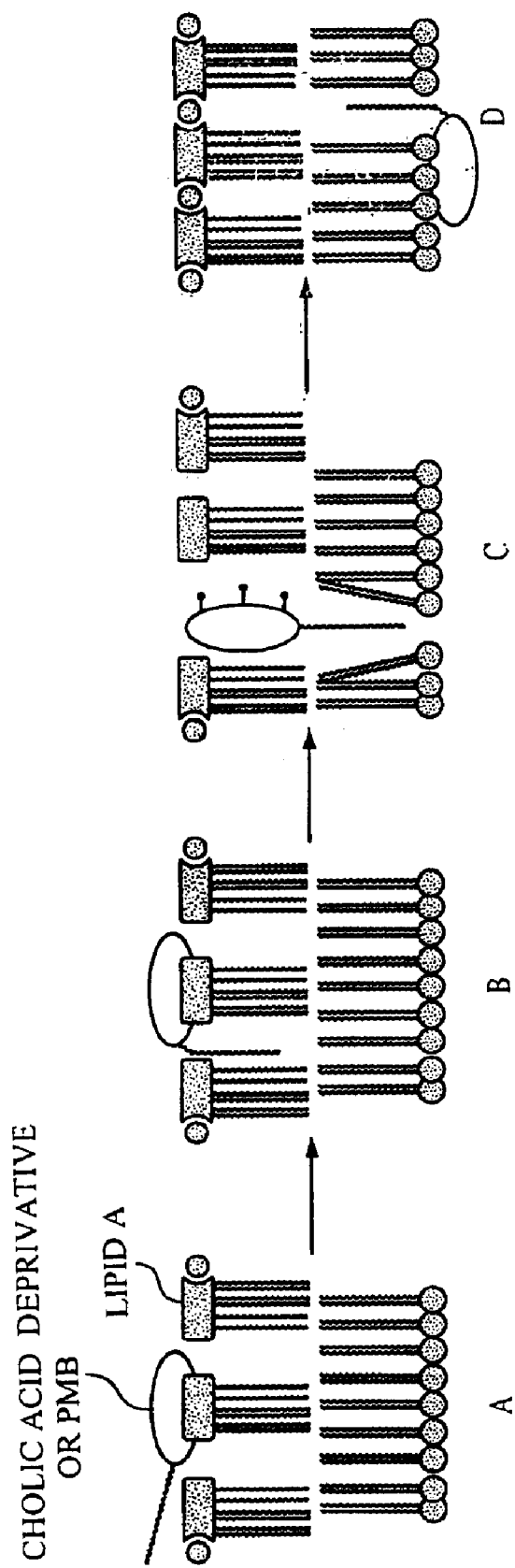
FIG. 3 is a scheme showing the proposed mechanism of action of cholic acid derivatives.

Results of the MIC, MBC and permeabilization (with erythromycin) measurements are shown in FIG. 2 (in FIG. 2, Compound A is polymyxin B nonapeptide). As FIG. 2 illustrates, the MIC and MBC values of the compounds dropped dramatically as the length of the side chain extending from C-17 increased. The apparent role of the hydrophobic steroid side chain is to facilitate membrane insertion and self-promoted transport after initial association with the outer membrane of Gram-negative bacteria (as shown in FIG. 3). Outer membrane permeabilization occurs as a result of association with the lipid A on the outer leaflet of the membrane. Permeabilization of the outer membrane alone does not cause cell death, suggesting that the compounds must pass through the outer membrane to kill bacteria. This ability to traverse the outer membrane, and thereby disrupt the cytoplasmic membrane, is required for the compounds to have lethal activity.

As observed, compounds lacking a hydrophobic side chain are less effective in killing bacteria. It is hypothesized that these compounds are capable of permeabilizing the outer membrane (i.e., associating with the lipid A on the outer leaflet of the membrane), but incapable of crossing through the outer membrane.

The fractional inhibition concentration (FIC) values of the compounds, were calculated using erythromycin and novobiocin as the secondary compounds. With the exception of 114, the compounds displayed FIC values of less than 0.5 with erythromycin, with some values near 0.05 (Table 9).

Details from studies with novobiocin are also shown in Table 9. The fact that results with erythromycin and novobiocin were comparable demonstrates that the activity of the cholic acid derivatives is not antibiotic-dependent. Similar trends were observed with *E. coli* (ATCC 10798) and *P. aeruginosa* (ATCC 27853), although, as expected, *P. aeruginosa* was more resistant than *E. coli*. These results suggest that the activity of the compounds tested is not species-dependent.

Figure 4:
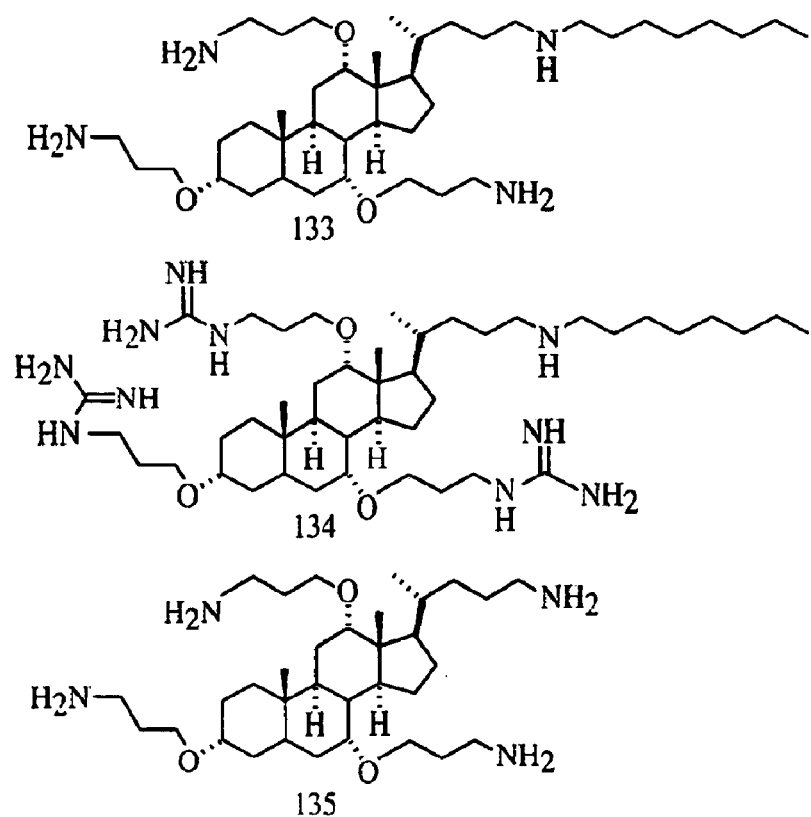
FIG. 4 is a drawing showing compounds of the invention.
Figure 5:
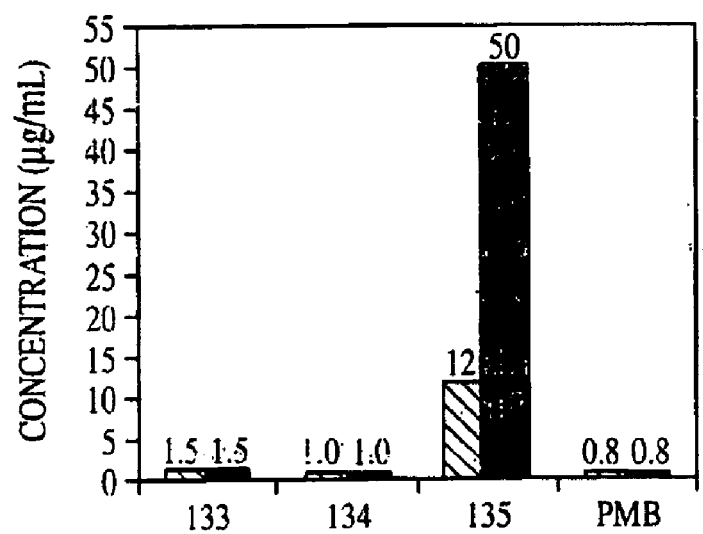
FIG. 5 is a graph showing MIC and MBC values for compounds of the invention.

Compounds with hydrophobic alkylaminoalkyl side chains were prepared (compounds 133 and 134, FIG. 4). As observed with other compounds, the incorporation of guanidine groups (in 134) increased the activity of the cholic acid derivatives as compared to compounds containing primary amines. As a control, 135 (FIG. 4), which did not have a hydrophobic side chain, was prepared. The MIC of the control (135) was relatively high, as expected, as was the MBC (FIG. 5). In contrast, the MICs of 133 and 134 were very low; in fact they rivaled PMB in activity. Notably, the MBCs of 133, 134, and PMB were very similar to the MICs; that is, at a threshold concentration these compounds killed all of the bacteria in solution.

As an additional means of demonstrating the membrane disrupting capabilities of the cholic acid derivatives 133 and 134, a luciferin/luciferase-based cell lysis assay was used (as described in Willardson et al., *Appl. Environ. Microbiol.* 1998, 64, 1006 and Schupp et al., *Biotechniques* 1995, 19, 18). In this assay, *E. coli* containing an inducible luciferase coding plasmid was incubated with the inducing agent (toluene), then treated with a lysis buffer containing either PMB or one of the cholic acid derivatives, and Triton X-100. Luciferin and ATP were then added. Cell lysis resulted in luminescence. The concentrations of the membrane disrupting agents (PMB and the cholic acid derivatives) were varied, and the resulting luminescence was measured. In the absence of the membrane disrupting agents, no luminescence was observed.

Figure 6:
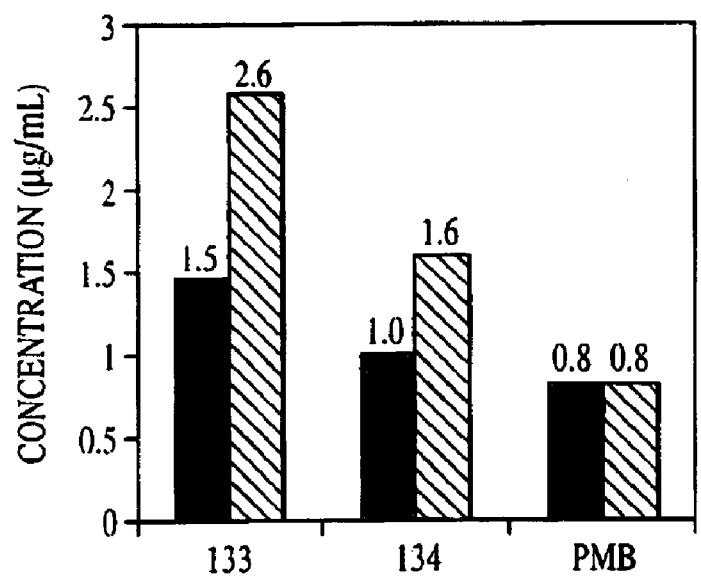
FIG. 6 is a graph showing MIC values for compounds of the invention.

The MICs of 133, 134 and PMB and the concentrations required for half maximal luminescence are shown in FIG. 6. As is the case with the MIC values, the compounds 133 and 134 rival PMB in activity in the luminescence assay.

Figure 7:
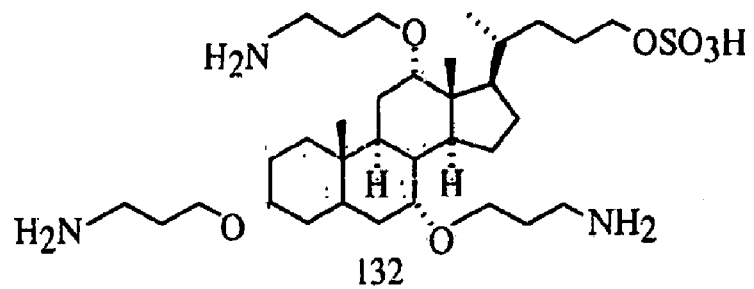
FIG. 7 is a drawing showing compound 132.
Figure 7:
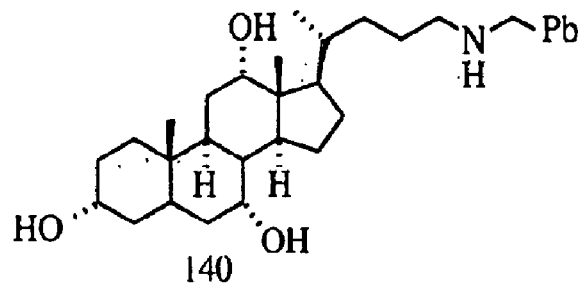

Effect of sulfate group: To observe if the presence of a sulfate group at C-24 in a cholic acid derivative would increase the activity of the compounds, 132 (shown in FIG. 7) was tested. The MIC of 132 with *E. coli* (ATCC 10798) was 60 μg/mL. The concentration required to lower the MIC of erythromycin to 1 μg/mL was 4.0 μg/mL with the same strain. The antibiotic and permeabilization activities of 132 were lower than those of the parent alcohol 110 (shown in FIG. 1).

Additional experiments: Additional experiments were carried out using compounds 1, 2, 5, 106, 10, 112, 133, and 134. MIC and MBC data for these compounds with representative strains of Gram-negative and Gram-positive organisms are shown in Table 10. For comparison purposes, the MICs of PMB with various organisms were also measured and are presented in Table 10.

In addition to PMB, compounds 1, 2, 5, 106, 10, 112, 133, and 134 share some features with other steroid antibiotics. For example, squalamine includes a steroid nucleus and a polyamine side chain (Moore et al., *Proc. Natl. Acad. Sci.* 1993, vol. 90, 1354–1358). It is proposed that squalamine incorporates into lipid bilayers and thus disrupts the bacterial membrane. In squalamine, the polar polyamine functionality is located at the distal end of the molecule, leaving a hydrophobic core. In 1, 2, 5, 106, 10, 112, 133, and 134, the amines are located on one side of the steroid, giving compounds that are facially amphiphilic. An additional series of compounds related to 1, 2, 5, 106, 10, 112, 133, and 134 includes cholic acid derivatives with amines at C-24 (e.g., 140 in FIG. 7). In contrast to 1, 2, 5, 106, 10, 112, 133, and 134, these compounds have been shown to have only weak antibacterial activity against Gram-positive strains and no activity against Gram-negative strains.

The cholic acid derivatives 1, 2, 5, 106, 10, 112, 133, and 134 display a range of activities, some with submicrogram per milliliter MICs. With many organisms, MIC and MBC values are very similar, especially with the most active compounds. Some of the compounds have lethal activity, presumably due to disruption of the cytoplasmic membrane. Others have only sublethal activity, due to permeabilization of the outer membrane.

Compounds lacking a hydrophobic chain (e.g., 106 and 10) have high MIC values, but are effective permeabilizers of the outer membrane of Gram-negative bacteria. Because these compounds lack a hydrophobic chain, they have sublethal, but not lethal activity against these bacteria. Compounds with hydrophobic chains (e.g., 133 and 134) have lethal activity.

The hemolytic behavior of the cholic acid derivatives 1, 2, 5, 106, 10, 112, 133, and 134 suggests that they can act as membrane-disrupting agents, and their antimicrobial activity likely involves membrane disruption. With Gram-negative strains, the target of inactivity is expected to be the cytoplasmic membrane. Compounds such as 106 and 10 ineffectively cross the outer membrane and do not display lethal activity. The hydrophobic chains in 133 and 134 may facilitate self-promoted transport across the outer membrane, allowing them to disrupt the cytoplasmic membrane.

The results shown in Table 10 indicate that the presence of a hydrophobic chain is much less important for lethal activity against Gram-positive strains. Without the requirement for crossing an outer membrane, compounds lacking a hydrophobic chain extending from C-17 can effectively kill Gram-positive bacteria.

Various tether lengths were investigated to determine the optimal spacing of the amine or guanidine groups from the steroid. It was found that three carbon tethers gave compounds that were more effective than those with two carbon tethers (e.g., compare the MICs of 1 with those of 2. The resultant increase in antibiotic activity upon substitution of guanidine groups for amines suggests a central role for amine/guanidine-phosphate interactions.

The nature of the group attached to the steroid backbone at C-17 greatly influenced the activity of the compounds with Gram-negative bacteria. For example, the differences among the MIC and MBC values for 106, 10, and 112 were notable. This trend was also observed in the MIC and MCB values of 2 and 5, as compared to those of 133 and 134 (in this comparison, the benzyl groups in 2 and 5 are expected to be less hydrophobic than the octyl chains found in 133 and 134). The influence of the group attached to the steroid at C-17 is less pronounced with Gram-positive strains; e.g., 5 and 134 have similar MIC values with *Staphylococcus aureus*.

To measure permeabilization, the FIC values for compounds 1, 2, 5, 106, 10, 112, 133, and 134 with erythromycin, novobiocin, and rifampicin were determined. Concentrations of 0.5, 1.0 or 3.0 μg/mL of these antibiotics were used, and the concentrations of the cholic acid derivatives required to inhibit bacterial growth of Gram-negative strains were determined. The concentrations required for bacterial growth inhibition and the FIC values are shown in Tables 11–13. Interestingly, the MIC values of the compounds do not directly correlate with their ability to permeabilize the outer membrane. For example, compounds 106 and 10 have relatively high MIC values, but are potent permeabilizers. Nearly all of the compounds demonstrated FIC values of less than 0.5, with some less than 0.03. The cholic acid derivatives that give relatively high FIC values (i.e., 5, 133, and 134) are themselves potent antibiotics.

Ester and amide side chains: Additional compounds, for example, compounds with amide and ester side chains, were tested. Compounds 203b, 6, and 210a (Scheme 12) displayed potent synergism with erythromycin and novobiocin (Table 14). In the triester series (203a, 203b, 6, and 7), the β-alanine derived compounds are more active than those derived from glycine. Substitution at C24 had minimal effect on the activity of these compounds (compare 203b and 7).

Triamides 209a–c (Scheme 12) were less active than the esters, possibly due to conformational constraints imposed by the amide bonds. With the triamides, substitution at C24 had significant effects on the activity of the compounds (compare 209a and 210a, Table 14). In this series, the glycine derivative was more active than the corresponding β-alanine derivative.

Figure 8:
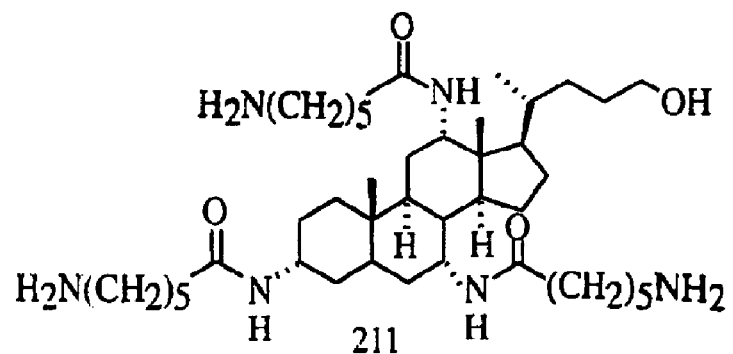
FIG. 8 is a drawing showing compound 211.

The relative lack of synergism displayed by the lysine derivative may be attributable to the length of the side chain. As a control, compound 211 (FIG. 8), a derivative of 209c lacking the α-amino group, was prepared; this compound was less active than 209c as a permeabilizer. Compound 206 also proved to be ineffective as a permeabilizer. These results suggest that the optimal length for the tether between the steroid and the amine functionality is between zero and six atoms.

Figure 11:
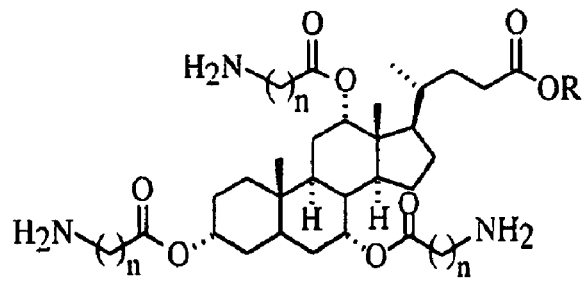
FIG. 11 is a drawing showing compounds 341–343 and 324–327.
Figure 12:
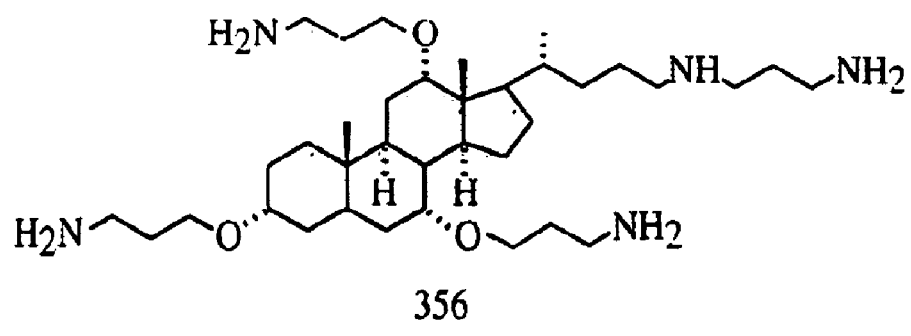
FIG. 12 is a drawing showing compounds 356–358.
Figure 12:
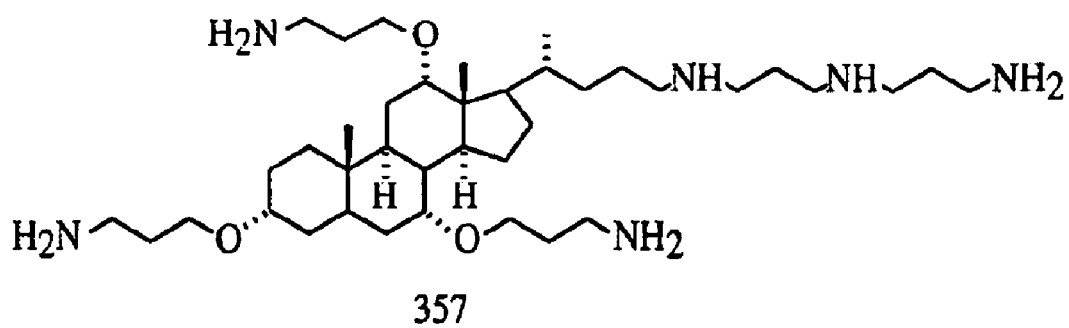
Figure 12:
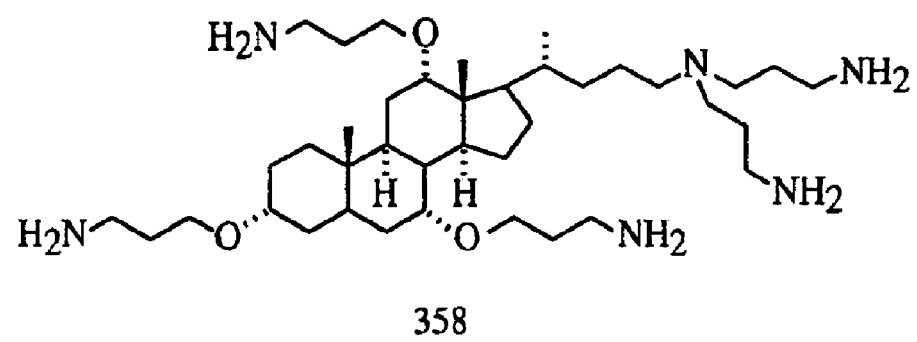

Further compounds 341–343 and 324–327 were investigated similarly. The structures of compounds 341–343 and 324–327 are shown in FIG. 11. The MIC of these compounds against *S. aureus* (ATTC 25923) are presented in Table 16 as $MIC^a$, the MIC of these compounds against *E. coli* (ATTC 25922) are presented in Table 16 as $MIC^b$, the concentration of the compounds required to lower the MIC of erythromycin from 30 to 1 μg/mL with *E. coli* is shown in Table 16 as c, and the minimum hemolytic concentration of the compounds is shown in Table 16 as $MHC^d$. Minimum inhibition concentrations (MIC) and minimum hemolytic concentrations (MHC) were measured as described in Li et al., *Antimicrob. Agents. Chemother.,* 1999, 43, 1347. The compounds in Table 16 containing a hydrophobic chain at carbon 24 (341–343) were the most active against the Gram-negative strain. The compounds with choline at carbon 24 (324–326) were much less active alone against the Gram-negative strain, yet retained the ability to inhibit the growth of the Gram-positive strain. This difference may be due to the inability of compounds 324–326 to traverse the ourter membrane of the Gram-negative strain studied here. Compound 327 was inactive. Compounds 341–343 exhibited very low MHC; however, compounds 324–326 appear to be non-hemolytic, presumably due to the additional positive charge at carbon 24. The structures of compounds 356–358 are shown in FIG. 12. An outline of the synthesis of compounds 356–357 is shown in Scheme 16.

TABLE 1

Measurement of MIC and MBC values of 1–12 with *E. coli* (ATCC 10798)

| Compound | MIC (µg/mL) | MBC (µg/mL) |
|---|---|---|
| 1 | 20 | 34 |
| 2 | 7 | 16 |
| 3 | 6 | a |
| 4 | 5 | 10 |
| 5 | 2 | 4 |
| 6 | 65 | a |
| 7 | 28 | a |
| 8 | 46 | a |
| 9 | 3 | 10 |
| 10 | 36 | 60 |
| 11 | 140 | >160 |
| 12 | 4 | 4 | a Value not measured.

TABLE 2

Measurement of the concentrations of 1–12 required to lower the MIC of erythromycin from 70 µg/mL to 1 µg/mL with *E. coli* (ATCC 10798).

| Compound | MIC (µg/mL) | MBC (µg/mL) |
|---|---|---|
| 1 | 2 | 20 |
| 2 | 1 | 10 |
| 3 | 1.5 | a |
| 4 | 1.5 | 10 |
| 5 | 1 | 3 |
| 6 | 22 | a |
| 7 | 2.5 | a |
| 8 | 10 | a |
| 9 | 3 | 3 |
| 10 | 2 | 50 |
| 11 | 40 | >160 |
| 12 | 1.5 | 2.5 | aValue not measured.

TABLE 3

Measurement of the concentrations of 1, 2, 4 and 5 required to lower the MIC of novobiocin from >500 µg/mL to 1 µg/mL with *E. coli* (ATCC 10798).

| Compound | MIC (µg/mL) | MBC (µg/mL) |
|---|---|---|
| 1 | 20 | 34 |
| 2 | 7 | 16 |
| 4 | 5 | 10 |
| 5 | 2 | 4 |

TABLE 3-continued

Measurement of the concentrations of 1, 2, 4 and 5 required to lower the MIC of novobiocin from >500 µg/mL to 1 µg/mL with *E. coli* (ATCC 10798).

| Compound | MIC (µg/mL) | MBC (µg/mL) |
|---|---|---|
| 11 | 40 | 140 |
| 12 | 2.5 | a | aValue not measured.

TABLE 4

Measurement of MIC and MBC values of 1, 2, 4 and 5 with *E. coli* (ATCC 25922).

| Compound | MIC (µg/mL) | MBC (µg/mL) |
|---|---|---|
| 1 | 25 | 40 |
| 2 | 10 | 20 |
| 4 | 6 | 9 |
| 5 | 2 | 4 |

TABLE 5

Measurement of the concentrations of 1, 2, 4 and 5 required to lower the MIC of erythromycin from 60 µg/mL to 1 µg/mL with *E. coli* (ATCC 25922).

| Compound | MIC (µg/mL) | MBC (µg/mL) |
|---|---|---|
| 1 | 2 | 14 |
| 2 | 1 | 5 |
| 4 | 1 | 5 |
| 5 | 1.5 | 1.5 |

TABLE 6

Measurement of MIC and MBC values of 1–5, 8–12 with *P. aureginosa* (ATCC 27853).

| Compound | MIC (µg/mL) | MBC (µg/mL) |
|---|---|---|
| 1 | 15 | >50 |
| 2 | 9 | 40 |
| 3 | 16 | a |
| 4 | 15 | 40 |
| 5 | 6 | 15 |
| 8 | 50 | a |
| 9 | 8 | a |
| 10 | 23 | a | aValue not measured.

TABLE 7

Measurement of the concentrations of 1–5, 8–12 required to lower the MIC of erytbromycin from 240 µg/mL to 5 µg/mL with *P. aureginosa* (ATCC 27853).

| Compound | MIC (µg/mL) | MBC (µg/mL) |
|---|---|---|
| 1 | 8 | 45 |
| 2 | 4 | 25 |
| 3 | 6 | a |
| 4 | 5 | 40 |
| 5 | 3 | 10 |
| 8 | 40 | a |
| 9 | 5 | a |
| 10 | 7 | a | aValue not measured.

TABLE 8

Measurement of the concentrations of 1, 2, 4 and 5 required to lower the MIC of novobiocin from >500 μg/mL to 1 μg/mL with *P. aureginosa* (ATCC 27853).

| Compound | MIC (μg/mL) |
|---|---|
| 1 | 6 |
| 2 | 4 |
| 4 | 6 |
| 5 | 6 |

TABLE 9

| Compound | MIC (μg/mL) | MBC (μg/mL) | (a) (μg/mL) | (b) (μg/mL) | FIC[c] | (d) (μg/mL) | FIC[e] |
|---|---|---|---|---|---|---|---|
| 106 | 140 | >200 | 30 | 160 | 0.23 | 50 | 0.36 |
| 11 | 140 | >160 | 20 | 180 | 0.16 | 40 | 0.29 |
| 108 | 70 | 140 | 4.0 | 140 | 0.071 | 12 | 0.17 |
| 109 | 70 | 120 | 4.0 | 80 | 0.071 | 15 | 0.22 |
| 110 | 36 | 60 | 2.0 | 50 | 0.070 | 4.0 | 0.11 |
| 111 | 30 | 33 | 1.0 | 20 | 0.048 | 2.0 | 0.069 |
| 112 | 12 | 17 | 0.4 | 4.0 | 0.048 | 0.8 | 0.085 |
| 113 | 3.0 | 5.0 | 0.8 | 2.0 | 0.28 | 1.0 | 0.27 |
| 114 | 3.0 | 10 | 3.0 | 3.0 | 1.0 | n.d. | n.d. |

MIC, MBC, permeabilization and FIC data with *Escherichia coli* (ATCC 10798).
(a) Concentration required to lower the MIC of erythromycin from 70 to 1 μg/mL.
(b) MBC with 1 μg/mL erythromycin.
(c) FIC values with erythromycin.
(d) Concentration required to lower the MIC of novobiocin from >500 to 1 μg/mL.
(e) FIC values with novobiocin.

TABLE 10

| | 1 (μg/mL) | | 2 (μg/mL) | | 5 (μg/mL) | | 106 (μg/mL) | | 10 (μg/mL) | | 112 (μg/mL) | | 133 (μg/mL) | | 134 (μg/mL) | | PMB (1) | |
|---|---|---|---|---|---|---|---|---|---|---|---|---|---|---|---|---|---|---|
| ORGANISM | MIC | MBC | MIC | MBC | MIC | MBC | MIC | MBC | MIC | MBC | MIC | MBC | MIC | MBC | MIC | MBC | MIC | MBC |
| Gram-negative rods | | | | | | | | | | | | | | | | | | |
| *Escherichia coli* ATCC 25922 | 22 | 22 | 5.1 | 6.8 | 1.4 | 3.8 | 80 | 90 | 36 | 40 | 6.6 | 7.4 | 3.0 | 3.0 | 0.31 | 0.37 | 1.8 | 1.8 |
| *Klebsiella pneumonia* ATCC 13883 | 24 | >36 | 14 | 17 | 3.0 | 6.7 | >100 | 100 | 47 | 50 | 23 | 27 | 2.6 | 5.8 | 0.84 | 3.0 | 5.3 | 6.8 |
| *Pseudomonas aeruginosa* ATCC 27853 | 26 | 38 | 11 | >17 | 5.9 | 9.9 | 85 | 97 | 21 | 36 | 4.6 | 6.4 | 2.0 | 3.2 | 2.0 | 2.9 | 0.20 | 3.9 |
| *Salmonella typhimurium* ATCC 14028 | 21 | >25 | 13 | 16 | 2.2 | 3.8 | >100 | >100 | 43 | >17 | 86 | 90 | 2.6 | 6.7 | 0.81 | 1.8 | nm | nm |
| Gram-positive cocci | | | | | | | | | | | | | | | | | | |
| *Enterococcus faecalis* ATCC 29212 | 4.9 | 50 | 3.4 | 19 | 2.2 | 16 | 12 | >100 | 3.3 | 19 | 3.1 | 4.7 | 3.1 | 5.5 | 3.0 | 5.8 | 40 | >100 |
| *Staphylococcus aureus* ATCC 25923 | 3.1 | 5.7 | 1.0 | 4.7 | 0.6 | 3.2 | 8.6 | 54 | 2.0 | 9.2 | 0.55 | 4.2 | 0.4 | 2.0 | 0.59 | 1.4 | 26 | >100 |
| *Streptococcus pyogenes* ATCC 19615 | 3.0 | 4.4 | 2.0 | 2.3 | 2.0 | 2.1 | 18 | 37 | 4.2 | 5.8 | 2.4 | 3.0 | 2.3 | 2.9 | 3.5 | 3.5 | 9.0 | 16.3 |
| *Candida albicans* ATCC 90028 | 49 | >50 | 30 | 42 | 11 | 50 | 75 | 92 | 14 | 29 | 41 | 45 | 31 | 45 | 53 | 76 | | |
| MHC | | 78 | | 58 | | 26 | | >100 | | 100 | | 5.9 | | 29 | | 9.0 | | |

TABLE 11

| | 1 | | 2 | | 5 | | 106 | | 10 | | 112 | | 133 | | 134 | |
|---|---|---|---|---|---|---|---|---|---|---|---|---|---|---|---|---|
| ORGANISM | a | μg/mL | FIC | μg/mL | FIC | μg/mL | FIC | μg/mL | FIC | μg/mL | FIC | μg/mL | FIC | μg/mL | FIC | μg/mL | FIC |
| *Escherichia coli* ATCC 25922 | 30 | 2.5 | 0.15 | 0.23 | 0.078 | 0.38 | 0.31 | 3.2 | 0.073 | 1.5 | 0.074 | 0.59 | 0.12 | 1.2 | 0.42 | 0.37 | 0.36 |
| *Klebsiella pneumonia* ATCC 13883 | 33 | 1.0 | 0.072 | 0.25 | 0.048 | 0.15 | 0.080 | 3.6 | 0.66 | 0.21 | 0.035 | 0.1 | 0.035 | 0.11 | 0.073 | 0.18 | 0.24 |
| *Pseudomonos aeruginosa* ATCC 27853 | >100 | 6.6 | 0.29 | 2.4 | 0.25 | 2.3 | 0.42 | 16 | 0.22 | 2.1 | 0.13 | 1.0 | 0.59 | 0.35 | 0.21 | 0.70 | 0.42 |
| *Salmonella typhimurium* ATCC 14028 | 61 | 3.6 | 0.19 | 2.0 | 0.17 | 0.46 | 0.23 | 7.1 | 0.088 | 0.87 | 0.037 | 0.20 | 0.019 | 0.72 | 0.29 | 0.34 | 0.44 |

TABLE 12

| ORGANISM | a | 1 µg/mL | FIC | 2 µg/mL | IC | 106 µg/mL | FIC | 10 µg/mL | FIC | 112 µg/mL | FIC |
|---|---|---|---|---|---|---|---|---|---|---|---|
| Escherichia coli ATCC 25922 | 41 | 0.35 | 0.041 | 0.33 | 0.089 | 4.7 | 0.084 | 0.30 | 0.033 | 0.40 | 0.085 |
| Klebsiella pneumonia ATCC 13883 | 75 | 4.7 | 0.21 | 0.49 | 0.048 | 8.9 | 0.10 | 0.73 | 0.029 | 0.19 | 0.022 |
| Pseudomonas aeruginosa ATCC 27853 | >100 | 3.9 | 0.16 | 2.9 | 0.27 | 30 | 0.36 | 5.3 | 0.26 | 0.72 | 0.17 |
| Salmonella typhimurium ATCC 14028 | >100 | 4.4 | 0.22 | 4.5 | 0.36 | 8.4 | 0.094 | 1.8 | 0.052 | 0.39 | 0.015 |

TABLE 13

| ORGANISM | a | 1 µg/mL | FIC | 2 µg/mL | IC | 106 µg/mL | FIC | 10 µg/mL | FIC | 112 µg/mL | FIC |
|---|---|---|---|---|---|---|---|---|---|---|---|
| Escherichia coli ATCC 25922 | 7.6 | 0.74 | 0.099 | 0.80 | 0.22 | 4.2 | 0.12 | 0.70 | 0.085 | 0.81 | 0.19 |
| Klebsiella pneumonia ATCC 13883 | 19 | 0.40 | 0.043 | 0.12 | 0.035 | 1.8 | 0.044 | 0.16 | 0.030 | 0.11 | 0.031 |
| Pseudomonas aeruginosa ATCC 27853[b] | 26 | 1.5 | 0.096 | 0.50 | 0.086 | 11 | 0.17 | 0.84 | 0.083 | 0.50 | 0.15 |
| Salmonella typhimurium ATCC 14028[b] | 21 | 0.84 | 0.089 | 0.39 | 0.079 | 1.4 | 0.064 | 0.55 | 0.063 | 0.10 | 0.051 |

TABLE 14

| Compound | MIC (µg/mL) | a (µg/mL) | b (µg/mL) |
|---|---|---|---|
| 203a | 85 | 18 | 55 |
| 203b | 80 | 4 | 10 |
| 6 | 85 | 15 | 40 |
| 7 | 70 | 3 | 13 |
| 209a | >100 | 25 | 75 |
| 209b | >100 | 40 | 75 |
| 209c | 85 | 45 | 60 |
| 210a | 80 | 6 | 18 |
| 210b | 100 | 15 | 40 | a: concentration of cholic acid derivatives required to lower MIC of erythromycin to 1 µg/ML.
b: concentration of cholic acid derivatives required to lower MIC of novobiocin to 1 µg/ML.

TABLE 15

| Compound | pH 2.0 | pH 7.0 | pH 12.0 |
|---|---|---|---|
| 352 | >37 days | 28 days | <30 minutes |
| 353 | >37 days | 37 days | <30 minutes |
| 354 | 33 days | 12 days | <30 minutes |

TABLE 16

| Compound | MIC (µg/mL) | MIC (µg/mL) | c (µg/mL) | MHC (µg/mL) |
|---|---|---|---|---|
| 341 | 1.8 | 1.0 | 0.7 | 4.0 |
| 342 | 4.0 | 7.0 | 3.0 | 2.0 |
| 343 | 1.2 | 3.5 | 3.5 | <10 |
| 324 | 15 | 60 | 10 | >200 |
| 325 | 11 | 30 | 2.0 | >200 |
| 326 | 14 | 23 | 2.0 | >200 |
| 327 | >100 | >100 | >100 | >100 |

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For examples, salts, esters, ethers and amides of novel steroid compounds disclosed herein are within the scope of this invention. Thus, other embodiments are also within the claims.

What is claimed is:

1. A compound according to formula I

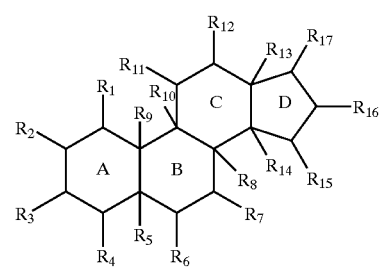

wherein:
fused rings A, B, C, and D are independently saturated or fully or partially unsaturated; and
$R_1$ through $R_4$, $R_6$, $R_7$, $R_{11}$, $R_{12}$, $R_{15}$, $R_{16}$, and $R_{17}$ is each independently selected from the group consisting of hydrogen, hydroxyl, a substituted or unsubstituted (C1–C10) alkyl, (C1–C10) hydroxyalkyl, (C1–C10) alkyloxy-(C1–C10) alkyl, (C1–C10) alkylcarboxy-(C1–C10) alkyl, (C1–C10) alkylamino-(C1–C10) alkyl, (C1–C10) alkylamino-(C1–C10) alkylamino, (C1–C10) alkylamino-(C1–C10) alkylamino-(C1–C10) alkylamino, a substituted or unsubstituted (C1–C10) aminoalkyl, a substituted or unsubstituted aryl, a substituted or unsubstituted arylamino-(C1–C10) alkyl, (C1–C10) haloalkyl, C2–C6 alkenyl, C2–C6 alkynyl, oxo, a linking group attached to a second steroid, a substituted or unsubstituted (C1–C10) aminoalkyloxy, a substituted or unsubstituted (C1–C10) aminoalkyloxy-(C1–C10) alkyl, a substituted or unsubstituted (C1–C10) aminoalkylcarboxy, a substituted or unsubstituted (C1–C10) aminoalkylaminocarbonyl, a substituted or unsubstituted (C1–C10) aminoalkylcarboxamido, H2N—HC(Q5)—C(O)—O—, H2N—HC(Q5)—C(O)—N(H)—, (C1–C10) azidoalkyloxy, (C1–C10) cyanoalkyloxy, P.G.-HN—HC(Q5)—C(O)—O—, (C1–C10) guanidinoalkyl oxy, (C1–C10) quaternaryammoniumalkylcarboxy, and (C1–C10) guanidinoalkyl carboxy, where Q5 is a side chain of any amino acid, P.G. is an amino protecting group, and $R_5$, $R_8$, $R_9$, $R_{10}$, $R_{13}$, and $R_{14}$ is each independently:
deleted when one of fused rings A, B, C, or D is unsaturated so as to complete the valency of the carbon atom at that site, or
selected from the group consisting of hydrogen, hydroxyl, a substituted or unsubstituted (C1–C10) alkyl, (C1–C10) hydroxyalkyl, (C1–C10) alkyloxy-(C1–C10) alkyl, a substituted or unsubstituted (C1–C10) aminoalkyl, a substituted or unsubstituted aryl, C1–C10 haloalkyl, C2–C6 alkenyl, C2–C6 alkynyl, a linking group attached to a second steroid, a substituted or unsubstituted (C1–C10) aminoalkyloxy, a substituted or unsubstituted (C1–C10) aminoalkylcarboxy, a substituted or unsubstituted (C1–C10) aminoalkylaminocarbonyl, H2N—HC(Q5)—C(O)—O—, H2N—HC(Q5)—C(O)—N(H)—, (C1–C10) azidoalkyloxy, (C1–C10) cyanoalkyloxy, P.G.-HN—HC(Q5)—C(O)—O—, (C1–C10) guanidinoalkyloxy, and (C1–C10) guanidinoalkylcarboxy, where Q5 is a side chain of any amino acid, P.G. is an amino protecting group, and provided that at least two of $R_1$ through $R_{14}$ are independently selected from the group consisting of a substituted or unsubstituted (C1–C10) aminoalkyloxy, (C1–C10) alkylcarboxy-(C1–C10) alkyl, (C1–C10) alkylamino-(C1–C10) alkylamino, (C1–C10) alkylamino-(C1–C10) alkylamino-(C1–C10) alkylamino, a substituted or unsubstituted (C1–C10) aminoalkylcarboxy, a substituted or unsubstituted arylamino-(C1–C10) alkyl, a substituted or unsubstituted (C1–C10) aminoalkyloxy-(C1–C10) alkyl, a substituted or unsubstituted (C1–C10) aminoalkylaminocarbonyl, (C1–C10) quaternaryammonium alkylcarboxy, H2N—HC(Q5)—C(O)—O—, H2N—HC(Q5)—C(O)—N(H)—, (C1–C10) azidoalkyloxy, (C1–C10) cyanoalkyloxy, P.G.-HN—HC(Q5)—C(O)—O—, (C1–C10) guanidinoalkyloxy, and (C1–C10) guanidinoalkylcarboxy, and further provided that $R^{12}$ cannot be hydrogen when all of the fused rings A, B, C, and D are saturated; or a pharmaceutically acceptable salt thereof.

2. The compound of claim 1, wherein at least three of $R_1$ through $R_{14}$ are independently selected from the group consisting of a substituted or unsubstituted (C1–C10) aminoalkyloxy, (C1–C10) alkylcarboxy-(C1–C10) alkyl, a substituted or unsubstituted (C1–C10) aminoalkylcarboxy, (C1–C10) alkylamino-(C1–C10) alkylamino, (C1–C10) alkylamino-(C1–C10) alkylamino-(C1–C10) alkylamino, a substituted or unsubstituted (C1–C10) aminoalkyl, a substituted or unsubstituted (C1–C10) aminoalkylaminocarbonyl, a substituted or unsubstituted (C1–C10) aminoalkylcarboxamido, a substituted or unsubstituted arylamino-(C1–C10) alkyl, a substituted or unsubstituted (C1–C10) aminoalkyloxy-(C1–C10) alkyl, H2N—HC(Q5)—C(O)—O—, H2N—HC(Q5)—C(O)—N(H)—, (C1–C10) azidoalkyloxy, (C1–C10) cyanoalkyloxy, (C1–C10) quaternaryammoniumalkylcarboxy, P.G.-HN—HC(Q5)—C(O)—O—, (C1–C10) guanidinoalkyloxy, and (C1–C10) guanidinoalkylcarboxy.

3. The compound of claim 1, wherein none of $R_5$, $R_8$, $R_9$, $R_{13}$, and $R_{14}$ is deleted.

4. The compound of claim 1, wherein each of $R_3$, $R_7$, and $R_{12}$ is independently selected from the group consisting of a substituted or unsubstituted (C1–C10) aminoalkyloxy, a substituted or unsubstituted (C1–C10) aminoalkylcarboxy, a substituted or unsubstituted (C1–C10) aminoalkylaminocarbonyl, a substituted or unsubstituted (C1–C10) aminoalkylcarboxamido, H2N—HC(Q5)—C(O)—O—, H2N—HC(Q5)—C(O)—N(H)—, (C1–C10) azidoalkyloxy, (C1–C10) cyanoalkylcarboxy, P.G.-HN—HC(Q5)—C(O)—O—, (C1–C10) guanidinoalkyloxy, and (C1–C10) guanidinoalkylcarboxy, where Q5 is a side chain of any amino acid, P.G. is an amino protecting group or a pharmaceutically acceptable salt thereof.

5. The compound of claim 4, wherein $R_1$, $R_2$, $R_4$, $R_5$, $R_6$, $R_8$, $R_{10}$, $R_{11}$, $R_{13}$, $R_{14}$, $R_{15}$, and $R_{16}$ are hydrogen.

6. The compound of claim 5, wherein $R_{17}$ is —$CR_{18}R_{19}R_{20}$, where each of $R_{18}$, $R_{19}$, and $R_{20}$, is independently selected from the group consisting of hydrogen, hydroxyl, a substituted or unsubstituted (C1–C10) alkyl, (C1–C10) hydroxyalkyl, (C1–C10) alkyloxy-(C1–C10) alkyl, a substituted or unsubstituted (C1–C10) aminoalkyl, a substituted or unsubstituted aryl, (C1–C10) haloalkyl, (C2–C6) alkenyl, (C2–C6) alkynyl, oxo, and a linking group attached to a second steroid.

7. The compound of claim 4, wherein each of $R_3$, $R_7$, and $R_{12}$, is independently selected from the group consisting of —O—(CH2)n-NH2, —O—CO—(CH2)n-NH2, —O—(CH2)n-NH—C(NH)—NH2, —O—(CH2)n-N3, —O—(CH2)n-CN, where n is 1 to 3, and —O—C(O)—HC(Q5)—NH2, where Q5 is a side chain of any amino acid.

8. The compound of claim 4, wherein each of $R_3$, $R_7$, and $R_{12}$, is —O—CO—(CH2)n-NH2, where n is 1 to 4.

9. The compound of claim 8, wherein R17 is —CH(CH$_3$)—(CH$_2$)$_n$—NR$^1$R$^2$, wherein n is 0–2, $R^1$ and $R^2$ are independently (C1–C6) alkyl, aryl or aralkyl.

10. A pharmaceutical composition comprising an effective amount of a compound of formula (I):

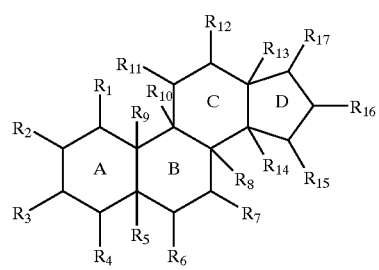

I wherein:
fused rings A, B, C, and D are independently saturated or fully or partially unsaturated; and $R_1$ through $R_4$, $R_6$, $R_7$, $R_{11}$, $R_{12}$, $R_{15}$, $R_{16}$, and $R_{17}$ is each independently selected from the group consisting of hydrogen, hydroxyl, a substituted or unsubstituted (C1–C10) alkyl, (C1–C10) hydroxyalkyl, (C1–C10) alkyloxy-(C1–C10) alkyl, (C1–C10) alkylcarboxy-(C1–C10) alkyl, (C1–C10) alkylamino-(C1–C10) alkyl, (C1–C10) alkylamino-(C1–C10) alkylamino, (C1–C10) alkylamino-(C1–C10) alkylamino-(C1–C10) alkylamino, a substituted or unsubstituted (C1–C10) aminoalkyl, a substituted or unsubstituted aryl, a substituted or unsubstituted arylamino-(C1–C10) alkyl, (C1–C10) haloalkyl, C2–C6 alkenyl, C2–C6 alkynyl, oxo, a linking group attached to a second steroid, a substituted or unsubstituted-(C1–C10) aminoalkyloxy, a substituted or unsubstituted (C1–C10) aminoalkyloxy-(C1–C10) alkyl, a substituted or unsubstituted (C1–C10) aminoalkylcarboxy, a substituted or unsubstituted (C1–C10) aminoalkylaminocarbonyl, a substituted or unsubstituted (C1–C10) aminoalkylcarboxamido, H2N—HC(Q5)—C(O)—O—, H2N—HC(Q5)—C(O)—N(H)—, (C1–C10) azidoalkyloxy, (C1–C10) cyanoalkyloxy, P.G.-HN—HC(Q5)—C(O)—O—, (C1–C10) guanidinoalkyl oxy, (C1–C10) quaternaryammonium-alkylcarboxy, and (C1–C10) guanidinoalkyl carboxy, where Q5 is a side chain of any amino acid, P.G. is an amino protecting group, and $R_5$, $R_8$, $R_9$, $R_{10}$, $R_{13}$, and $R_{14}$ is each independently:

deleted when one of fused rings A, B, C, or D is unsaturated so as to complete the valency of the carbon atom at that site, or selected from the group consisting of hydrogen, hydroxyl, a substituted or unsubstituted (C1–C10) alkyl, (C1–C10) hydroxyalkyl, (C1–C10) alkyloxy-(C1–C10) alkyl, a substituted or unsubstituted (C1–C10) aminoalkyl, a substituted or unsubstituted aryl, C1–C10 haloalkyl, C2–C6 alkenyl, C2–C6 alkynyl, a linking group attached to a second steroid, a substituted or unsubstituted (C1–C10) aminoalkyloxy, a substituted or unsubstituted (C1–C10) aminoalkylcarboxy, a substituted or unsubstituted (C1–C10) aminoalkylaminocarbonyl, H2N—HC(Q5)—C(O)—O—, H2N—HC(Q5)—C(O)—N(H)—, (C1–C10) azidoalkyloxy, (C1–C10) cyanoalkyloxy, P.G.-HN—HC(Q5)—C(O)—O—, (C1–C10) guanidinoalkyloxy, and (C1–C10) guanidinoalkylcarboxy, where Q5 is a side chain of any amino acid, P.G. is an amino protecting group, and provided that at least two of $R_1$ through $R_{14}$ are independently selected from the group consisting of a substituted or unsubstituted (C1–C10) aminoalkyloxy, (C1–C10) alkylcarboxy-(C1–C10) alkyl, (C1–C10) alkylamino-(C1–C10) alkylamino, (C1–C10) alkylamino-(C1–C10) alkylamino-(C1–C10) alkylamino, a substituted or unsubstituted (C1–C10) aminoalkylcarboxy, a substituted or unsubstituted arylamino-(C1–C10) alkyl, a substituted or unsubstituted (C1–C10) aminoalkyloxy-(C1–C10) alkyl, a substituted or unsubstituted (C1–C10) aminoalkylaminocarbonyl, (C1–C10) quaternaryammonium alkylcarboxy, H2N—HC(Q5)—C(O)—O—, H2N—HC(Q5)—C(O)—N(H)—, (C1–C10) azidoalkyloxy, (C1–C10) cyanoalkyloxy, P.G.-HN—HC(Q5)—C(O)—O—, (C1–C10) guanidinoalkyloxy, and (C1–C10) guanidinoalkylcarboxy; or a pharmaceutically acceptable salt thereof.

11. The pharmaceutical composition of claim 10, wherein the composition includes additional antibiotics.

12. A compound according to formula I

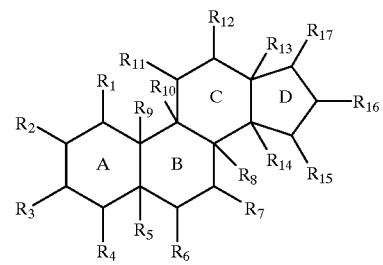

wherein:

fused rings A, B, C, and D are independently saturated or fully or partially unsaturated; and $R_1$ through $R_4$, $R_6$, $R_7$, $R_{11}$, $R_{12}$, $R_{15}$, and $R_{16}$, is each independently selected from the group consisting of hydrogen, hydroxyl, a substituted or unsubstituted (C1–C10) alkyl, (C1–C10) hydroxyalkyl, (C1–C10) alkyloxy-(C1–C10) alkyl, (C1–C10) alkylcarboxy-(C1–C10) alkyl, (C1—C10) alkylamino-(C1–C10) alkyl, (C1–C10) alkylamino-(C1–C10) alkylamino, (C1–C10) alkylamino-(C1–C10) alkylamino-(C1–C10) alkylamino, a substituted or unsubstituted (C1–C10) aminoalkyl, a substituted or unsubstituted aryl, a substituted or unsubstituted arylamino-(C1–C10) alkyl, (C1–C10) haloalkyl, C2–C6 alkenyl, C2–C6 alkynyl, oxo, a linking group attached to a second steroid, a substituted or unsubstituted (C1–C10) aminoalkyloxy, a substituted or unsubstituted (C1–C10) aminoalkyloxy-(C1–C10) alkyl, a substituted or unsubstituted (C1–C10) aminoalkylcarboxy, a substituted or unsubstituted (C1–C10) aminoalkylaminocarbonyl, a substituted or unsubstituted (C1–C10) aminoalkylcarboxamido, H2N—HC(Q5)—C(O)—O—, H2N—HC(Q5)—C(O)—N(H)—, (C1–C10) azidoalkyloxy, (C1–C10) cyanoalkyloxy, P.G.-HN—HC(Q5)—C(O)—O—, (C1–C10) guanidinoalkyl oxy, (C1–C10) quaternaryammonium-alkylcarboxy, and (C1–C10) guanidinoalkyl carboxy, where Q5 is a side chain of any amino acid, P.G. is an amino protecting group, and $R_5$, $R_8$, $R_9$, $R_{10}$, $R_{13}$, and $R_{14}$ is each independently:

deleted when one of fused rings A, B, C, or D is unsaturated so as to complete the valency of the carbon atom at that site, or selected from the group consisting of hydrogen, hydroxyl, a substituted or unsubstituted (C1–C10) alkyl, (C1–C10) hydroxyalkyl, (C1–C10) alkyloxy-(C1–C10) alkyl, a substituted or unsubstituted (C1–C10) aminoalkyl, a substituted or unsubstituted aryl, C1–C10 haloalkyl, C2–C6 alkenyl, C2–C6 alkynyl, a linking group attached to a second steroid, a substituted or unsubstituted (C1–C10) aminoalkyloxy, a substituted or unsubstituted (C1–C10) aminoalkylcarboxy, a substituted or unsubstituted (C1–C10) aminoalkylaminocarbonyl, H2N—HC(Q5)—C(O)—O—, H2N—HC(Q5)—C(O)—N(H)—, (C1–C10) azidoalkyloxy, (C1–C10) cyanoalkyloxy, P.G.-HN—HC(Q5)—C(O)—O—, (C1–C10) guanidinoalkyloxy, and (C1–C10) guanidinoalkylcarboxy, where Q5 is a side chain of any amino acid, P.G. is an amino protecting group, and $R_{17}$ is selected from the group consisting of substituted or unsubstituted alkylcarboxyalkyl and protected or unprotected poly(aminoalkyl), provided that at least two of $R_1$ through $R_{14}$ are independently selected from the group consisting of a substituted or unsubstituted (C1–C10) aminoalkyloxy, (C1–C10) alkylcarboxy-(C1–C10) alkyl, (C1–C10) alkylamino-(C1–C10) alkylamino, (C1–C10) alkylamino-(C1–C10) alkylamino-(C1–C10) alkylamino, a substituted or unsubstituted (C1–C10) aminoalkylcarboxy, a substituted or unsubstituted arylamino-(C1–C10) alkyl, a substituted or unsubstituted (C1–C10) aminoalkyloxy-(C1–C10) alkyl, a substituted or unsubstituted (C1–C10) aminoalkylaminocarbonyl, (C1–C10) quaternaryammonium alkylcarboxy, H2N—HC(Q5)—C(O)—O—, H2N—HC(Q5)—C(O)—N(H)—, (C1–C10) azidoalkyloxy, (C1–C10) cyanoalkyloxy, P.G.-HN—HC(Q5)—C(O)—O—, (C1–C10) guanidinoalkyloxy, and (C1–C10) guanidinoalkylcarboxy; or a pharmaceutically acceptable salt thereof.

13. The compound of claim 12, wherein the compound has the formula:

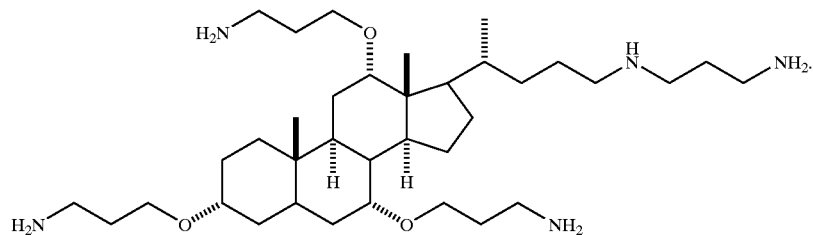

14. The compound of claim 12, wherein the compound has the formula:

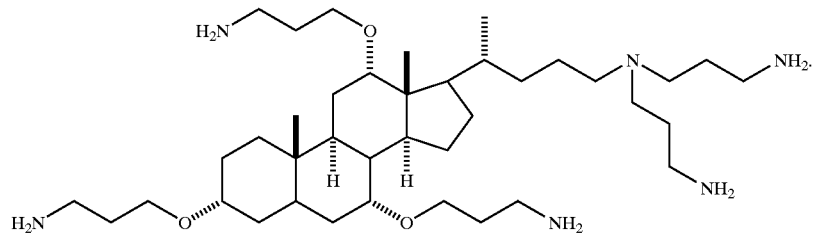

15. The compound of claim 12, wherein the compound has the formula:

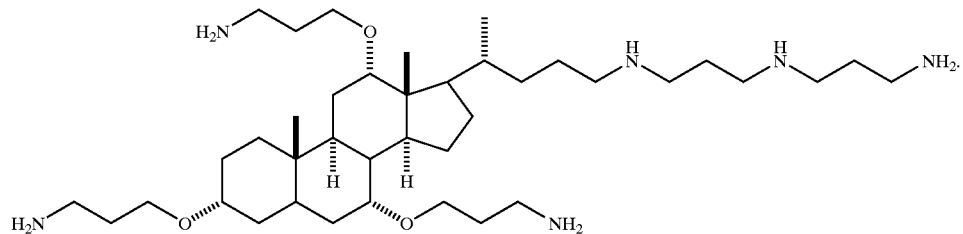

16. The compound of claim 1, wherein $R_{12}$ is selected from the group consisting of hydroxyl, a substituted or unsubstituted (C1–C10) alkyl, (C1–C10) hydroxyalkyl, (C1–C10) alkyloxy-(C1–C10) alkyl, (C1–C10) alkylcarboxy-(C1–C10) alkyl, (C1–C10) alkylamino-(C1–C10) alkyl, (C1–C10) alkylamino-(C1–C10) alkylamino, (C1–C10) alkylamino-(C1–C10) alkylamino-(C1–C10) alkylamino, a substituted or unsubstituted (C1–C10) aminoalkyl, a substituted or unsubstituted aryl, a substituted or unsubstituted arylamino-(C1–C10) alkyl, (C1–C10) haloalkyl, C2–C6 alkenyl, C2–C6 alkynyl, oxo, a linking group attached to a second steroid, a substituted or unsubstituted (C1–C10) aminoalkyloxy, a substituted or unsubstituted (C1–C10) aminoalkyloxy-(C1–C10) alkyl, a substituted or unsubstituted (C1–C10) aminoalkylcarboxy, a substituted or unsubstituted (C1–C10) aminoalkylaminocarbonyl, a substituted or unsubstituted (C1–C10) aminoalkylcarboxamido, H2N—HC(Q5)—C(O)—O—, H2N—HC(Q5)—C(O)—N(H)—, (C1–C10) azidoalkyloxy, (C1–C10) cyanoalkyloxy, P.G.-HN—HC(Q5)—C(O)—O—, (C1–C10) guanidinoalkyl oxy, (C1–C10) quaternaryammoniumalkylcarboxy, and (C1–C10) guanidinoalkyl carboxy, where Q5 is a side chain of any amino acid, P.G. is an amino protecting group.

* * * * *